(12) United States Patent
Walker et al.

(10) Patent No.: US 11,846,644 B2
(45) Date of Patent: Dec. 19, 2023

(54) CONVEYOR ASSEMBLY

(71) Applicant: GEN-PROBE INCORPORATED, San Diego, CA (US)

(72) Inventors: George T. Walker, San Diego, CA (US); Matthias Merten, San Diego, CA (US); Gary D. Lair, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 556 days.

(21) Appl. No.: 15/931,282

(22) Filed: May 13, 2020

(65) Prior Publication Data

US 2020/0278369 A1    Sep. 3, 2020

Related U.S. Application Data

(63) Continuation of application No. 15/434,968, filed on Feb. 16, 2017, now abandoned.
(Continued)

(51) Int. Cl.
*G01N 35/10* (2006.01)
*G01N 35/04* (2006.01)
(Continued)

(52) U.S. Cl.
CPC ....... *G01N 35/1011* (2013.01); *C12Q 1/6806* (2013.01); *G01N 35/00732* (2013.01);
(Continued)

(58) Field of Classification Search
CPC ......... G01N 35/1001; G01N 35/00732; G01N 35/00871; G01N 35/04; G01N 35/1065;
(Continued)

(56) References Cited

U.S. PATENT DOCUMENTS

6,335,166 B1    1/2002 Ammann et al.
7,897,337 B2    3/2011 Macioszek et al.
(Continued)

FOREIGN PATENT DOCUMENTS

EP    2485059 A1    8/2012
EP    2889236 A1    7/2015

OTHER PUBLICATIONS

Hawker, Charles D., "Laboratory Automation: Total and Subtotal," *Clinics in Laboratory Medicine 27*: 749-770, Elsevier (2007).
(Continued)

*Primary Examiner* — Benjamin R Whatley
(74) *Attorney, Agent, or Firm* — Sterne, Kessler, Goldstein & Fox P.L.L.C.; John D. Higgins; Charles B. Cappellari

(57) ABSTRACT

A conveyor assembly for transporting a carrier coupled to a receptacle to a processing station located within a housing of an instrument. The conveyor assembly includes a spur conveyor subassembly and a buffer conveyor subassembly for transporting the carrier from a host conveyor assembly to the spur conveyor subassembly. The spur conveyor subassembly includes (i) a rotatable diverter having at least one recess for receiving and moving the carrier between the buffer conveyor subassembly and the spur conveyor subassembly and (ii) a gripper configured to grasp the carrier and move it from the diverter to the processing position located within the housing of the instrument.

22 Claims, 31 Drawing Sheets

Related U.S. Application Data

(60) Provisional application No. 62/332,831, filed on May 6, 2016, provisional application No. 62/297,348, filed on Feb. 19, 2016.

(51) Int. Cl.
  *C12Q 1/6806* (2018.01)
  *G01N 35/00* (2006.01)

(52) U.S. Cl.
  CPC ....... *G01N 35/00871* (2013.01); *G01N 35/04* (2013.01); *G01N 35/1065* (2013.01); *G01N 2035/00742* (2013.01); *G01N 2035/00782* (2013.01); *G01N 2035/00801* (2013.01); *G01N 2035/0406* (2013.01); *G01N 2035/046* (2013.01); *G01N 2035/047* (2013.01); *G01N 2035/0462* (2013.01); *G01N 2035/0465* (2013.01); *G01N 2035/0467* (2013.01); *G01N 2035/0472* (2013.01)

(58) Field of Classification Search
  CPC .......... G01N 2035/00742; G01N 2035/00782; G01N 2035/00801; G01N 2035/0406; G01N 2035/046; G01N 2035/0462; G01N 2035/0465; G01N 2035/0467; G01N 2035/047; G01N 2035/0472
  See application file for complete search history.

(56) References Cited

U.S. PATENT DOCUMENTS

| | | |
|---|---|---|
| 9,724,948 B2 | 8/2017 | Silbert et al. |
| 9,732,374 B2 | 8/2017 | Buse et al. |
| 2005/0037502 A1 | 2/2005 | Miller |
| 2009/0286249 A1 | 11/2009 | Becker et al. |
| 2010/0282003 A1 | 11/2010 | Hamada et al. |
| 2013/0065797 A1 | 3/2013 | Silbert et al. |
| 2014/0072473 A1 | 3/2014 | Haechler et al. |
| 2014/0305227 A1* | 10/2014 | Johns ...................... B04B 13/00 73/863.01 |
| 2015/0177268 A1 | 6/2015 | Reisch et al. |
| 2016/0169926 A1* | 6/2016 | Marty ................ G01N 35/1081 422/509 |
| 2016/0334431 A1* | 11/2016 | Noda .................. G01N 35/0099 |
| 2017/0185815 A1* | 6/2017 | Itoh ....................... G06K 7/1413 |
| 2017/0254827 A1 | 9/2017 | Walker et al. |
| 2018/0321268 A1* | 11/2018 | Schacher ............. B65G 37/005 |

OTHER PUBLICATIONS

EPO Communication pursuant to Article 94(3) EPC, European Application No. 17708624.6, dated Jan. 26, 2022.

\* cited by examiner

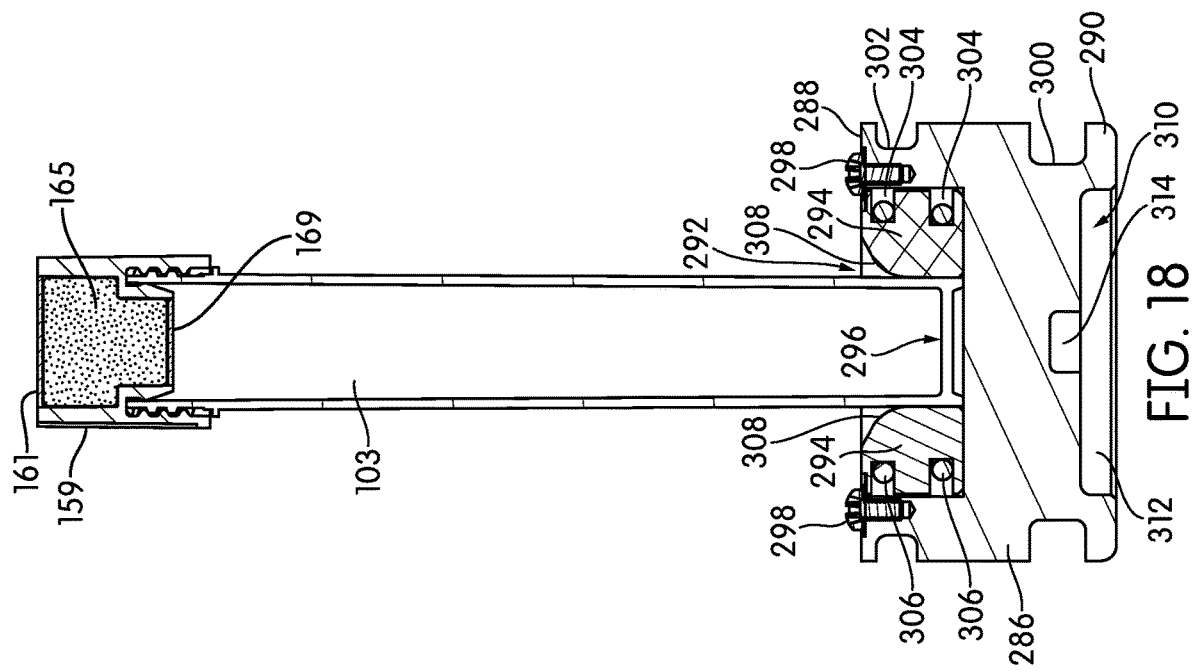
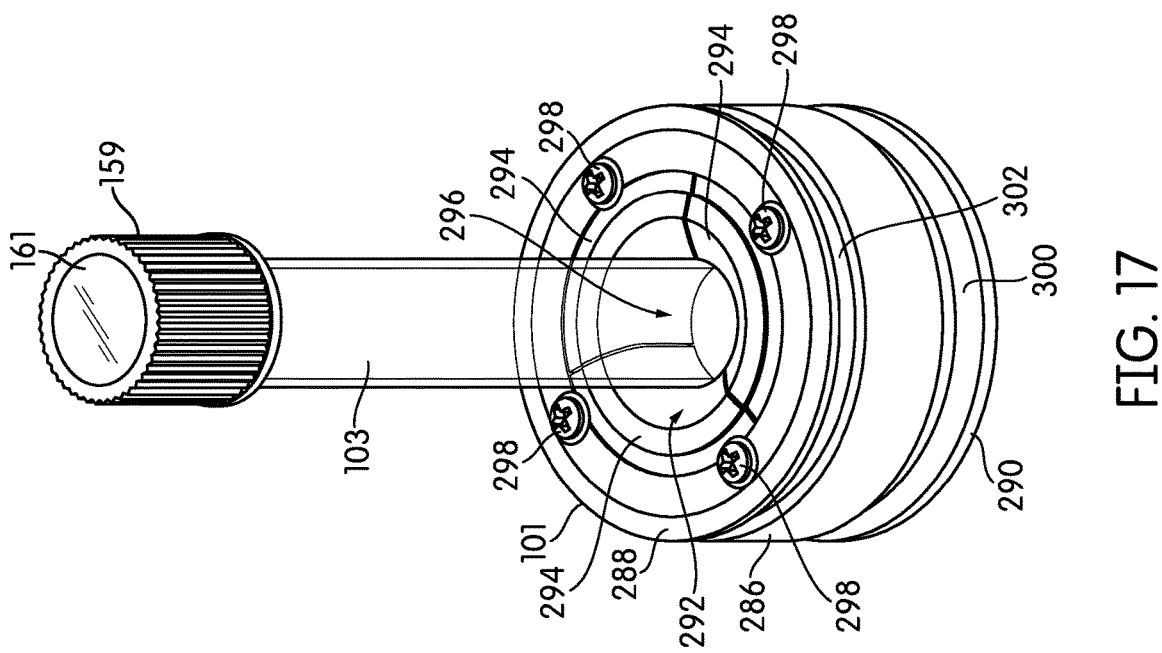

CONVEYOR ASSEMBLY

CROSS-REFERENCE TO RELATED APPLICATIONS

This application is a continuation of U.S. application Ser. No. 15/434,968, filed Feb. 16, 2017, now pending, which claims the benefit of U.S. Provisional Application Nos. 62/332,831, filed May 6, 2016, and 62/297,348, filed Feb. 19, 2016, the contents of each of which applications is hereby incorporated by reference herein in its entirety.

FIELD

Embodiments of this disclosure relate to laboratory automated instruments, systems, and methods for processing a sample.

BACKGROUND

Laboratory automated instruments and systems can have automated conveyor assemblies that transport samples among various positions within a laboratory. For example, the samples can be contained in receptacles, and the receptacles can be coupled to carriers (e.g., pucks). To transport the carriers and, in turn, the receptacles containing the samples, the carriers are placed on the conveyor assembly, and the conveyor assembly transports the carriers and the receptacles coupled to the carriers among the various positions within the laboratory.

SUMMARY

In some embodiments, an automated sample processing system includes a first instrument that includes a first automated pipettor configured to aspirate at least a portion of a sample from a first sample containing receptacle and dispense the portion of the first sample into a first processing receptacle. The automated sample processing system also includes a second instrument includes a second automated pipettor configured to aspirate at least portions of samples from processing receptacles containing samples at a first processing position within the second instrument and dispense at least portions of samples into assay receptacles. The second instrument is further configured to perform first assays on the portions of the samples contained within assay receptacles. The automated sample processing system also includes a first conveyor assembly configured to transport a first carrier coupled to the first processing receptacle containing the portion of the first sample dispensed by the first automated pipettor from the first instrument to a position outside the first instrument. The automated sample processing system also includes a second conveyor assembly configured to receive the first carrier coupled to the first processing receptacle from the first conveyor assembly at the position outside the first instrument, and to transport the first carrier to a first position outside the second instrument.

The automated sample processing system also includes a third conveyor assembly. The third conveyor assembly is configured to receive the first carrier from the second conveyor assembly at the first position outside the second instrument. The third conveyor assembly is also configured to transport the first carrier to the first processing position within the second instrument at which the second automated pipettor of the second instrument aspirates at least a portion of the first sample from the first processing receptacle for subsequently dispensing the portion of the first sample into an assay receptacle. The third conveyor assembly is also configured to, after the second automated pipettor of the second instrument aspirates at least a portion of the first sample from the first processing receptacle, transport the first carrier coupled to the first processing receptacle from the first processing position to a second position outside the second instrument. The third conveyor assembly is also configured to transfer the first carrier at the second position outside the second instrument to the second conveyor assembly.

The second instrument can be configured to perform first assays by subjecting samples contained within assay receptacles to nucleic acid amplification reaction conditions. The first instrument can be further configured to couple the first processing receptacle with the first carrier. The first instrument can further include an input bay configured to manually receive the first sample containing receptacle. The first instrument can further include an input bay configured to automatically receive the first sample containing receptacle.

The automated sample processing system can further include a third instrument that includes a third automated pipettor configured to aspirate at least portions of samples from processing receptacles containing samples at a second processing position within the third instrument and dispense the portions of samples into second assay receptacles. The third instrument is further configured to perform second assays on samples contained within assay receptacles.

The first assays can be different than the second assays. The third instrument can be configured to perform the second assays by subjecting samples contained within assay receptacles to nucleic acid amplification reaction conditions. Subjecting samples contained within assay receptacles to nucleic acid amplification reaction conditions of the first assay can include adding a first reagent to samples contained within assay receptacles, and subjecting samples contained within assay receptacles to nucleic acid amplification reaction conditions of the second assay can include adding a second reagent, different than the first reagent, to samples contained within assay receptacles. The first assays can be configured to determine the presence of a first analyte, and the second assays can be configured to determine the presence of a second analyte different than the first analyte.

The first assays can be the same as the second assays.

The automated sample processing system can further include a fourth conveyor assembly configured to receive a second carrier coupled to a second processing receptacle from the second conveyor assembly at a first position outside the third instrument. The fourth conveyor assembly is further configured to transport the second carrier to the second processing position within the third instrument at which the third automated pipettor of the third instrument aspirates at least a portion of a second sample from the second processing receptacle for subsequently dispensing the portion of the second sample into a second assay receptacle. And the fourth conveyor assembly is further configured to, after the third automated pipettor of the third instrument aspirates the portion of the second sample from the second processing receptacle, transport the second carrier from the second processing position to a second position outside the third instrument. The first automated pipettor of the first instrument is further configured to aspirate at least a portion of the second sample from the second sample containing receptacle and dispense the portion of the second sample into the second processing receptacle. The first conveyor assembly is further configured to transport the second carrier coupled to the second processing receptacle containing the portion of the second sample dispensed by the first automated pipettor from the first instrument to the position outside the first instrument. The second conveyor assembly is further configured to receive the second carrier coupled to the second processing receptacle from the first conveyor assembly at the position outside the first instrument, and transport the second carrier to the first position outside the third instrument.

The first instrument cam include a writer configured to transfer a first identifier to at least one of the first carrier and the first processing receptacle, and to transfer a second identifier to at least one of the second carrier and the second processing receptacle. The writer can be a printer configured to print the first identifier on at least one of the first carrier and the first processing receptacle, and to print the second identifier on at least one of the second carrier and the second processing receptacle. The writer can be configured to transfer the first identifier to the first carrier and the second identifier to the second carrier. The first carrier can include a first RFID tag, and the second carrier can include a second RFID tag. The writer can include an RFID writer configured to transmit the first identifier to the first RFID tag and the second identifier to the second RFID tag.

The second conveyor system can include a first portion configured to transport carriers from the position outside the first instrument to the first position outside the second instrument. The second conveyor system can also include a second portion configured to transport carriers from the first position outside the second instrument to the second position outside the second instrument. And the second conveyor system can include a diverter configured to transfer the first carrier from the first portion of the second conveyor assembly to the third conveyor assembly based on the first identifier. The divert is also configured to transfer the second carrier from the first portion of the second conveyor assembly to the second portion of the second conveyor assembly based on the second identifier.

The automated sample processing system can further include a control system configured to transmit a control signal to the diverter. The diverter can be configured to transfer the first carrier from the first portion of the second conveyor assembly to the third conveyor assembly based on the control signal. The diverter can be also configured to transfer the second carrier from the first portion of the second conveyor assembly to the second portion of the second conveyor assembly based on the control signal. The second conveyor assembly can further include a sensor configured to detect the first identifier of the first carrier and the second identifier of the second carrier, and to transmit a sensor signal to the control system based on the detected first identifier and the detected second identifier. The control system is configured to adjust the control signal transmitted to the diverter based on the sensor signal received from the sensor. The sensor of the second conveyor assembly can include an RFID antenna. The sensor of the second conveyor assembly can also be an image sensor.

The third conveyor assembly can include a sensor configured to detect the first identifier of the first carrier positioned at the first processing position. The second instrument can be configured to start aspirating the portion of the first sample from the first processing receptacle containing the portion of the first sample at the first processing position within the second instrument based on the detected first identifier. The sensor of the third conveyor assembly can include an RFID antenna. The sensor of the third conveyor assembly can also be an image sensor.

The second conveyor system can further include a first portion configured to transport carriers from the second position outside the second instrument to the first position outside the third instrument, and a second portion configured to transport carriers from the first position outside the third instrument to the second position outside the third instrument. The second conveyor system can further include a diverter configured to transfer the second carrier from the first portion of the second conveyor assembly to the fourth conveyor assembly based on the second identifier of the second carrier. The divert can also be configured to transfer the first carrier from the first portion of the second conveyor assembly to the second portion of the second conveyor assembly based on the first identifier.

The automated sample processing system can also include a control system configured to transmit a control signal to the diverter. The diverter can be configured to transfer the second carrier from the first portion of the second conveyor assembly to the fourth conveyor assembly based on the control signal, and configured to transfer the first carrier from the first portion of the second conveyor assembly to the second portion of the second conveyor assembly based on the control signal. The second conveyor assembly further includes a sensor configured to detect the first identifier of the first carrier and the second identifier of the second carrier, and to transmit a second sensor signal to the control system based on the detected first identifier and the detected second identifier. The control system can be configured to adjust the control signal transmitted to the diverter based on the second sensor signal received from the sensor of the second conveyor assembly. The sensor of the second conveyor assembly includes an RFID antenna. The sensor of the second conveyor assembly can also be an image sensor.

The fourth conveyor assembly can include a sensor configured to detect the second identifier of the second carrier positioned at the second processing position. And the third instrument can be configured to start aspirating the portion of the second sample from the second processing receptacle containing the second sample at the second processing position within the third instrument based on the detected second identifier. The sensor of the fourth conveyor assembly can include an RFID antenna. The sensor of the fourth conveyor assembly can also be an image sensor.

The third instrument can further include a housing defining a substantially enclosed volume, and the third automated pipettor can be positioned in the volume.

The third conveyor assembly can include a first conveyor subassembly that includes an input portion configured to transport the first carrier from the second conveyor assembly to a first transfer position. The first conveyor subassembly can also include an output portion configured to transport the first carrier from a second transfer position to the second position outside the second instrument. The third conveyor assembly can also include a second conveyor subassembly configured to transport the first carrier between a third transfer position and the first processing position within the instrument. The third conveyor assembly can also include a diverter configured to transport the first carrier from the first transfer position to the third transfer position while simultaneously transporting another carrier from the third transfer position to the second transfer position. The second conveyor subassembly can include a gripper configured to secure the first carrier to the first processing receptacle as a distal end of the second automated pipettor is withdrawn from the first processing receptacle. The second conveyor subassembly can also include a movable track configured to transport the first carrier between the third transfer position and the first processing position within the instrument.

The first carrier can be a puck.

The first instrument can further include a first housing, and the first automated pipettor is positioned in the first housing. The second instrument can further include a second housing, and the second automated pipettor is positioned in the second housing.

The first instrument can further include a sample processing station configured to decap and cap at least one of the first sample containing receptacle and the first processing receptacle.

In some embodiments, an automated sample processing system includes a first conveyor assembly configured to transport a first carrier coupled to a first processing receptacle containing a first sample, and a second carrier coupled to a second processing receptacle containing a second sample. The automated sample processing system includes a second conveyor assembly configured to receive the first carrier from the first conveyor assembly, transport the first carrier to a first processing position, and return the first carrier to the first conveyor assembly. The automated sample processing system also includes a first instrument that includes a first automated pipettor configured to aspirate at least a portion of the first sample from the first processing receptacle at the first processing position and dispense the portion of the first sample into a first assay receptacle. The first processing position is within the first instrument. And the first instrument is further configured to perform a first assay on the first sample contained within the first assay receptacle to determine the presence of a first analyte in the first sample. The automated sample processing system includes a third conveyor assembly configured to receive the second carrier from the first conveyor assembly, transport the second carrier to a second processing position, and return the second carrier to the first conveyor assembly. The automated sample processing system includes a second instrument that includes a second automated pipettor configured to aspirate at least a portion of the second sample from the second processing receptacle at the second processing position and dispense the portion of the second sample into a second assay receptacle. The second processing position is within the second instrument. And the second instrument is further configured to perform a second assay on the second sample contained within the second assay receptacle to determine the presence of a second analyte in the second sample.

The first assay can include subjecting the first sample contained within the first assay receptacle to nucleic acid amplification reaction conditions. The first assay can be different than the second assay.

The second assay can include subjecting the second sample contained within the second assay receptacle to nucleic acid amplification reaction conditions.

The first analyte and the second analyte can be the same analytes, or the first analyte and the second analyte can be different analytes.

At least one of the first processing receptacle and the first carrier can include a first identifier, and at least one of the second processing receptacle and the second carrier can include a second identifier. The first conveyor system can also include a first portion configured to transport the first carrier and the second carrier to a first position upstream from the second conveyor system. The first conveyor system can also include a second portion configured to transport the first carrier and the second carrier to a second position upstream from the third conveyor system. And the first conveyor system can include a first diverter configured to transfer the first carrier from the first portion of the first conveyor assembly to the second conveyor assembly based on the first identifier. The diverter is also configured to transfer the second carrier from the first portion of the first conveyor assembly to the second portion of the first conveyor assembly based on the second identifier. The automated sample processing system can also include a control system configured to transmit a first control signal to the first diverter. The first diverter is configured to transfer the first carrier from the first portion of the first conveyor assembly to the second conveyor assembly based on the first control signal, and the first diverter configured to transfer the second carrier from the first portion of the first conveyor assembly to the second portion of the first conveyor assembly based on the first control signal. The first conveyor assembly further includes a first sensor configured to detect the first identifier when the first carrier is at the first position upstream from the second conveyor system, detect the second identifier when the second carrier is at the first position upstream from the second conveyor system, and transmit a first sensor signal to the control system based on the detected first identifier and the detected second identifier. The control system is also configured to adjust the first control signal transmitted to the first diverter based on the first sensor signal received from the first sensor.

The first conveyor system can further include a third portion configured to transport the first carrier and the second carrier to a third position downstream from the second instrument. The first conveyor system can further include a second diverter configured to transfer the first carrier from the second portion of the first conveyor assembly to the third portion of the first conveyor assembly based on the first identifier. The second diverter is also configured to transfer the second carrier from the second portion of the first conveyor assembly to the third conveyor assembly based on the second identifier.

The control system can be further configured to transmit a second control signal to the second diverter. The second diverter is configured to transfer the second carrier from the second portion of the first conveyor assembly to the third conveyor assembly based on the second control signal, and configured to transfer the first carrier from the second portion of the first conveyor assembly to the third portion of the first conveyor assembly based on the second control signal. The first conveyor assembly can further include a second sensor configured to detect the first identifier when the first carrier is at second position upstream from the third conveyor system, detect the second identifier when the second carrier is at the second position upstream from the third conveyor system, and transmit a second sensor signal to the control system based on the detected first identifier and the detected second identifier. The control system can also be configured to adjust the second control signal transmitted to the second diverter based on the second sensor signal received from the second sensor.

The second conveyor assembly can further include a third sensor configured to detect the first identifier of the first carrier positioned at the first processing position. The first instrument is configured to start aspirating the portion of the first sample from the first processing receptacle at the first processing position based on the detected first identifier.

The third conveyor assembly can further include a fourth sensor configured to detect the second identifier of the second carrier positioned at the second processing position, and wherein the second instrument is configured to start aspirating the portion of the second sample from the second processing receptacle at the second processing position based on the detected second identifier.

In some embodiments, a conveyor assembly transports a plurality of carriers coupled to respective processing receptacles from a host conveyor assembly outside an instrument to a processing position within the instrument. The conveyor assembly includes a buffer conveyor subassembly configured to transport the plurality of carriers coupled to the respective receptacles from the host conveyor assembly to a first transfer position and configured to transport the plurality of carriers coupled to the respective receptacles from a second transfer position to the host conveyor assembly. The conveyor assembly also includes a spur conveyor subassembly configured to transport the plurality of carriers coupled to the respective receptacles from a third transfer position to the processing position within the instrument. The spur conveyor subassembly includes a diverter configured to transport one of the plurality of carriers coupled to one of the respective receptacles from the first transfer position to the third transfer position while simultaneously transporting another one of the plurality of carriers coupled to another one of the respective receptacles from the third transfer position to the second transfer position.

The buffer conveyor subassembly can be mounted to an outer surface of the instrument. The third transfer position can be outside of the instrument. The spur conveyor subassembly can further include a cover that encloses a portion of a path within the instrument between the third transfer position and the processing position. The cover can define an opening configured to allow a distal end of a pipettor of the instrument to pass. The distal end of the pipettor can include a disposable tip. The cover can have a substantially inverted U-shape.

The spur conveyor subassembly can further include a sensor configured to detect an identifier of one of the plurality of carriers positioned at the processing position of the instrument. The sensor can include an RFID reader.

The buffer conveyor subassembly can include a single movable track. A portion of the diverter can overlap the single movable track forming an input portion and an output portion of the buffer conveyor subassembly. The input portion of the buffer conveyor subassembly can have a length sufficient to queue a plurality of carriers. The instrument can be configured to aspirate at least portions of samples from processing receptacles coupled to carriers at the processing position and to dispense the portions of the samples into cavities defined by an assay receptacle. The length of the input portion of the buffer conveyor subassembly can be sufficient to queue a number of carriers at least equal to a number of cavities defined by the assay receptacle.

The diverter can define a first concave recess and a second concave recess. The first concave recess is configured to receive a carrier at the first transfer position, and the second concave recess is configured to receive a carrier at the third transfer position. The diverter can further define a third concave recess. The first, second, and third concave recess of the diverter can be equally spaced about a periphery of the diverter.

The diverter can be configured to rotate about an axis. The diverter can be configured to rotate about the axis in only one direction, or the diverter can be configured to rotate about the axis in two directions. The conveyor assembly can further include a base and a drive assembly coupled to the base and configured to rotate the diverter. The diverter can be rotatably coupled to the base.

The spur conveyor can define a single path along which the plurality of carriers coupled to the respective receptacles are transported. The spur conveyor further can include a portion defining a recess configured to receive a portion a receptacle coupled a carrier positioned at the processing position within the instrument.

In some embodiments, the spur conveyor subassembly can further include a movable gripper configured to grasp one of the plurality carriers at the third transfer position and transport the one of the plurality carriers to the processing position within the instrument. The gripper can include at least two movable prongs configured to apply pressure to the carrier grasped by the gripper. Each of the at least two movable prongs can include a portion having a protrusion configured to mate with a groove defined by the carrier grasped by the gripper such that as a distal end of a pipettor of the instrument is removed from a respective processing receptacle of the carrier grasped by the gripper. The gripper can hold the carrier to the spur conveyor subassembly. The at least two movable prongs can be further configured to contact a receptacle coupled to the carrier grasped by the gripper.

In other embodiments, the spur conveyor subassembly includes a movable track configured to transport one of the plurality carriers between the third transfer position the processing position within the instrument.

In some embodiments, a sample processing method includes verifying that an identifier of a first carrier detected at a first position on a host conveyor assembly is associated with a first sample on which a first assay is scheduled to be performed with a first instrument. The method also includes diverting the first carrier from the host conveyor assembly to a first intermediate conveyor assembly, and transporting the first carrier to a first processing position within the first instrument using the first intermediate conveyor assembly. The method also includes verifying that an identifier of the first carrier detected at the first processing position is associated with the first sample on which the first assay is scheduled to be performed with the first instrument. The method also includes, at the first processing position, transferring at least a portion of the first sample from a first processing receptacle coupled to the first carrier to a first assay receptacle using a first automated pipettor of the first instrument. The method also includes performing the first assay by subjecting the portion of the first sample in the first assay receptacle to nucleic acid amplification reaction conditions using the first instrument. And the method includes transporting the first carrier from the first processing position to the host conveyor assembly using the first intermediate conveyor assembly.

The method can also include verifying that an identifier of a second carrier detected at the first position on the host conveyor assembly is associated with a second sample on which the first assay is scheduled to be performed with the first instrument. The method can also include diverting the second carrier from the host conveyor assembly to the first intermediate conveyor assembly. The method can also include transporting the second carrier to the first processing position within the first instrument using the intermediate conveyor assembly, and verifying that an identifier of the second carrier detected at the first processing position is associated with the second sample on which the first assay is scheduled to be performed with the first instrument. The method can also include, at the first processing position, transferring at least a portion of the second sample from a second processing receptacle coupled to the second carrier to the first assay receptacle using the first automated pipettor. The method can also include performing the first assay by subjecting the portion of the second sample in the first assay receptacle to nucleic acid amplification reaction conditions using the first instrument, and transporting the second carrier from the first processing position to the host conveyor assembly using the intermediate conveyor assembly.

Transporting the second carrier to the first processing position within the first instrument using the intermediate conveyor assembly can occur after the transporting the first carrier from the first processing position to the host conveyor assembly using the first intermediate conveyor assembly. Transporting the second carrier to the first processing position within the first instrument using the intermediate conveyor assembly can also occur concurrently with the transporting the first carrier from the first processing position to the host conveyor assembly using the first intermediate conveyor assembly.

The method can also include determining whether an identifier of a second carrier detected at the first position on the host conveyor assembly is associated with a second sample on which the first assay is scheduled to be performed with a first instrument. The method can also include bypassing the second carrier past the intermediate conveyor assembly to a second position on the host conveyor assembly when the identifier of the second carrier detected at the first position on the host conveyor assembly is not associated with the second sample on which the first assay will be performed. The method can also include determining whether an identifier of the second carrier detected at the second position on the host conveyor assembly is associated with a third sample on which a second assay is scheduled to be performed with a second instrument. The method can also include diverting the second carrier from the host conveyor assembly to a second intermediate conveyor assembly. The method can also include transporting the second carrier to a second processing position within the second instrument using the second intermediate conveyor assembly, and determining whether an identifier of the second carrier detected at the second processing position is associated with the third sample on which the second assay is scheduled to be performed with the first instrument. The method can also include, at the second processing position, transferring at least a portion of the third sample from a second processing receptacle coupled to the second carrier to a second assay receptacle using a second automated pipettor of the second instrument. The method can also include performing the second assay by subjecting the portion of the third sample in the second assay receptacle to nucleic acid amplification reaction conditions using the second instrument. The method can also include transporting the second carrier coupled to the second processing receptacle from the second processing position to the host conveyor assembly using the intermediate conveyor assembly.

The second assay can be different than the first assay. Performing the first assay can include subjecting a respective portion of a sample in an assay receptacle to nucleic acid amplification reaction conditions that promotes a polymerase chain reaction, and performing the second assay can include subjecting a respective portion of a sample in an assay receptacle to nucleic acid amplification reaction conditions that promotes a transcription-based amplification reaction.

The second assay can be the same as the first assay. Performing the first assay can include subjecting a respective portion of a sample in an assay receptacle to nucleic acid amplification reaction conditions that promotes a polymerase chain reaction, and performing the second assay includes subjecting a respective portion of a sample in an assay receptacle to nucleic acid amplification reaction conditions that promotes a polymerase chain reaction.

The first assay can include subjecting a respective portion of a sample in an assay receptacle to nucleic acid amplification reaction conditions that promotes a transcription-based amplification reaction, and performing the second assay can includes subjecting a respective portion of a sample in an assay receptacle to nucleic acid amplification reaction conditions that promotes a transcription-based amplification reaction.

The method can also include, before the transporting the second carrier to the first processing position within the first instrument using the intermediate conveyor assembly, queuing a predetermined number of carriers on the intermediate conveyor assembly. The predetermined number can correspond to a number of sample receiving cavities defined by the first assay receptacle.

In some embodiments, an automated sample processing method includes aspirating at least a portion of a first sample from a first sample containing receptacle using a first automated pipettor of a first instrument, and dispensing the portion of the first sample into a first processing receptacle using the automated pipettor of the first instrument. The method can also include transporting a first carrier coupled to the first processing receptacle containing the first sample from a position inside the first instrument to a host conveyor assembly using a first intermediate conveyor assembly, and transporting the first carrier from the host conveyor assembly to a first processing position within a second instrument using a second intermediate conveyor assembly. The method can also include aspirating at least a portion of the first sample from the first processing containing receptacle at the first processing position using a second automated pipettor of the second instrument, and dispensing the portion of the first sample into a first assay receptacle using the second automated pipettor of the second instrument. The method can also include performing a first assay on the portion of the first sample in the first assay receptacle using the second instrument, and transporting the first carrier from the first processing position to the host conveyor assembly using the second intermediate conveyor assembly.

Performing the first assay can include subjecting the portion of the first sample in the first assay receptacle to nucleic acid amplification reaction conditions.

The method can also include coupling the first processing receptacle with the first carrier using the first instrument. The method can also include manually inserting the first sample containing receptacle into an input bay of the first instrument, or automatically inserting the first sample containing receptacle into an input bay of the first instrument.

The method can also include aspirating at least a portion of a second sample from a second sample containing receptacle using the first automated pipettor of the first instrument, and dispensing the portion of the second sample into a second processing receptacle using the first automated pipettor of the first instrument. The method can also include transporting a second carrier coupled to the second processing receptacle containing the second sample from the position inside the first instrument to the host conveyor assembly using the first intermediate conveyor assembly, and transporting the second carrier from the host conveyor assembly to a second processing position within a third instrument using a third intermediate conveyor assembly. The method can also include aspirating at least a portion of the second sample from the second processing receptacle at the second processing position using a third automated pipettor of the third instrument, and dispensing the portion of the second sample into a second assay receptacle using the third automated pipettor of the instrument. The method can also include performing a second assay on the portion of the second sample in the second assay receptacle using the third instrument, and transporting the second carrier from the second processing position to the host conveyor assembly using the third intermediate conveyor assembly.

The first assay can be different than the second assay. The first assay can be configured to determine the presence of a first analyte, and the second assay is configured to determine the presence of a second analyte different than the first analyte.

The first assay can be the same as the second assay. The first assay can be configured to determine the presence of a first analyte, and the second assay can be configured to determine the presence of the first analyte.

Performing the second assay can include subjecting the portion of the second sample in the second assay receptacle to nucleic acid amplification reaction conditions.

The method can also include transporting the first carrier coupled to the first processing receptacle on the host conveyor assembly such that the first carrier bypasses the second processing position within the third instrument. The method can also include transporting the second carrier coupled to the second processing receptacle on the host conveyor assembly such that the second carrier bypasses the first processing position within the second instrument.

The method can also include decapping at least one of the first sample containing receptacle and the first processing at a sample processing station of the first instrument, and capping the at least one of the first sample containing receptacle and the first processing at the sample processing station of the first instrument.

In some embodiments, an automated sample processing method includes transporting a first carrier coupled to a first processing receptacle containing a first sample from a host conveyor assembly to a first processing position within a first instrument using a first intermediate conveyor assembly. The method also includes aspirating at least a portion of the first sample from the first processing containing receptacle at the first processing position using a first automated pipettor of the first instrument. The method also includes dispensing the portion of the first sample into a first assay receptacle using the first automated pipettor of the first instrument. The method also includes performing a first assay on the portion of the first sample in the first assay receptacle using the first instrument. The method also includes transporting the first carrier from the first processing position to the host conveyor assembly using the first intermediate conveyor assembly, and transporting a second carrier coupled to a second processing receptacle containing a second sample from the host conveyor assembly to a second processing position within a second instrument using a second intermediate conveyor assembly. The method also includes aspirating at least a portion of the second sample from the second processing receptacle at the second processing position using a second automated pipettor of the second instrument, and dispensing the portion of the second sample into a second assay receptacle using the second automated pipettor of the second instrument. The method also includes performing a second assay on the portion of the second sample in the second assay receptacle using the second instrument, transporting the second carrier from the second processing position to the host conveyor assembly using the second intermediate conveyor assembly.

Performing the first assay can include subjecting the portion of the first sample in the first assay receptacle to nucleic acid amplification reaction conditions.

The first assay can be different than the second assay, or the first assay can be the same as the second assay.

Performing the second assay can include subjecting the portion of the second sample in the second assay receptacle to nucleic acid amplification reaction conditions.

The method can also include transporting the first carrier coupled to the first processing receptacle on the host conveyor assembly such that the first carrier bypasses the second processing position within the second instrument. The method can also include transporting the second carrier coupled to the second processing receptacle on the host conveyor assembly such that the second carrier bypasses the first processing position within the first instrument.

In some embodiments, an automated conveyor assembly transports carriers coupled to processing receptacles from (i) another conveyor assembly that transports carriers to (ii) a processing position within an instrument. The automated conveyor assembly includes a gripper configured to selectively grasp a carrier and move between (i) a first position and (ii) the processing position in the instrument. The automated conveyor assembly includes a diverter defining a recess configured to receive a carrier. The diverter being rotatable between (i) a first position at which the recess is aligned with the other conveyor assembly and (ii) a second position at which the recess is aligned with the first position of the gripper.

The diverter can further define a second recess aligned with the first position of the gripper when the diverter is at the first position. The second recess can be aligned with the other conveyor assembly when the diverter is at the second position.

The diverter can further define a third recess and is movable between the first position, the second position, and a third position at which the first recess is aligned with the other conveyor assembly, the second recess is aligned with the other conveyor assembly, and the third recess is aligned with the first position of the gripper.

The first recess, the second recess, and the third recess can be spaced equally about an axis about which the diverter rotates.

The gripper can include at least two movable prongs configured to apply pressure to the carrier grasped by the gripper. Each of the at least two movable prongs can include a portion having a protrusion configured to mate with a groove defined by the carrier grasped by the gripper such that, as a distal end of a pipettor of the instrument is removed from a respective processing receptacle of the carrier grasped by the gripper, the gripper holds the carrier to the automated conveyor assembly. Each of the at least two movable prongs can include a portion shaped to closely correspond to a respective portion of a perimeter of the carrier. Each of the at least two movable prongs can include a portion that, when the gripper is grasping the carrier, overlaps in a vertical direction at least a respective portion of the carrier.

The first position of the gripper can be outside the instrument.

The automated conveyor assembly can further include a cover that encloses a portion of a path between the first position of the gripper and the processing position in the instrument. The cover can define an opening configured to allow a distal end of a pipettor of the instrument to pass.

In some embodiments, a diverter transports carriers between a first automated conveyor assembly path and a second automated conveyor assembly path. The diverter includes a first recess configured to receive a first carrier and a second recess spaced apart from the first recess and configured to receive a second carrier. The diverter is rotatable between (i) a first position at which the first recess is aligned with the first automated conveyor assembly path and the second recess is aligned with the second automated conveyor assembly path, and (ii) a second position at which the first recess is aligned with the second automated conveyor assembly path and the second recess is aligned with the first automated conveyor assembly path. The diverter transport the first carrier from the first automated conveyor assembly path to the second automated conveyor assembly path while simultaneously transporting the second carrier from second automated conveyor assembly path to the first automated conveyor assembly path.

The first automated conveyor assembly path is perpendicular to the second automated conveyor assembly path.

The diverter can further include a third recess configured to receive a third carrier. At the first position of the diverter, the third recess can be aligned with the first automated conveyor assembly path, and at the second position of the diverter, the third recess can be aligned with the first automated conveyor assembly path.

The diverter can have a circular outer periphery defining the first recess and the second recess. The first recess can be spaced from the second recess by about 120 degrees about an axis about which the diverter rotates.

In some embodiments, a method of transporting carriers to a processing position within an instrument includes transporting, using an automated conveyor assembly, a carrier from a first position to the processing position within the instrument. The method also includes grasping the carrier with a gripper and inserting a distal end of an automated pipettor into a receptacle coupled to the carrier. The method also includes aspirating, using the automated pipettor, at least a portion of a sample in the receptacle, and removing the distal end of the automated pipettor from the receptacle coupled to the carrier while the gripper is grasping the carrier.

Transporting the carrier from the first position to the processing position can include moving the gripper while the gripper is grasping the carrier.

The gripper can include at least two movable prongs, and grasping the carrier with the gripper can include moving the at least two movable prongs together to apply pressure to the carrier to secure the carrier to the gripper.

Transporting the carrier from the first position to the processing position includes transporting the carrier using a movable track.

The method can also include, after removing the distal end of the automated pipettor from the receptacle coupled to the carrier, transporting the carrier from processing position within the instrument to the first position using the automated conveyor assembly.

The first position can be outside the instrument.

In some embodiments, a method of transporting carriers includes receiving a first carrier in a first recess of a diverter from a first automated conveyor assembly, and receiving in a second carrier in a second recess of the diverter from a second automated conveyor assembly. The method also includes rotating the diverter, while the first carrier is received within the first recess and the second carrier is received within the second recess, such that the first carrier is aligned with the second automated conveyor assembly and the second carrier is aligned with the first automated conveyor assembly path. The first carrier is transported from the first automated conveyor assembly to the second automated conveyor assembly simultaneously with the second carrier being transported from the second automated conveyor assembly to the first automated conveyor assembly.

The first automated conveyor can define a first path that is perpendicular to a second path defined by the second automated conveyor assembly path. The diverter can have a circular outer periphery defining the first recess and the second recess. The first recess can be spaced from the second recess by about 120 degrees about an axis about which the diverter rotates.

The method can also include transporting, after rotating the divert, the first carrier to a processing position within an instrument using the second automated conveyor assembly. Receiving the first carrier in the first recess of the diverter can occur outside the instrument. The instrument can be an assay instrument.

In some embodiments, a carrier for transporting a receptacle using a conveyor assembly includes a main body having a top end portion and a bottom end portion. The top end portion defines a recess configured to receive a portion of the receptacle. The carrier also includes a first groove defined in an outer periphery of the main body. The first groove is configured to mate with corresponding protrusion of the conveyor assembly as the carrier is transported by the conveyor assembly. The carrier also includes a second groove separate from the first groove and defined in the outer periphery of the main body. The second groove is configured to mate with a protrusion of a movable gripper of the conveyor assembly. The main body can be cylindrical or non-cylindrical. The recess can be cylindrical.

The carrier can also include a plurality of movable retaining members positioned within the recess. The retaining members define an interior recess portion configured to receive the portion of the receptacle. The plurality of movable retaining members can form an annulus that defines the interior recess portion. Each of the plurality of movable retaining members can include a tapered surface configured to self-align the portion of the receptacle with a center of the recess when the portion of the receptacle is being inserted in the interior recess portion. Each of the plurality of movable retaining members can be biased toward a center of the interior recess portion such that each retaining member applies a force to the portion of the receptacle inserted in the interior recess portion that secures the receptacle to the carrier. The carrier can also include a biasing device configured to bias each of the plurality of retaining members toward the center of the interior recess portion. The biasing device can be a garter spring, and each of the plurality of retaining members can define a periphery groove configured to receive the garter spring. Each of the plurality of movable retaining members can have a radial stroke such that the inner recess portion varies in size to accommodate receptacles of at least two different sizes.

The lower end portion of the main body can define a second recess configured to receive a transponder. The transponder can be an RFID tag. The second recess can include a first portion shaped to receive a first type of transponder and a second portion shaped to receive a second type of transponder different than the first type. The first portion of the second recess can be cylindrical, and the second portion of the second recess can be rectangular. A center of the first portion of the second recess and a center of the second portion of the second recess can be coaxial.

Further features and advantages of the embodiments, as well as the structure and operational of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

DESCRIPTION OF THE DRAWINGS

The accompanying drawings, which are incorporated herein and form a part of the specification, illustrate the embodiments and, together with the description, further serve to explain the principles of the embodiments and to enable a person skilled in the relevant art(s) to make and use the embodiments.

FIG. 17 is a perspective view of a carrier and a receptacle according to an embodiment.

FIG. 18 is a cross-sectional view of the carrier and receptacle of FIG. 17 according to an embodiment.

The features and advantages of the embodiments will become more apparent from the detailed description set forth below when taken in conjunction with the drawings, in which like reference characters identify corresponding elements throughout.

DETAILED DESCRIPTION

Figure 1:
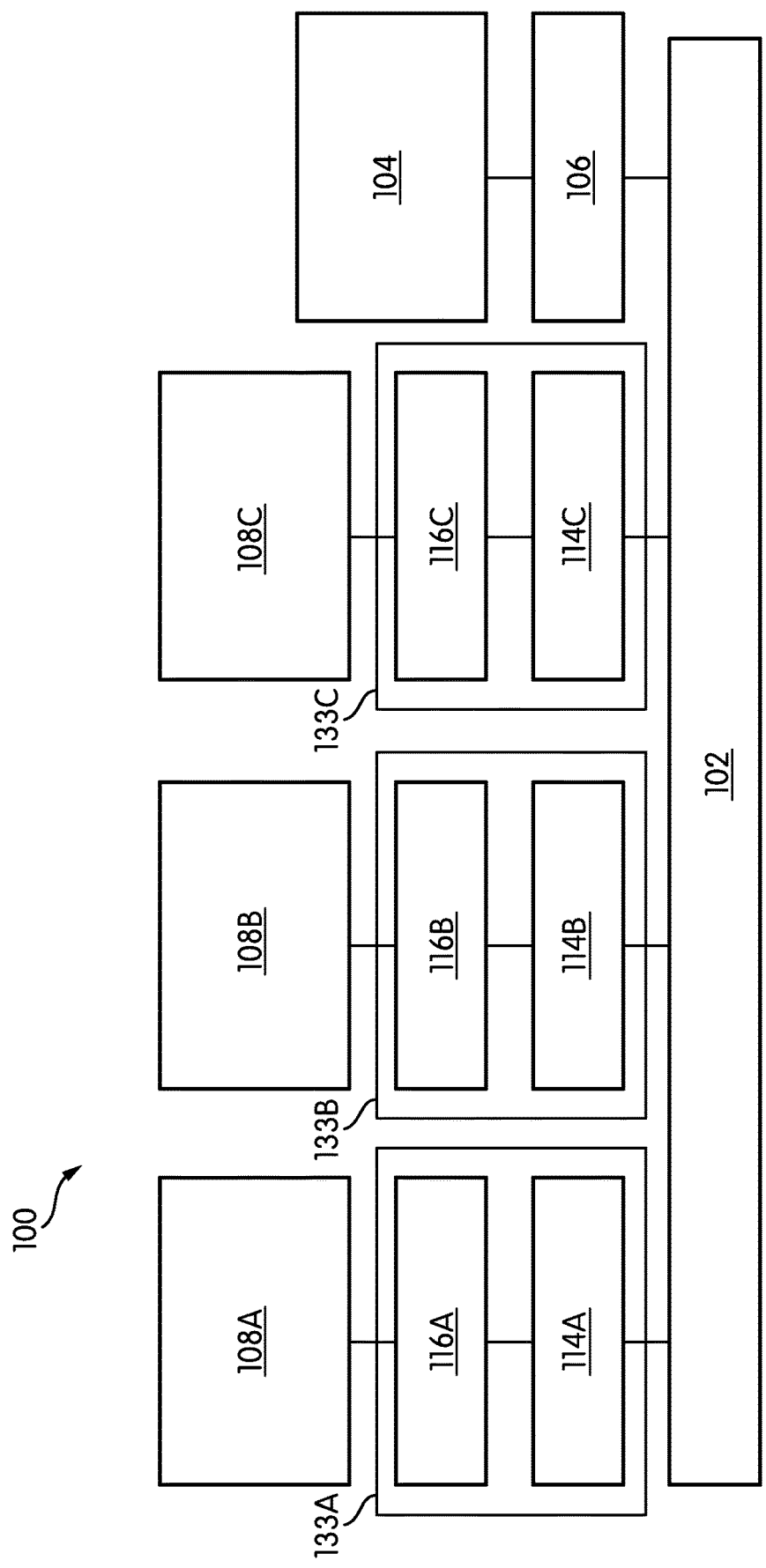
FIG. 1 is a schematic block diagram of a laboratory automated system according to an embodiment.

The present disclosure will now be described in detail with reference to embodiments thereof as illustrated in the accompanying drawings. References to "one embodiment," "an embodiment," "some embodiments," "an exemplary embodiment," "for example," "an example," "exemplary," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, "a" or "an" means "at least one" or "one or more."

As used herein, a "sample" refers to any material to be analyzed, regardless of the source. The material may be in its native form or any stage of processing (e.g., the material may be chemically altered or it may be one or more components of a sample that have been separated and/or purified from one or more other components of the sample). A sample may be obtained from any source, including, but not limited to, an animal, environmental, food, industrial or water source. Animal samples include, but are not limited to, peripheral blood, plasma, serum, bone marrow, urine, bile, mucus, phlegm, saliva, cerebrospinal fluid, stool, biopsy tissue including lymph nodes, respiratory tissue or exudates, gastrointestinal tissue, cervical swab samples, semen or other body or cellular fluids, tissues, or secretions. Samples can be diluted or contained within a receptacle containing diluents, transport media, preservative solution, or other fluids. As such, the term "sample" is intended to encompass samples contained within a diluent, transport media, and/or preservative or other fluid intended to hold a sample.

As used herein, a "sample containing receptacle" refers to any type of fluid container, including, for example, a tube, vial, cuvette, cartridge, microtiter plate, etc., that contains a sample in its native form or at any stage of processing.

As used herein, a "processing receptacle" refers to any type of fluid container, including, for example, a tube, vial, cuvette, cartridge, microtiter plate, etc., that is configured to contain a sample at a point during processing. Exemplary processing receptacles include Aptima® collection and transport tubes (Hologic, Inc., Bedford, MA).

As used herein, an "assay receptacle" refers to any type of fluid container, including, for example, a tube, vial, cuvette, cartridge, microtiter plate, etc., that is configured to contain a sample at a point while performing an assay. In some embodiments, an assay receptacle is formed with a material that can tolerate high temperatures (e.g., between 35° C.-90° C.) without deforming or leaching chemicals into a contained sample. Exemplary processing receptacles include multiple-tube units (MTUs) that each define a plurality of cavities for receiving samples, for example, MTUs used with Panther® systems sold by Hologic, Inc., Bedford, Mass.

As used herein, an "assay instrument" refers to any instrument capable of analyzing a sample and rendering a result. Any instrument capable of performing a hybridization assay, a molecular assay including a nucleic acid based amplification assay, a sequencing assay, an immunoassay, or chemistry assay on a sample is included in this definition of an assay instrument. In some embodiments, an assay can be carried out directly on a sample without any sample processing, but other samples require processing before carrying out an assay. Samples requiring some form of sample processing before subjecting the samples to the steps of an assay include, in some embodiments, cell samples, tissue samples, stool samples, mucus samples, semen samples, cerebrospinal fluid samples, blood samples, bone marrow samples, serum samples, urine samples, bile samples, respiratory samples, sputum samples, and exosome samples, among others. Exemplary assay instruments include the Tigris® and Panther® systems sold by Hologic, Inc., Bedford, MA.

As used herein, a "sample processing instrument" refers to an instrument capable of performing a processing step on a sample contained within a receptacle before performing an assay on the sample, and is not capable of analyzing a sample and/or rendering a result. For example, an instrument that transfers a sample from one receptacle to another receptacle, but does not perform an assay on the sample, is a sample processing instrument. An exemplary sample processing instrument is the Tomcat® system sold by Hologic, Inc., Bedford, MA.

As used herein, a "robotic arm" refers to an electromechanical device that translates a payload (e.g., a pipettor, a receptacle gripper (such as a pick-and-place claw), a camera, a sensor, a capper/decapper, etc.) in the X, Y, and/or Z directions. In an embodiment, a robotic arm can move in the X, Y, and Z directions.

1. Exemplary Embodiments of Laboratory Automated Systems

FIG. 1 schematically illustrates a laboratory automated system 100 according to an embodiment. System 100 includes a host conveyor assembly 102 configured to transport a plurality of carriers and receptacles coupled thereto (described further below) between at least one sample processing instrument 104 (for example, one sample processing instrument 104 as shown in FIG. 1, or two or more sample processing instruments 104) and at least one assay instrument (for example, three assay instruments 108a, 108b, and 108c as shown in FIG. 1, collectively referred to as assay instruments 108 or individually and generically as assay instrument 108). In other embodiments, system 100 includes more than one sample processing instrument 104 and more than or less than three assay instruments 108.

System 100 can also include an intermediate conveyor assembly 106 configured to transport a plurality of carriers and receptacles coupled thereto from within sample processing instrument 104 to host conveyor assembly 102. In some embodiments, intermediate conveyor assembly 106 is also configured to transport a plurality of carriers from host conveyor assembly 102 to within sample processing instrument 104.

System 100 also includes an intermediate conveyor assembly for each of assay instruments 108 (for example, intermediate conveyor assemblies 133a, 133b, and 133c, collectively referred to as intermediate conveyor assemblies 133 or generically and individually as intermediate conveyor assembly 133). Intermediate conveyor assemblies 133 are configured to transport a plurality of carriers from host conveyor assembly 102 to respective processing positions within respective assay instrument 108a, 108b, and 108c.

Figure 2:
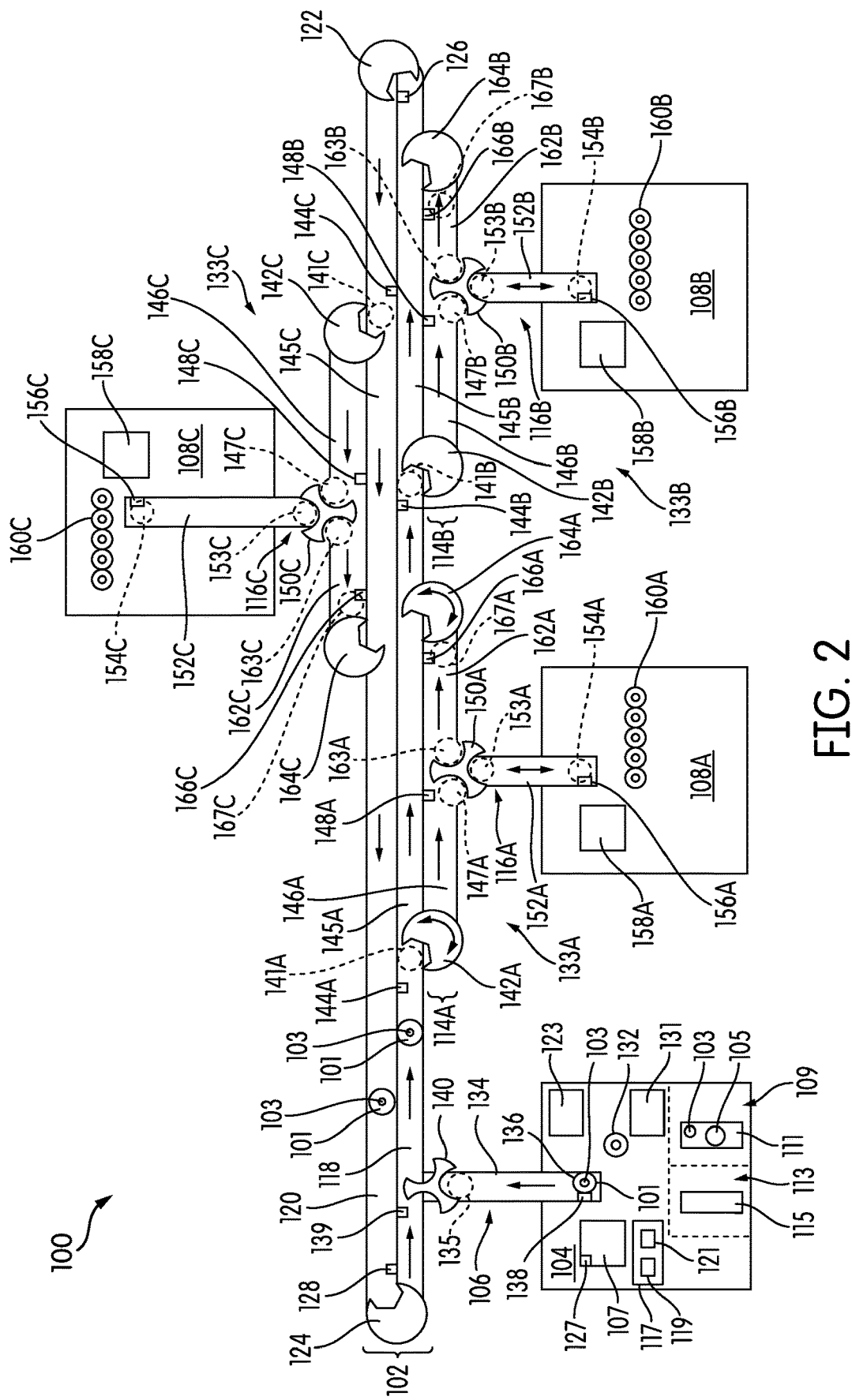
FIG. 2 is a schematic plan view of a laboratory automated system including a sample processing instrument, a host conveyor assembly, intermediate conveyor assemblies, and assay instruments, according to an embodiment.

In some embodiments, intermediate assay conveyor assemblies 133 each include a buffer conveyor assembly (buffer conveyor subassemblies 114a, 114b, and 114c as shown in FIG. 1, collectively referred to as buffer conveyor subassemblies 114 or generically and individually as buffer subassembly 114) and a spur conveyor assembly (spur conveyor subassemblies 116a, 116b, and 116c in FIGS. 1 and 2, collectively referred to as spur conveyor subassemblies 116 or generically and individually referred to as spur subassembly 116). Each buffer conveyor subassembly 114 is configured to receive carriers from host conveyor assembly 102 and transport the carriers to an intermediate position upstream from the processing position of the respective assay instrument 108. Spur conveyor subassembly 116 is configured to receive a carrier from buffer conveyor subassembly 114 and transport the carrier to the processing position of the respective assay instrument 108. The respective assay instrument 108 can process a sample contained within a receptacle coupled to the carrier at the processing position as explained further below. Spur conveyor subassembly 116 is also configured to transport the carrier from the processing position back to buffer conveyor subassembly 114. Buffer conveyor subassembly 114 is also configured to transport the carriers received from spur conveyor subassembly 116 back to host conveyor assembly 102.

After receiving carriers from a buffer conveyor subassembly of one intermediate conveyor assembly, host conveyor assembly 102 transport the carriers to other position within system 100, for example, to another assay instrument 108, to another sample processing instrument 104, or to any other instrument operatively coupled to host conveyor assembly 102.

FIG. 2 illustrates a schematic plan view of system 100 according to an embodiment. As shown in FIG. 2, system 100 includes one sample processing instrument 104, an intermediate conveyor assembly 106, a host conveyor assembly 102, three intermediate conveyor assemblies 133a-133c, and three assay instruments 108a-108c. In other embodiments, system 100 can include more than one sample processing instrument 104, or system 100 can omit sample processing instrument 104. In other embodiments, system 100 can include less than three or more than three assay instruments 108, or system 100 can omit assay instruments 108. Embodiments of each of these components of system 100 are described further below.

A. Exemplary Embodiments of Sample Processing Instruments 104

In some embodiments, sample processing instrument 104 is an instrument according to any one of the embodiments described in U.S. Patent Application Publication No. 2013/0065797, published on Mar. 14, 2013. For example, sample processing instrument 104 can include a sample processing station 107, an input bay 109 configured to movably and manually receive one or more input racks 111, an output bay 113 configured to movably receive one or more output racks 115, one or more robotic arms 117, one or more receptacle grippers 119, one or more pipettors 121, one or more incubators 123, and a controller. In some embodiments, receptacle gripper 119 is coupled to robotic arm 117 and configured to transport sample containing receptacles 105 and processing receptacles 103 within sample processing instrument 104, for example, between input racks 111, a sample processing station 107, output racks 115, and intermediate conveyor assembly 106. Each of these components of sample processing instrument 104 can be enclosed by an instrument housing. Sample containing receptacles 105 contain a sample, for example, an animal sample such as a liquid based cytology (LBC) specimen.

In some embodiments, processing receptacles 103 within instrument 104 are configured to be used in at least one of assay instruments 108.

In some embodiments, sample pipettor 121 is configured to transfer samples from sample containing receptacles 105 (e.g., liquid based cytology (LBC) specimen collection containers), to processing receptacles 103 (e.g., Aptima® collection and transport tubes available from Hologic, Inc., Bedford, MA).

Figure 19:
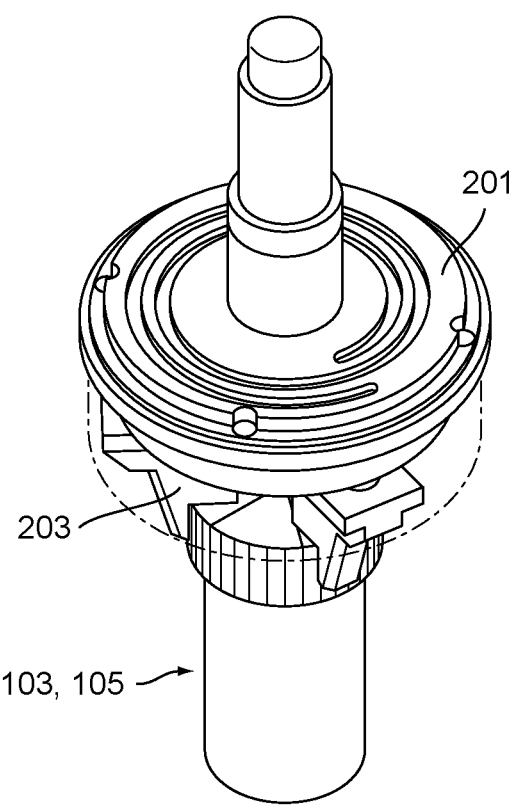
FIG. 19 is a perspective view of a capping and decapping mechanism, according to an embodiment.
Figure 20:
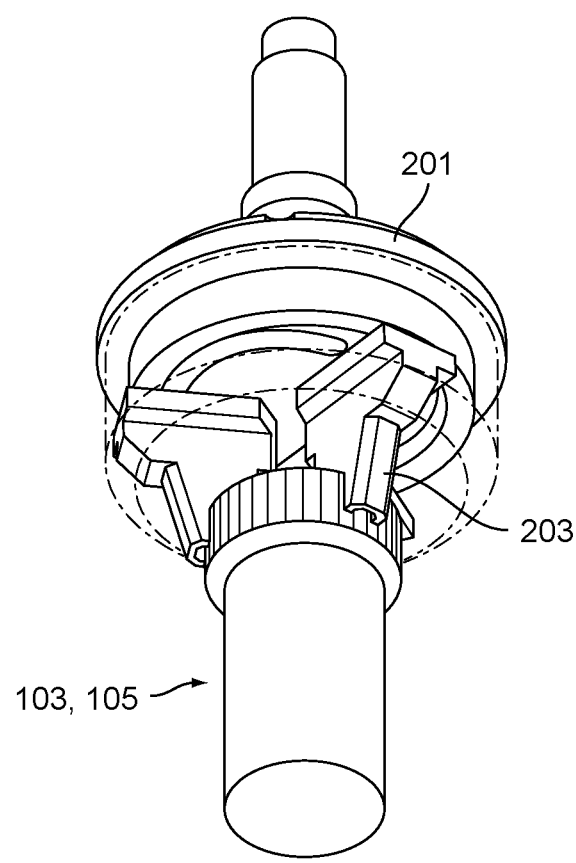
FIG. 20 is a perspective view of a capping and decapping mechanism, according to an embodiment.

In some embodiments, sample processing station 107 is configured to hold sample containing receptacles 105 and processing receptacles 103, perform barcode reading, barcode positioning, sample mixing, and capping/decapping of sample containing receptacles 105 and processing receptacles 103. In some embodiments, sample processing station 107 includes a capping/decapping mechanism configured to cap and decap receptacles, for example, sample containing receptacles 105 or processing receptacles 103. FIGS. 19 and 20 illustrate a capping/decapping mechanism 201 according to an embodiment. Capping/decapping mechanism 201 can be configured to cap and decap two or more different types of containers having a different shape and/or different shaped cap. Capping/decapping mechanism 201 can include a chuck 203 that is configured to selectively grasp a cap of a receptacle, for example, a sample containing receptacle 105 or a processing receptacle 103. As shown in FIGS. 19 and 20, chuck 203 can include a plurality of prongs that are configured to move radially inward to grasp a cap of either a sample containing receptacle 105 or a processing receptacle 103, and radially outward to release the cap. In some embodiments, capping/decapping mechanism 201 rotates to rotate the grasped cap relative to the main body of a sample containing receptacle 105 or a processing receptacle 103, thereby capping or decapping a sample containing receptacle 105 or a processing receptacle 103. In other embodiments, capping/decapping mechanism 201, while grasping the cap, remains stationary, and sample processing station 107 rotates the main body of a sample containing receptacle 105 or a processing receptacle 103 relative to the grasped cap thereby capping or decapping a sample containing receptacle 105 or a processing receptacle 103.

In some embodiments, sample processing instrument 104 includes one or more incubators 123. Incubators 123 can be configured to incubate samples directly within processing receptacles 103. For example, LBC samples such as biological samples collected in a SurePath® (Becton Dickinson, Inc., Franklin Lakes, NJ) sample containing receptacle 105 often require processing, such as reagent addition and heated incubation using incubators 123, before conducting a molecular assay. In other embodiments, LBC sample types such as those collected in a ThinPrep® (Hologic, Inc., Bedford, MA) sample containing receptacle may not require further processing such as incubation using incubators 123.

In some embodiments, sample processing instrument 104 also includes a controller that is configured to manage and process device-wide activities by delegating specific tasks to instrument sub-components or modules. Exemplary system activities include capping/decapping collection and processing receptacles, vortexing, moving collection and processing receptacles, pipetting, waste reservoir monitoring, monitoring consumable inventory, monitoring sample queues, maintaining run logs, monitoring process controls, monitoring system alarms, etc.

In some embodiments, sample processing instrument 104 includes a software user interface. In one embodiment, the user interface incorporates an integrated touch screen for operator input, instrument control, status monitoring, and displaying sample tracking information. In some embodiments, sample processing instrument 104 includes data input devices. For example, sample processing instrument 104 can include USB ports, for example, for updating system configuration files, downloading sample tracking data and run logs, and connecting additional user interface devices such as a mouse or keyboard.

In some embodiments, sample processing instrument 104 includes a hardware user interface so that a user can access various areas of sample processing instrument 104, for example, the sample input bay 109, the output bay 113, and the consumable areas. In one embodiment, sample processing instrument 104 includes two or more cabinets or drawers on the front of the automated instrument to access these areas.

Sample processing instrument 104 can also include output bay 113 configured to movably receive, for example, slidably receive, and hold one or more output racks 115. The output racks can act as input queues for assay instruments not coupled to host conveyor assembly 102.

Sample processing instrument 104 can also include input bay 109 that is configured to movably receive, for example, slidably receive, and hold one or more input racks 111.

In some embodiments, sample processing instrument 104 is configured to handle a variety of sample types, including samples collected in different shaped collection receptacles. In one such embodiment, input bay 109 is configured to hold multiple types of sample input racks 111. For example, in one embodiment, input bay 109 is configured to hold sample input racks 111 containing ThinPrep® and/or SurePath® sample containing receptacles 105, respectively. In another embodiment, each sample input rack 111 is configured to hold a single type of specimen such that if two input racks 111 are in input bay 109, one input rack 111 may contain only ThinPrep® sample containing receptacles 105, and the other input rack may contain only SurePath® sample containing receptacles 105. In another embodiment, each input rack 111 received within input bay 109 of sample processing instrument 104 is configured to hold two or more different shaped receptacles 105. For example, each input rack can be configured to hold two or more different shaped sample containing receptacles 105, for example, ThinPrep® and SurePath® sample containing receptacles 105, respectively. In such embodiments, the input rack 111 can be configured to hold SurePath® sample containing receptacles 105 (including the corresponding processing receptacles 103 in some embodiments) on one side, and ThinPrep® sample containing receptacles 105 (including the corresponding processing receptacles 103 in some embodiments) on the opposite side. In use, such a input rack 111 can hold SurePath® sample containing receptacles 105, and then if flipped upside down, the same input rack 111 can hold ThinPrep® sample containing receptacles 105. In some embodiments, processing receptacles 103 held by the input rack 111 in input bay 109 do not contain a sample. In some embodiments, each input rack received within input bay 109 of sample processing instrument 104 is configured to hold both a sample containing receptacle 105 and a processing receptacle 103 that is configured differently than the sample containing receptacle 105. In such embodiments, input rack 111 can be configured to hold multiple pairs of sample containing receptacles 105 and processing receptacles 103, such that sample containing receptacles 105 and processing receptacles 103 are incorporated in a one-to-one ratio and in an alternating fashion as shown in FIG. 1. In such embodiments, the user, after verifying instrument consumable levels, can begin sample processing by simply inserting input rack 111 holding pairs of sample containing receptacles 105 and processing receptacles 103 into input bay 109 of the automated instrument 104.

In some embodiments, receptacle gripper 119 and robotic arm 117 of processing instrument 104 are configured to couple receptacles 103 with respective carriers 101. And in some embodiments, receptacle gripper 119 and robotic arm 117 are configured to place receptacles 103 and the corresponding coupled carriers 101 onto intermediate conveyor assembly 106.

In some embodiments, receptacle gripper 119 and robotic arm 117 are configured to place receptacles 103 onto output racks 115. Once processing receptacles 103 are placed on output rack 115, a user can retrieve output rack 115 to run assay(s) on the contents of the processing receptacles 103 using an assay instrument (coupled or uncoupled to host conveyor assembly 102). In some embodiments, output rack 115 is configured to be operable in an assay instrument 108 that performs the assay, for example, an assay instrument configured to perform molecular assays. For example, in some embodiments, output rack 115 of processing instrument 104 functions as an input rack for an assay instrument 108. In such embodiments, the user removes rack 115 holding processed samples in processing receptacles 103 from the automated processing instrument 104, and inserts rack 115 in the input bay of an automated assay instrument 108, for example, a molecular assay instrument that performs a desired assay. In other embodiments, processing receptacles 103 in output rack 115 are manually transferred to an input rack configured to be operable in an automated assay instrument 108, for example, a molecular assay instrument that performs a desired assay.

In some embodiments, processing instrument 104 places matching machine readable labels (such as barcodes) on both a paired sample containing receptacle 105 and processing receptacle 103. In some embodiments, sample processing instrument 104 includes an onboard barcode reader 127 configured to read barcodes on sample containing receptacle 105 or processing receptacle 103 placed in sample processing station 107.

In some embodiments, sample processing instrument 104 includes one or more robotic arms 117 configured to translate in the X, Y, and Z planes within the automated instrument. In some embodiments, one robotic arm includes receptacle gripper 119 and is configured to transport sample containing receptacles 105 and processing receptacles 103 within sample processing instrument 104, for example, between input racks 111, sample processing station 107, output racks 115, and intermediate conveyor assembly 106. For example, sample processing instrument 104 can include one robotic arm 117 and one receptacle gripper 119 configured to transport sample containing receptacles 105 and processing receptacles 103. In other embodiments, sample processing instrument 104 includes more than one robotic arm 117 and more than one receptacle gripper 119 configured to transport sample containing receptacles 105 and processing receptacles 103 within the housing of instrument 104. In some embodiments, robotic arm 117 is any one of the robotic arm embodiments described in U.S. application Ser. No. 13/608,876, filed Sep. 10, 2012.

In some embodiments, robotic arm 117, which includes gripper 119, also includes a pipettor 121 configured to aspirate and dispense sample material. In some embodiments, pipettor 121 is an air-based pipettor configured to aspirate a sample from sample containing receptacles 105 or a reagent from a reagent containing receptacle and dispense the sample or reagent into a processing receptacle 103.

In some embodiments, processing instrument 104 includes at least two separate robotic arms 117. One robotic arm 117 can include pipettor 121 for transferring samples, and the other robotic arm 117 can include gripper 119 for transporting sample containing receptacles 105 and processing receptacles 103.

In some embodiments, receptacle gripper 130 is configured to pick-and-place sample containing receptacles 105 and processing receptacles 103 within sample processing instrument 104.

In some embodiments, samples are transferred from sample containing receptacles 105 to processing receptacles 103 in a serial fashion. For example, pipettor 121 is configured to take an aliquot of a sample from one sample containing receptacle 105 and transfer the aliquot to a processing receptacle 103. Thereafter pipettor 121 is configured to take another aliquot of a different sample from a different sample containing receptacle 105 and transfer the aliquot to another, different processing receptacle 103. An exemplary process for transferring and processing the sample, for example, at sample processing station 107, is described in detail below.

In some embodiments, sample processing instrument 104 is configured to add a reagent to a sample and/or incubate the sample as part of the sample processing.

In some embodiments, a receptacle gripper 119 of robotic arm 117 will transport processing receptacles 103 to incubator 123, for example, after completion of processing in sample processing station 107. After incubation is complete, receptacle gripper 119 of robotic arm 117 will transport processing receptacles 103 from incubator 123 to a carrier 101 positioned within instrument 104 or to an output rack 115.

In some embodiments, receptacle gripper 119 performs all pick and place duties required by sample processing instrument 104. In some embodiments, receptacle gripper 119 is programmed, by way of the controller, to perform one or more of the following steps: (1) transport processing receptacles 103 and sample containing receptacles 105 between, for example, input racks 111 and sample processing station 107, (2) transport sample containing receptacles 105 from sample processing station 107 to input racks 111, (3) transport processing receptacles 103 from processing station 107 to incubator 123, (4) transport processing receptacles 103 from processing station 107 to be coupled with carriers 101, and (5) transport processing receptacles 103 from the one or more incubators 123 to be coupled with carriers 101. In some embodiments, sample processing instrument 104 uses multiple receptacle grippers 117 to perform the above steps, which can maximize throughput and permits uninterrupted processing in sample processing station 107.

Figure 21:
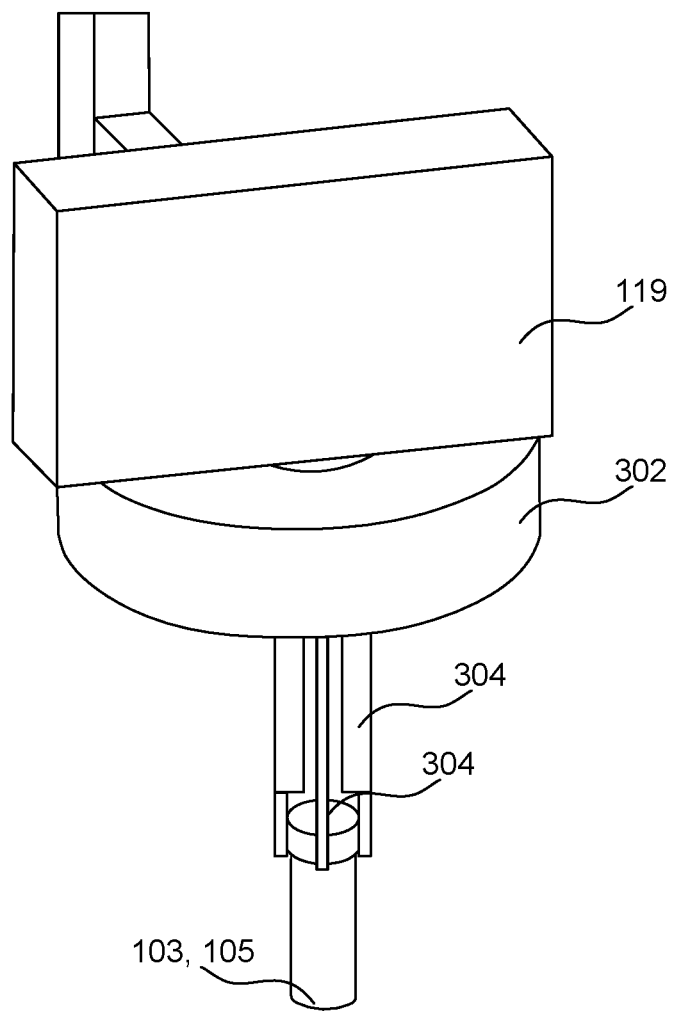
FIG. 21 is a perspective view of a receptacle gripper according to an embodiment.

FIG. 21 illustrates a receptacle gripper 119 of robotic arm 117 of processing instrument 104 according to one embodiment. As shown in FIG. 21, receptacle gripper 119 includes a chuck 302 that is configured to selectively grasp a portion, for example a cap, of a sample containing receptacle 105 or a processing receptacle 103. Chuck 302 can include a plurality of prongs 304 (for example, three prongs 304 as shown in FIG. 21) that are configured to move radially inward to grasp a cap of either a sample containing receptacle 105 or a processing receptacle 103, and radially outward to release the sample containing receptacle 105 or a processing receptacle 103.

Ensuring sample identification accuracy is another problem encountered when automating a sample processing process. For example, as the sample is prepared it is transferred between a sample containing receptacle 105 and a processing receptacle 103. Therefore, it is important to ensure that the sample in processing receptacle 103 is correlated with the sample in sample containing receptacle 105 so that the sample is processed according to the proper protocol and that the correlation of that sample with the donor patient is maintained. Accordingly, in some embodiments, system 100 tracks the identification of each sample throughout processing, including processing within instrument 104, following the sample as it is transferred from sample containing receptacle 105 to processing receptacle 103 and subsequent handling by host conveyor assembly 102 and processing by one or more assay instruments 108. One exemplary method of tracking this information within system 100, including within instrument 104, is to utilize matching barcodes on both sample containing receptacle 105 and processing receptacle 103. This process maintains sample-to-result positive identification tracking. In some embodiments, a user, for example, a laboratory, prints one barcode containing patient identification and applies it to sample containing receptacle 105. Processing receptacle 103, in turn, contains no label, a blank label, or a different label. Sample processing instrument 104, for example, using barcode reader 127, then reads the barcode of sample containing receptacle 105, transfers (for example, using a writer 131) information from the read barcode, for example, an identifier, to at least one of processing receptacle 103 or the corresponding carrier 101 coupled to the processing receptacle 103.

In some embodiments, writer 131 is a printer that prints the same barcode as contained on sample containing receptacle 105 (with optional additional metadata in the form of barcode prefixes, suffixes, or similar metadata) and applies the barcode to processing receptacle 103 and/or carrier 101. In some embodiments, the printer is any one of the printer embodiments described in U.S. application Ser. No. 14/919,467, filed Oct. 21, 2015. In some embodiments, sample processing instrument 104 reads the barcode of sample containing receptacle 105, and writer 131 creates the same barcode (with optional additional metadata in the form of barcode prefixes, suffixes, or similar metadata) directly on processing receptacle 103 and/or carrier 101, for example, by way of printing, imprint, burning, thermal transfer, or another method. Also in some embodiments, a different bar code is printed on processing receptacle 103 or carrier 101 containing additional metadata (e.g., time, volume, type, reagents, errors, etc.) related to the processing of the corresponding sample.

In some embodiments, writer 131 is an RFID writer configured to transfer information, including for example, an identifier, to an RFID tag on processing receptacle 103, carrier 101, or both. In such embodiments, the RFID tag on processing receptacle 103 or carrier 101 can be passive (e.g., a microchip attached to an antenna) or active (e.g., active transponders or beacons) RFID tags. Exemplary passive RFID tags can operate at low, high, or ultra-high frequency. Low frequency passive RFID tags can operate, for example, at 124 kHz, 125 kHz, or 135 kHz. High frequency passive RFID tags can operate, for example, at 13.56 MHz. And ultra-high frequency passive RFID tags can operate, for example, at a range from 860 MHz to 960 MHz. In some embodiments, the passive RFID tag operates at 2.45 GHz. In some embodiments, RFID writer 131 transfers information obtained from the barcode on sample containing receptacle 105 (with optional additional metadata in the form of barcode prefixes, suffixes, or similar metadata) to the RFID tag on receptacle 103 and/or carrier 101. Also in some embodiments, RFID writer 131 transfers information different than information found on the barcode on sample containing receptacle 105 (e.g., time, volume, type, reagents, errors, etc.) related to the processing of the corresponding sample within instrument 104.

In some embodiments, writer 131 includes both an RFID writer module and a printer module as described above.

In some embodiments, instrument 104 does not include writer 131. Instead, instrument 104 includes an RFID reader configured to read information, for example, an identifier, from an RFID tag on either carrier 101 or processing receptacle 103. Automated sample processing instrument 104 reads both the barcode on sample containing receptacle 105 creates an association between (1) the sample containing receptacle 105 from which a sample was taken and (2) the read identifier of the RFID tag on the carrier 101 or receptacle 103 in which a portion of the sample was dispensed. This association information is then transferred to a laboratory information system via a network connection (e.g., LAN, Ethernet, WiFi, Bluetooth®, ZigBee®, RS232, USB, RF, IR, Firewire®, Thunderbolt®, eSATA, or other network connection).

As explained below, when system 100 encounters carriers 101 and processing receptacles 103 with information, for example, an identifier, associated with various positions within system 100, system 100 handles carriers 101 and processes receptacles 103 accordingly.

In some embodiment, receptacle gripper 119 retrieves sample containing receptacle 105 and processing receptacle 103 from input rack 111. Both receptacles 103 and 105 are transported to sample processing station 107 where, for example, the barcodes of receptacles 103 or 105 passed through a field of view of barcode reader 127 to be read and verified to be a corresponding pair. In such an embodiment, processing receptacle 103 can be transported to the writer 131, for example, a printer or RFID writer, by receptacle gripper 119 of robotic arm 117 to print a barcode or transfer information to an RFID tag on processing receptacle 103 before receptacle 103 is transported to sample processing station 107. The barcode printed on, or otherwise applied, or information transferred to processing receptacle 103 may be identical to the information on the barcode on corresponding sample containing receptacle 105, or it may be a different barcode. In some embodiments, a different bar code is printed on or different information is transferred to processing receptacle 103 that encodes additional metadata relevant to the processing of that particular sample.

In some embodiment, once processing has been completed, gripper 119 of robotic arm 117 transports processing receptacle 103 to a carrier 101, and transports sample containing receptacle 105 back to input rack 111. For example, if carrier 101 is a puck defining a recess, gripper 119 can insert a portion of processing receptacle 103 into the recess defined by the carrier 101, thereby coupling processing receptacle 103 to carrier 101. Then in some embodiments, gripper 119 or another device (e.g., another robotic arm or conveyor assembly) transports receptacle 103 and the respective carrier 101 to intermediate conveyor assembly 106.

In some embodiments, the automated processing instrument 104 is a high-throughput, random access sample processing instrument 104 capable of simultaneously processing multiple different sample types. As indicated, the instrument automatically processes samples according to a rule set that balances throughput with time-to-next-result, which is particularly relevant when the instrument is processing different types of samples that require different routines and reagents. For example, in one embodiment, instrument 104 is designed to process up to about 540 samples that do not require incubation, or up to about 360 samples that require reagent addition and heated incubation within a single eight hour shift. Included in this time is instrument setup, run preparation, sample processing, clean up and instrument power down. For purposes of this discussion, a "run" is defined as the processing of up to about sixty samples, for example, LCB specimens, from start to finish. In other embodiments, a run can include processing more or less than sixty samples, depending on the number of available input lanes in the input bay 109 and output lanes in the output bay of the machine. For example, a run could refer to the processing of up to about ninety-six samples, for example, LCB specimens, from start to finish. In one embodiment, a run refers to processing a collection of samples that occupy a defined portion or all of the available input lanes of the input bay 109 or that occupy a defined portion or all of the available output lanes of the output bay.

In some embodiments, instrument 104 is configured to perform one or more of the following processes (for example, when processing a ThinPrep® sample):

1. Using robotic arm 117 having receptacle gripper 119, pick sample containing receptacle 105 from input rack 111 and place in a corresponding container holster on a carousel in processing station 107;
2. Read a barcode on sample containing receptacle 105 using barcode reader 127;
3. Orbital mix the sample in sample containing receptacle 105 using processing station 107;
4. If necessary, using robotic arm 117 having receptacle gripper 119, pick corresponding processing receptacle 103 from input rack 111 and place in the printer for printing a barcode (or other machine readable label) on processing receptacle 103;
5. Using robotic arm 117 having receptacle gripper 119, pick corresponding processing receptacle 103 from the printer and place in a processing receptacle holster on a carousel in processing station 107;
6. Uncap the sample containing receptacle 105 using a capping/decapping mechanism 201 at the sample processing station 107;
7. Using pipettor 121, aspirate at least a portion of a sample from sample containing receptacle 105;
8. Recap sample containing receptacle 105 using a capping/decapping mechanism 201;
9. Uncap the processing receptacle 103 using a capping/decapping mechanism 201 at the sample processing station 107;
10. Using pipettor 121, dispense the aspirated portion of the sample into processing receptacle 103;
11. Recap the processing receptacle 103 using the capping/decapping mechanism 201 at the sample processing station 107;
12. Using robotic arm 117 with receptacle gripper 119, transport sample containing receptacle 105 to input rack 111;
13. Using robotic arm 117 with receptacle gripper 119, couple processing receptacle 103 with a carrier 101 (for example, by inserting a portion of processing receptacle 103 within a recess defined by carrier 101); and
14. Using robotic arm 117 with receptacle gripper 119, transport processing receptacle 103 coupled to carrier 101 to intermediate conveyor assembly 106.
15. Alternatively, using robotic arm 117 with receptacle gripper 119, transport processing receptacle 103 to output rack 115.

In some embodiments, processing instrument 104 is configured to perform one or more of the following processes (for example, when processing a SurePath® sample):

1. Using robotic arm 117 having receptacle gripper 119, pick sample containing receptacle 105 from input rack 111 and place in a corresponding container holster on a carousel in processing station 107;
2. Read a barcode on sample containing receptacle 105 using barcode reader 127;
3. Orbital mix the sample in sample containing receptacle 105 using processing station 107;
4. If necessary, using robotic arm 117 having receptacle gripper 119, pick corresponding processing receptacle 103 from input rack 111 and place in the printer for printing a barcode (or other machine readable label) on processing receptacle 103;
5. Using robotic arm 117 having receptacle gripper 119, pick corresponding processing receptacle 103 from the printer and place in a processing receptacle holster on a carousel in processing station 107;

6. Uncap the sample containing receptacle 105 using a capping/decapping mechanism 201 at the sample processing station 107;
7. Using pipettor 121, aspirate a predetermined amount of a sample processing reagent (e.g., Fast Express reagent, available from Hologic, Inc., Bedford, Mass.) from a reagent containing receptacle within instrument 104;
8. Using pipettor 121, aspirate at least a portion of a sample from sample containing receptacle 105;
9. Recap sample containing receptacle 105 using a capping/decapping mechanism 201;
10. Uncap the processing receptacle 103 using a capping/decapping mechanism 201 at the sample processing station 107;
11. Using pipettor 121, dispense the aspirated portion of the sample into processing receptacle 103;
12. Recap the processing receptacle 103 using the capping/decapping mechanism 201 at the sample processing station 107;
13. Using robotic arm 117 with receptacle gripper 119, transport sample containing receptacle 105 to input rack 111;
14. Optionally, mixing processing receptacle 103;
15. Using robotic arm 117 with receptacle gripper 119, transport processing receptacle 103 to output rack 115, or incubator 123 for incubation;
16. If processing receptacle 103 is positioned in incubator 123, using robotic arm 117 with receptacle gripper 119, either transport processing receptacle 103 from incubator 123 to output rack 115 after incubation or couple processing receptacle 103 with a carrier 101 (for example, by inserting a portion of processing receptacle 103 within a recess defined by carrier 101); and
16. If receptacle 103 is coupled to carrier 101, using robotic arm 117 with receptacle gripper 119, transport processing receptacle 103 coupled to carrier 101 to intermediate conveyor assembly 106.

In some embodiments, one or more of the above processes can occur simultaneously. The above automated protocols are provided by way of example only such that modifications of the number of steps, what happens in each step, and the number of processes occurring in a particular order or simultaneously may be changed or altered without affecting the subject matter of this disclosure. One of skill in the art would appreciate that the processing time required to process each sample has a direct effect on the number of samples that can be prepared in a given time period. Manipulation of the processing time may have a detrimental impact on processing accuracy and can increase the risk of contamination, though a variety of sample processing times are contemplated with the caveat that downtime between sample processing is kept to a minimum.

B. Exemplary Embodiments of Intermediate Conveyor Assembly 106

As shown in FIG. 2, intermediate conveyor assembly 106 is configured to transport a plurality of carriers 101 from a position 136 to a position 135. In some embodiments, position 136 is within a housing of sample processing instrument 104, and position 135 is outside the housing of processing instrument 104. Intermediate conveyor assembly 106 is configured to transport carriers 101 that are each coupled a processing receptacle 103. In some embodiments, processing receptacles 103 coupled to carriers 101 each contain a sample portion dispensed by an automated pipettor 121 of sample processing instrument 104 and processed according to any one of the above identified processes of sample processing instrument 104.

In some embodiments, intermediate conveyor assembly 106 defines a single path along which carriers 101 move as shown in FIG. 2. In other embodiments, intermediate conveyor assembly 106 defines two or more paths along which carriers 101 move. In some embodiments, intermediate conveyor assembly 106 includes a movable track that defines the path along which carriers 101 move. In some track embodiments, the track can be a unitary belt or a plurality of links coupled to form a belt. In such track embodiments, carriers 101 sit on the track(s) and move as the track(s) move, for example, in the direction of the annotated arrow in FIG. 2. In other embodiments (not shown), intermediate conveyor assembly 106 includes a movable gripper that defines the path along which carriers 101 move. For example, the gripper can grasp a carrier 101 or a processing receptacle 103 coupled to carrier 101 and move in the direction of the annotated arrow in FIG. 2.

Intermediate conveyor assembly 106 is configured to transfer carriers 101 to host conveyor assembly 102. For example, in some embodiments, intermediate conveyor assembly 106 includes a diverter 140 configured to transfer a carrier 101 located at position 135 to host conveyor assembly 102. In some embodiments, diverter 140 is a rotatable disc that defines one or more recesses (for example, three recesses as shown in FIG. 2) configured to receive a carrier 101 at position 135. As diverter 140 rotates, carrier 101 received within the recess defined by diverter 140 is transferred to host conveyor assembly 102. In some embodiments, diverter 140 is configured to rotate in one direction or in two directions about an axis of rotation.

C. Exemplary Embodiments of Host Conveyor Assembly 102

Host conveyor assembly 102 is configured to transport a plurality of carriers 101 along a path. In some embodiments, this path transports carriers 101 between positions adjacent processing instrument 104 and assay instruments 108a-108c. The path defined by host conveyor assembly 102 can have various shapes based on the placement of processing instrument 104 and assay instruments 108a-108c. For example, as shown in FIG. 2, the path defined by host conveyor assembly 102 is substantially rectangular. But in other embodiments, the path defined by host conveyor assembly 102 can have non-rectangular shapes such as an L-shape or a circular shape. As shown in FIG. 2, host conveyor assembly 102 includes a first portion 118 configured to transport carriers 101 in a first direction as indicated by the annotated arrows, and a second portion 120 configured to transport carriers 101 in a second direction, opposite the direction of first portion 118, as indicated by the annotated arrows pointing in the opposite direction. In some embodiments, first portion 118 and second portion 120 are linear as shown in FIG. 2.

In some embodiments, the first portion 118 includes one or more movable tracks that define the path along which carriers 101 move in the first direction. In some embodiments, the first portion 118 includes a single track that defines the path along which carriers 101 move. In some track embodiments, the track(s) of first portion 118 can be unitary belts or a plurality of links coupled to form one or more belts. In such track embodiments, carriers 101 sit on the track(s) of first portion 118 and move as the track(s) move. In other embodiments, host conveyor assembly 102 includes a movable gripper that defines the path along which carriers 101 move along first portion 118.

In some embodiments, the second portion 120 includes one or more movable tracks that define the path along which carriers 101 move in the first direction. In some embodiments, the second portion 120 includes a single track that defines the path along which carriers 101 move. In some track embodiments, the track(s) of second portion 120 can be unitary belts or a plurality of links coupled to form one or more belts. In such track embodiments, carriers 101 sit on the track(s) of second portion 120 and move as the track(s) move. In other embodiments, host conveyor assembly 102 includes a movable gripper that defines the path along which carriers 101 move along second portion 120.

Host conveyor assembly 102 can include one or more drive assemblies (not shown in FIG. 2) configured to move the drive elements (for example, movable tracks or grippers) of first and second portions 118 and 120 of host conveyor assembly 102. In some embodiments, a single drive assembly moves both the drive elements of first and second portions 118 and 120 of host conveyor assembly 102.

In some embodiments, host conveyor includes a diverter 122 configured to transfer carriers 101 from first portion 118 to second portion 120. In some embodiments, diverter 122 is a rotatable disc that defines one or more recesses (for example, one recess as shown in FIG. 2) configured to receive a carrier 101 on the first portion 118 of host conveyor assembly 102. As diverter 122 rotates, the carrier 101 received within the recess defined by diverter 122 is transferred to second portion 120 of host conveyor assembly 102. In some embodiments, diverter 140 is configured to rotate in one direction or in two directions about an axis of rotation. In some embodiments, host conveyor assembly 102 includes a sensor 126 configured to detect the presence of a carrier 101 at a position in which the carrier 101 is received within the recess of diverter 122. In some embodiments, diverter 122 is operably coupled to sensor 126 such that when a carrier 101 is detected to be within the recess defined by diverter 122, rotation of diverter 122 is actuated and the carrier 101 is transferred to second portion 120 of host conveyor assembly 102. In some embodiments, diverter 122 is located at a terminal end portion of first portion 118, and at a beginning end portion of second portion 120. In other embodiments, diverter 122 is positioned at non-terminal or beginning ends of first and second portions 118 and 120 of host conveyor assembly 102.

In some embodiments, host conveyor assembly 102 includes another diverter 124 configured to transfer carriers 101 from second portion 120 to first portion 118. In some embodiments, diverter 124 is a rotatable disc that defines one or more recesses (for example, one recess as shown in FIG. 2) configured to receive a carrier 101 on the second portion 120 of host conveyor assembly 102. As diverter 124 rotates, the carrier 101 received within the recess defined by diverter 124 is transferred to first portion 118 of host conveyor assembly 102. In some embodiments, diverter 124 is configured to rotate in one direction or in two directions about an axis of rotation. In some embodiments, host conveyor assembly 102 includes a sensor 128 configured to detect the presence of a carrier 101 at a position in which the carrier 101 is received within the recess of diverter 124. In some embodiments, diverter 124 is operably coupled to sensor 128 such that when a carrier 101 is detected to be within the recess defined by diverter 122, rotation of diverter 124 is actuated and carrier 101 is transferred to first portion 118 of host conveyor assembly 102. In some embodiments, diverter 124 is located at a terminal end portion of second portion 120, and at a beginning end portion of first portion 118 of host conveyor assembly 102. In other embodiments, diverter 124 is positioned at non-terminal or beginning ends of second and first portions 120 and 118 of host conveyor assembly 102.

In some embodiments, one or more of assay instruments 108 and intermediate assay conveyor assemblies 133 are operatively coupled to first portion 118 of host conveyor assembly 102 (assay instruments 108a and 108b, and intermediate conveyor assemblies 133a and 133b as shown in FIG. 2), and one or more assay instruments 108 and respective intermediate conveyor assemblies 133 (assay instrument 108c and intermediate conveyor assembly 133c as shown in FIG. 2) are operative coupled to second portion 120 of host conveyor assembly 102, as shown in FIG. 2. In other embodiments (not shown in FIG. 2), none of assay instruments 108 and respective intermediate conveyor assemblies 133 are coupled to one of first and second portions 118 and 120 of host conveyor assembly 102.

In some embodiments, host conveyor assembly 102 is configured to transport carriers 101 to positions (for example, positions 141a, 141b, and 141c as shown in FIG. 2, collectively referred to as positions 141 or generically and individually as position 141) outside and adjacent respective assay instruments 108. In other embodiments (not shown), position 141 is inside the housing of respective assay instrument 108.

In some embodiments, at position 141, host conveyor assembly 102 is configured to transport a carrier 101 such that carrier 101 either bypasses respective assay instrument 108 or is transported to intermediate conveyor assembly 133. For example, referring to FIG. 2, host conveyor assembly 102 can be configured to transport a carrier 101 such that it bypasses respective assay instrument 108—the carrier 101 is never received by intermediate conveyor assembly 133—and is transported to a downstream portion 145 of host conveyor assembly 102 that transports the carrier 101 to a position (for example, downstream positions 141b, 141c, and 141a) adjacent another assay instrument 108 operatively coupled to host conveyor assembly 102. As for another example, host conveyor assembly 102 can be configured to transport a carrier 101 such that it bypasses both assay instruments 108a and 108b—the carrier 101 is never received by intermediate assay conveyor assemblies 133a and 133b—and is transported to a position (for example, position 141c) adjacent assay instrument 108c. Or at position 141, host conveyor assembly 102 is configured to transport carrier 101 to intermediate conveyor assembly 133 such that carrier 101 is transported to assay instrument 108.

In some embodiments, host conveyor assembly 102 includes a diverter (for example, diverters 142a, 142b, and 142c, collectively referred to as diverters 142 or individually and generically referred to as diverter 142) adjacent position 141 and a respective intermediate conveyor assembly 133. Diverter 142 is configured to selectively transport a carrier 101 (one at a time in some embodiments) from a portion (first portion 118 or second portion 120) of host conveyor assembly 102 to intermediate conveyor assembly 133 (for example, intermediate assay conveyor assemblies 133a, 133b, or 133c) based on information (e.g., an identifier) on the carrier 101, the processing receptacle 103 coupled to the carrier 101, or both the carrier 101 and receptacle 103. In some embodiments, diverter 142 is also configured to alternatively and selectively transfer a carrier 101 (one at a time in some embodiments) from position 141 on host conveyor assembly 102 to downstream portion 145 of host conveyor assembly 102 such that the carrier 101 bypasses the respective intermediate conveyor assembly 133 based on an information (e.g., an identifier) on the carrier 101, the processing receptacle 103 coupled to the carrier 101, or both the carrier 101 and receptacle 103.

In some embodiments, diverter 142 is a rotatable disc that defines one or more recesses (for example, one recess as shown in FIG. 2) configured to receive a carrier 101 at position 141 on an upstream portion of host conveyor assembly 102. As diverter 142 rotates, the carrier 101 received within the recess defined by diverter 142 is transferred to either intermediate conveyor assembly 133 (for example, if diverter 142 rotates counter clockwise) or to downstream portion 145 of host conveyor assembly 102 (for example, if diverter 142 rotates clockwise) such that the carrier bypasses the respective intermediate conveyor assembly 133 based on information (e.g., an identifier) on the carrier 101, the processing receptacle 103 coupled to the respective carrier 101, or both. For example, an upstream portion of host conveyor assembly 102 transports a carrier 101 such that it is received within a recess defined by diverter 142 at position 141. Then based on information (e.g., an identifier) on the carrier 101, the processing receptacle 103 coupled to the respective carrier 101, or both, diverter 142 rotates to a position that aligns the recess in which carrier 101 is received with either (1) downstream portion 145 of host conveyor assembly 102 (such that the carrier bypasses intermediate conveyor assembly 133 and assay instrument 108) or (2) a portion of intermediate conveyor assembly 133*a* such that the carrier can be subsequently transported to a processing position of assay instrument 108. In some embodiments, diverter 142 is configured to rotate in one direction or in two directions about an axis of rotation.

In some embodiments, host conveyor assembly 102 includes a sensor (for example, sensors 144*a*, 144*b*, and 144*c*, collectively referred to as sensors 144 or individually and generically as sensor 144) configured to read the information (e.g., an identifier) on the carrier 101, the processing receptacle 103 coupled to the respective carrier 101, or both. Sensor 144 can be positioned upstream from diverter 142. Diverter 142 is operatively coupled to sensor 144 such that diverter 142 selectively transfers a carrier 101 from an upstream portion of host conveyor assembly 102 to either (1) an intermediate conveyor assembly 133 or (2) a downstream portion 145 of host conveyor assembly 102 that bypasses intermediate conveyor assembly 133 and assay instrument 108 based on the information (e.g., an identifier) on the carrier 101, the processing receptacle 103 coupled to the respective carrier 101, or both read by sensor 144.

In some embodiments, system 100 includes a control system (not shown in FIG. 2) configured to transmit a control signal to diverter 142. Diverter 142 is configured to transfer the carrier 101 from the upstream portion of host conveyor assembly 102 to either (1) an intermediate conveyor assembly 133 or (2) a downstream portion 145 of host conveyor assembly 102 that bypasses intermediate conveyor assembly 133 and assay instrument 108 based on the control signal received from the control system. And sensor 144 can be configured to transmit a signal to the control system based on the read information (e.g., an identifier) of the carrier 101, the processing receptacle 103 coupled to the respective carrier 101, or both. The control system also can be configured to adjust the control signal transmitted to diverter 142 based on the sensor signal received from sensor 144 to control whether the carrier 101 is transported from an upstream portion of host conveyor assembly 102 to either (1) an intermediate conveyor assembly 133 or (2) a downstream portion 145 of host conveyor assembly 102 that bypasses intermediate conveyor assembly 133 and assay instrument 108.

In some embodiments, at least one of the carrier 101 and the respective processing receptacle 103 includes an RFID tag that transmits an identifier, and sensor 144 is an RFID antenna configured to detect the identifier transmitted by the RFID tag on the at least one of carrier 101 and processing receptacle 103. In other embodiments, at least one of the carrier 101 and the respective processing receptacle 103 includes a machine readable label, for example, a barcode, that includes an identifier, and sensor 144 is an image sensor, for example, a barcode reader, configured to detect the label on the at least one of carrier 101 and processing receptacle 103.

In some embodiments, each of sensors 144*a*, 144*b*, and 144*c* are the same type of sensor, and in other embodiments at least two of sensors 144*a*, 144*b*, and 144*c* are different types of sensors.

In some embodiments, the path defined by host conveyor assembly 102 is substantially enclosed by a cover (not shown). The cover can help prevent contamination of samples within receptacles 103 coupled to carriers 101 being transported on host conveyor assembly 102.

D. Exemplary Embodiments of Intermediate Conveyor Assemblies 133

Intermediate conveyor assembly 133 is configured to receive carriers 101 at position 141 on host conveyor assembly 102 and transport the carriers to a respective processing position (for example, processing positions 154*a*, 154*b*, 154*c*, collectively referred to as processing positions 154 or individually referred to as processing position 154) of the assay instrument 108. In some embodiments, position 154 is within a housing of the respective assay instrument 108. In some embodiments, assay instrument 108 includes an automated pipettor configured to aspirate at least a portion of a sample from a processing receptacle 103 coupled to a carrier 101 positioned at processing position 154. Automated pipettor 158 can also be configured to subsequently dispense the aspirated portion of the first sample from the processing receptacle 103 at processing position 154 into an assay receptacle 160. Automated pipettor 158 and assay instrument 108 are described further below.

In some embodiments, intermediate conveyor assembly 133 is also configured to transport a carrier 101 from processing position 154 to another position outside the housing of assay instrument 108 (for example, positions 167*a*, 167*b*, and 167*c*, collectively referred to as positions 167 or individually referred to as position 167). In other embodiments, intermediate conveyor assembly 133 is configured to transport a carrier 101 from processing position 154 to another position inside the housing of assay instrument 108. In some embodiments, intermediate conveyor assembly 133 is configured to transport a carrier 101, after being positioned at processing position 154, back to host conveyor assembly 102. For example, intermediate conveyor assembly 133 can be configured to transport a carrier 101 at a position outside of the housing of assay instrument 108 (for example, position 167 in FIG. 2), to host conveyor assembly 102.

In some embodiments, each of intermediate conveyor assemblies 133*a*-133*c* is configured similarly (e.g., similar components, shape, size, and path along which carriers 101 are transported) as shown in FIG. 2. In other embodiments, at least two of intermediate conveyor assemblies 133*a*-133*c* are configured differently (e.g., different components, shape, size, or path along which carriers 101 are transported).

In some embodiments, intermediate conveyor assembly 133 includes a buffer conveyor subassembly 114 and a spur conveyor subassembly 116. FIGS. 3-10 illustrate embodiments of buffer conveyor subassembly 114 and a spur conveyor subassembly 116, and are referenced collectively below in describing embodiments of buffer conveyor subassembly 114 and a spur conveyor subassembly 116.

Buffer conveyor subassembly 114 can include an input portion 146 configured to receive a carrier 101 from host conveyor assembly 102 (for example, by diverter 142) and transport the carrier 101 to a position 147. Buffer conveyor subassembly 114 can also include an output portion 162 configured to receive a carrier 101 at a position 163 from spur conveyor subassembly 116 and transport the carrier 101 to a position 167. In some embodiments, position 147, position 163, and position 167 are each outside the housing of assay instrument 108. In other embodiments, at least one of position 147, position 163, and position 167 are outside the housing of assay instrument 108. In some embodiments (not shown), position 147 is collocated with position 163—position 147 and position 163 are the same position.

Figure 6:
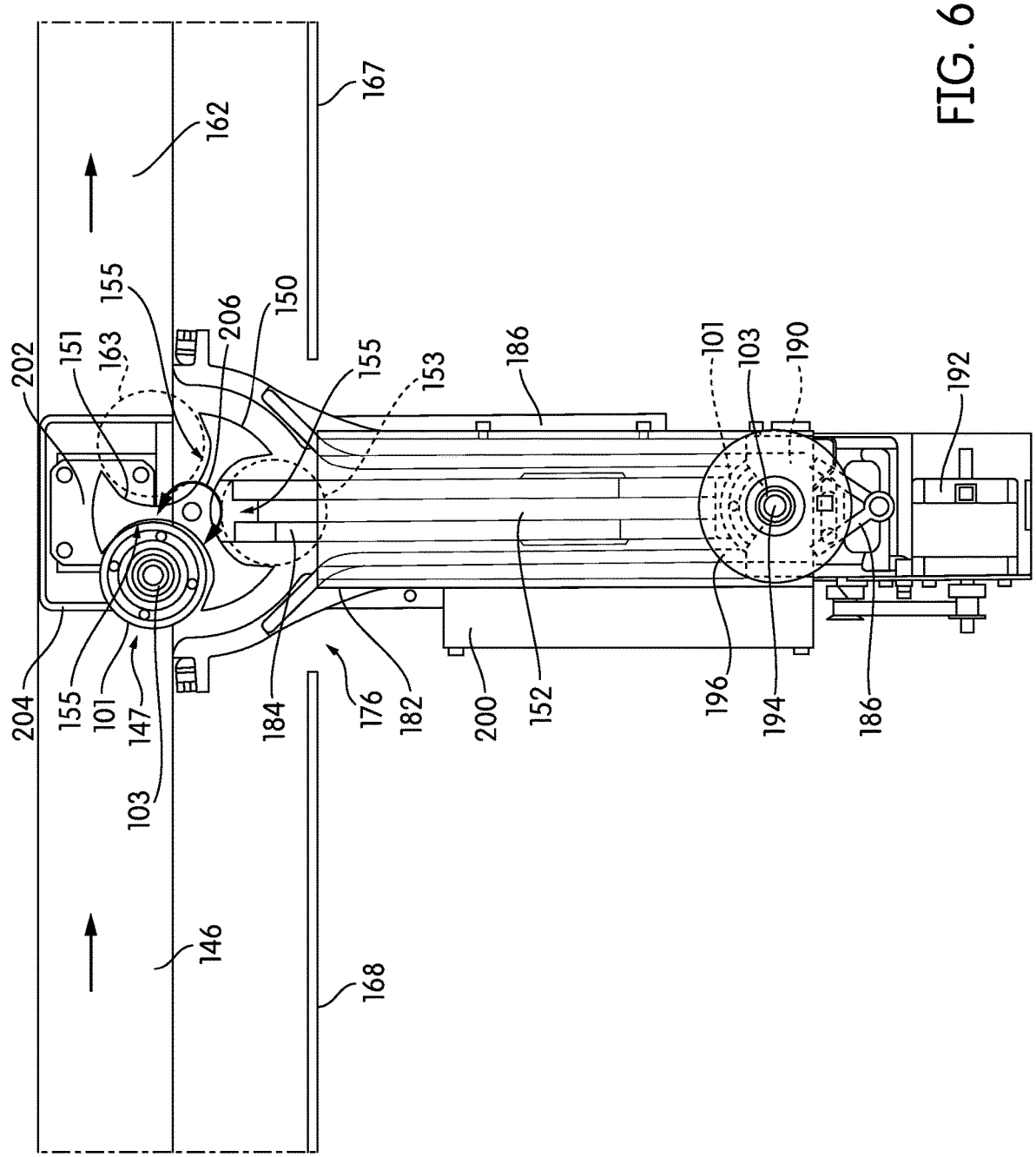
FIG. 6 is a plan view of a buffer conveyor subassembly and a spur conveyor subassembly of an intermediate conveyor assembly, according to an embodiment.

Spur conveyor subassembly 116 is configured to transport a carrier 101 between a position 153 and the processing position 154 within the housing of assay instrument 108. In some embodiments, position 153 is substantially outside the housing of assay instrument 108, as best seen in FIG. 2 and FIG. 6. In other embodiments (not shown), position 153 is inside the housing of assay instrument 108. In some embodiments, as shown, spur conveyor subassembly 116 is configured to receive only one carrier 101 at a time. In other embodiments (not shown), spur conveyor subassembly 116 is configured to receive more than one carrier 101 at a time.

Spur conveyor subassembly 116 can include a diverter 150 configured to transport a carrier 101 from position 147 on buffer conveyor subassembly 114 to position 153 on spur conveyor subassembly 116. And in some embodiments, diverter 150 is configured to transport a carrier 101 from position 147 to position 153 while simultaneously transporting another carrier 101 from position 153 to position 163 on buffer conveyor subassembly 114. Simultaneously transporting one carrier 101 from position 147 to position 153 while transporting another carrier 101 from position 153 to position 163 can increase throughput of spur conveyor subassembly 116 and, in turn, assay instrument 108.

Figure 4:
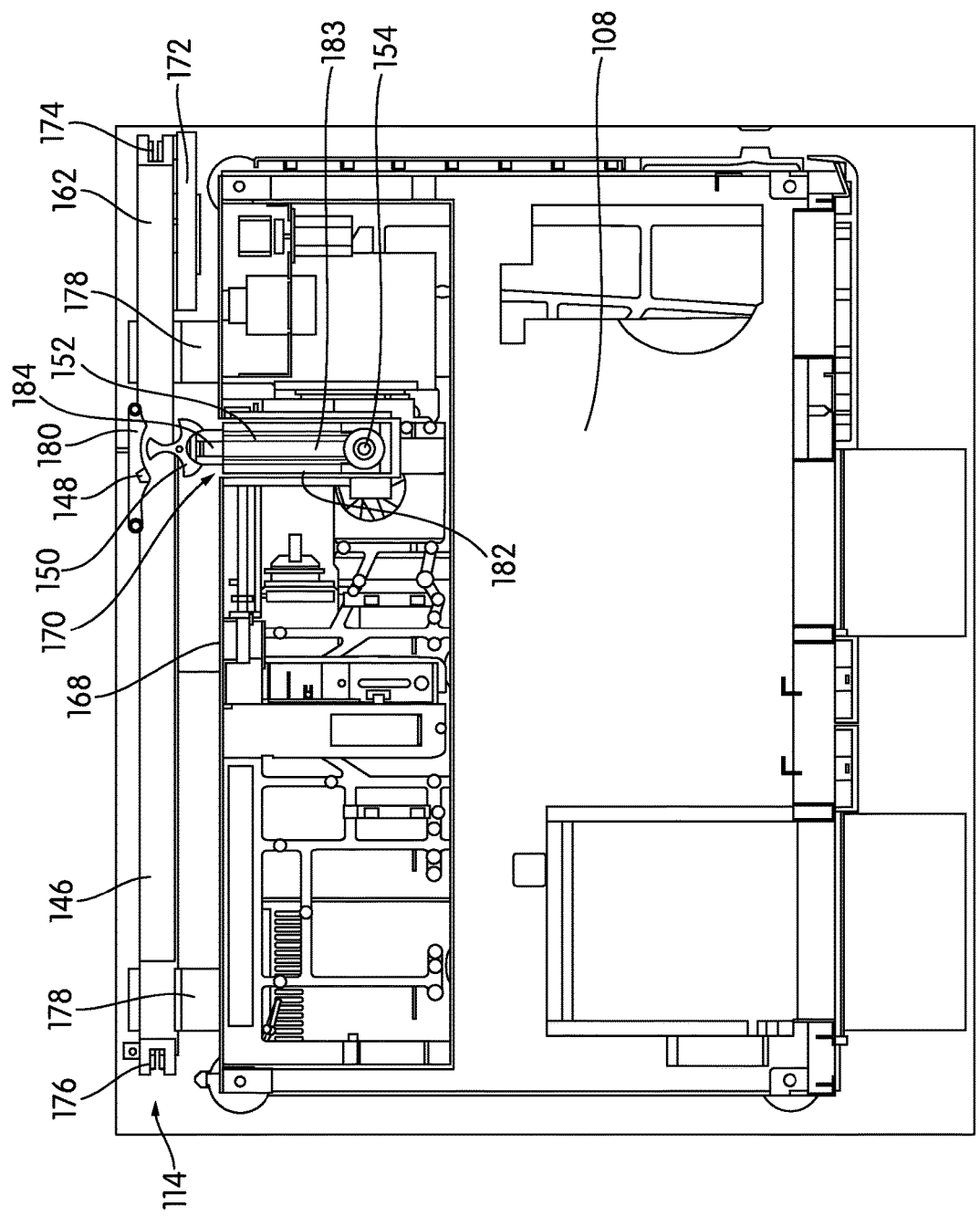
FIG. 4 is a cross-sectional plan view of an assay instrument and an intermediate conveyor assembly, according to an embodiment.
Figure 5:
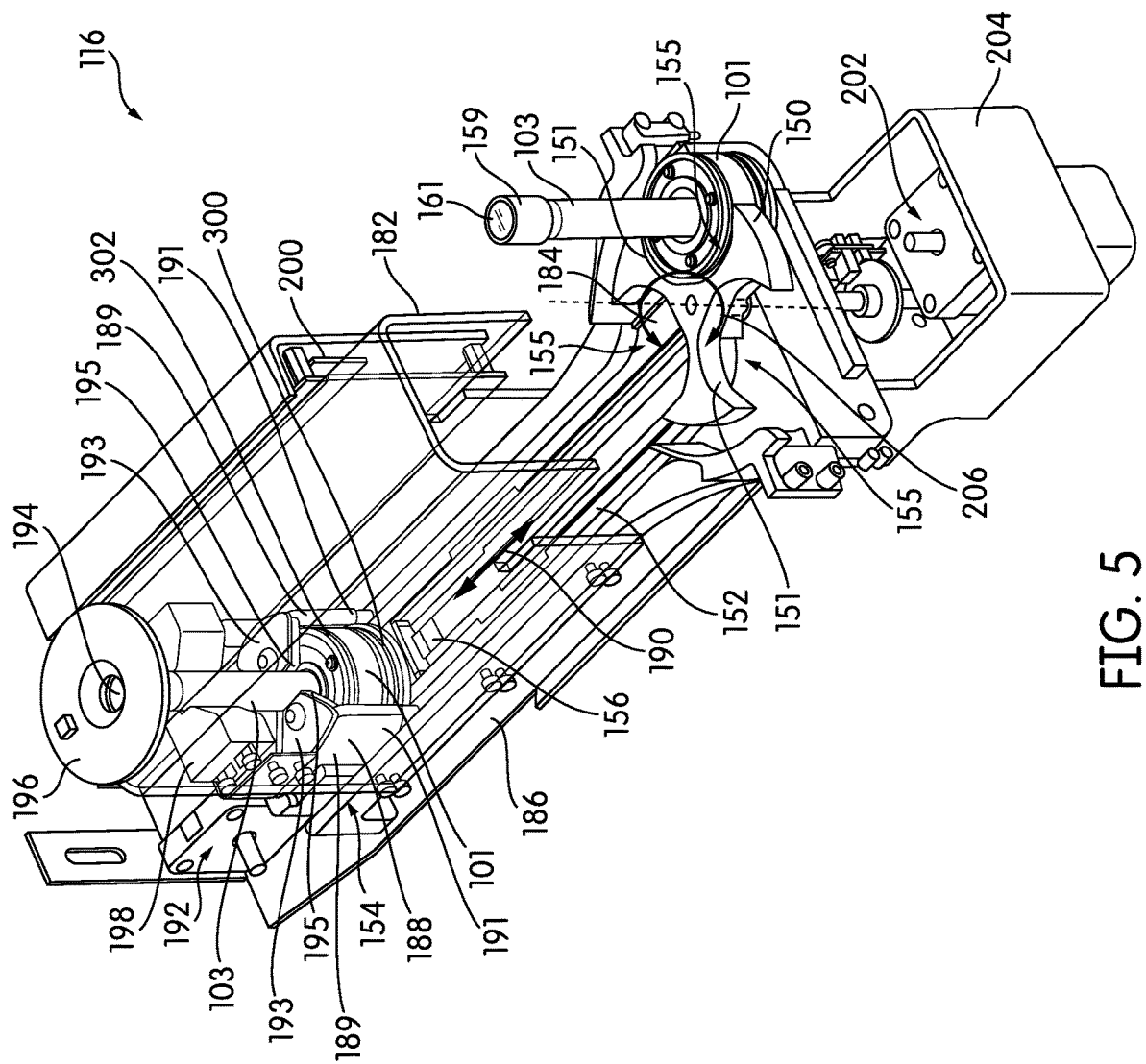
FIG. 5 is a perspective view of a spur conveyor subassembly of an intermediate conveyor assembly, according to an embodiment.

Diverter 150 can define a plurality of recesses for receiving and transporting carriers 101. For example, as best seen in FIGS. 5 and 6, diverter 150 can define three recesses 155, each configured to closely receive a carrier 101. In other embodiments, diverter 150 defines more than or less than three recesses 155. For example, diverter 150 can define one recess 155 or five recesses 155. In some embodiments, as illustrated, diverter 150 has a circular periphery with three concave, circular recesses 155. Recesses 155 can be evenly spaced around the periphery of diverter 150, as best seen in FIGS. 4 and 5. For example, if diverter 150 has three recesses 155, the recesses can be positioned about 120 degrees apart (about a center point of diverter 150).

In some embodiments, recesses 155 are positioned on diverter 150 such that when one recess 155 is aligned with position 147 on buffer conveyor subassembly 114, one recess 155 is aligned with position 153 spur conveyor subassembly 116, and one recess 155 is aligned with position 163 of buffer conveyor subassembly 114. Such a configuration allows diverter 150 to receive one carrier 101 at position 147 simultaneously with either (1) receiving or releasing another carrier 101 at position 153 or (2) releasing another carrier 101 at position 163. Accordingly, diverter 150 can transport a carrier 101 from position 147 to position 153 while simultaneously transporting another carrier 101 from position 153 to position 163.

As best seen in FIGS. 4 and 5, diverter 150 is configured to rotate about an axis of rotation. In some embodiments, diverter 150 is configured to rotate in one direction or in two directions.

Figure 22:
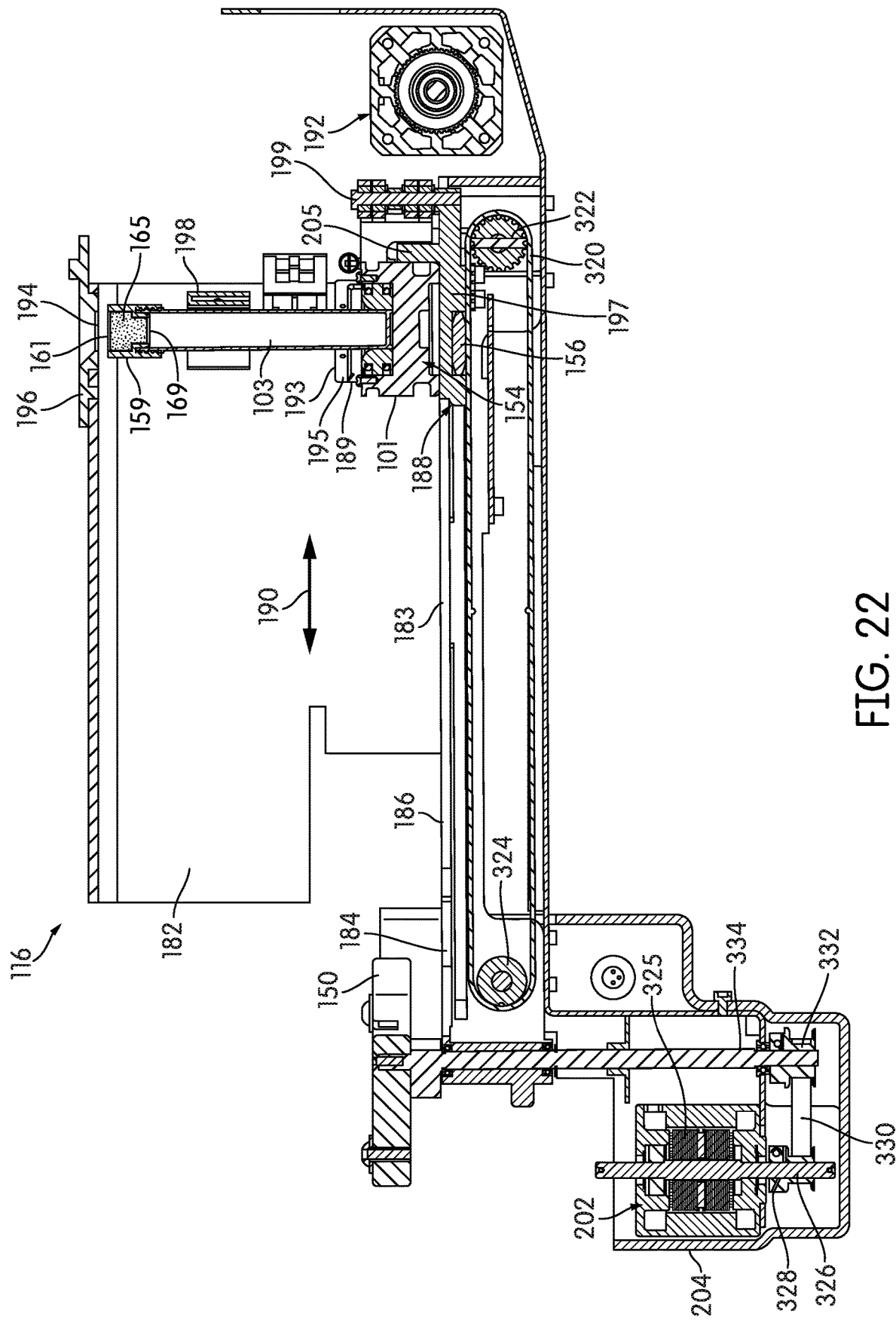
FIG. 22 is a cross-sectional view of a spur conveyor subassembly of an intermediate conveyor assembly, according to an embodiment.
Figure 23:
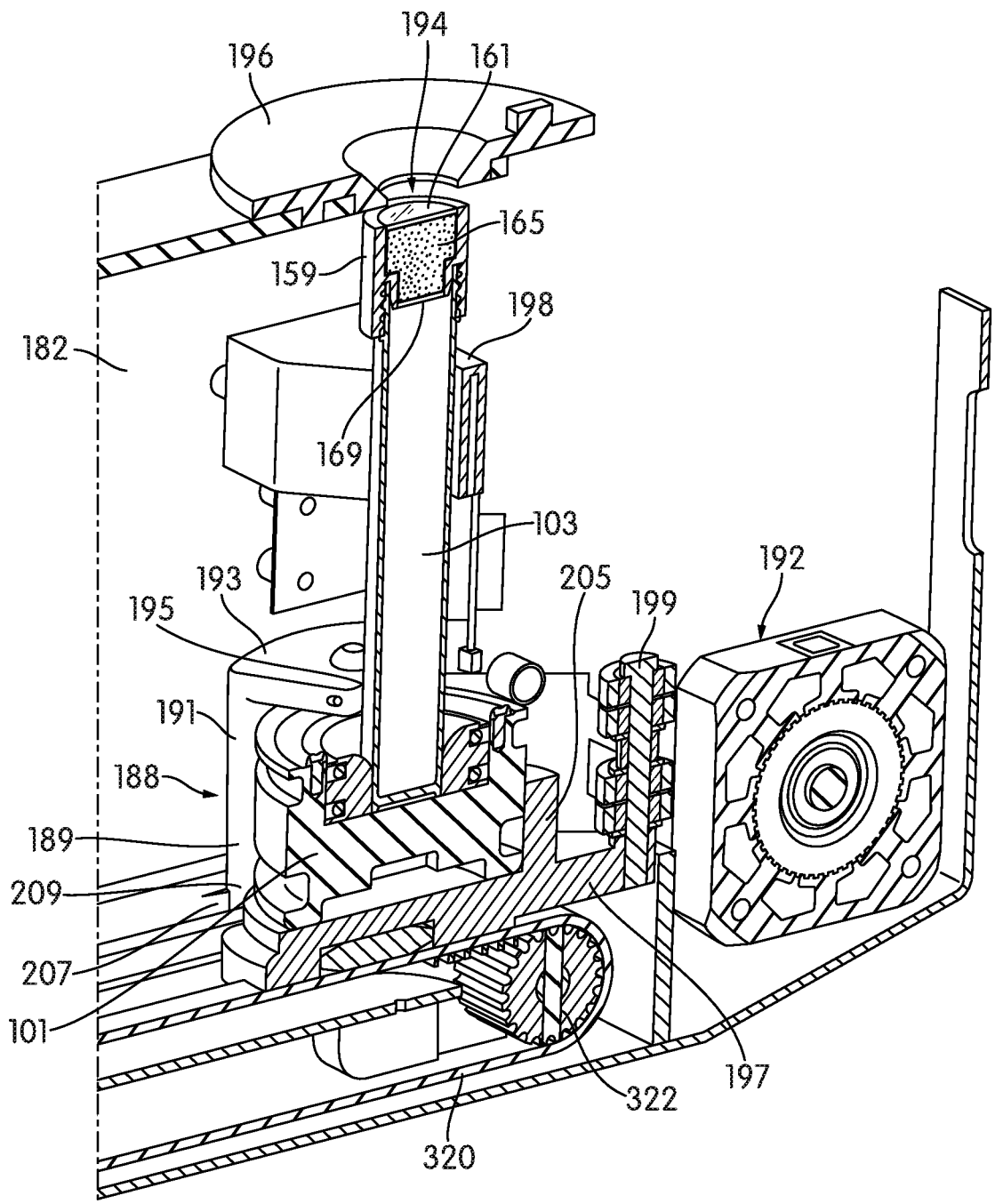
FIG. 23 is a cross-sectional view of a gripper of a spur conveyor subassembly at a subassembly at a processing position, according to an embodiment.

Spur conveyor subassembly 116 can include a drive assembly 202 that is operatively coupled to diverter 150 to selectively rotate diverter 150 about the axis of rotation. Drive assembly 202 can include a motor that is operatively coupled to an axle coupled to diverter 150 via, for example, one or more of gears, pulleys, and belts that drive the axle coupled to diverter 150. For example, referencing FIG. 22, drive assembly 202 can include a motor 325 that rotates a drive shaft 326 operatively coupled to motor 325. As shown in FIG. 22, drive shaft 326 is substantially vertical in some embodiments. Drive shaft 326 can include a pulley 328 operatively coupled to a drive belt 330. As shown in FIG. 22, drive belt 330 is substantially horizontal in some embodiments. Drive belt 330 is operative coupled to a pulley 332 fixedly connected to a rotating shaft 334. Rotating shaft 334 is substantially vertical, as shown in FIG. 22 in some embodiments. And diverter 150 is fixedly coupled to shaft 334. The motor of drive assembly 202 is selectively activated to rotate shaft 326 and pulley 328, which in turn rotates belt 330. As belt 330 rotates, pulley 332 and shaft 334 rotate, which in turn rotates diverter 150.

Figure 7:
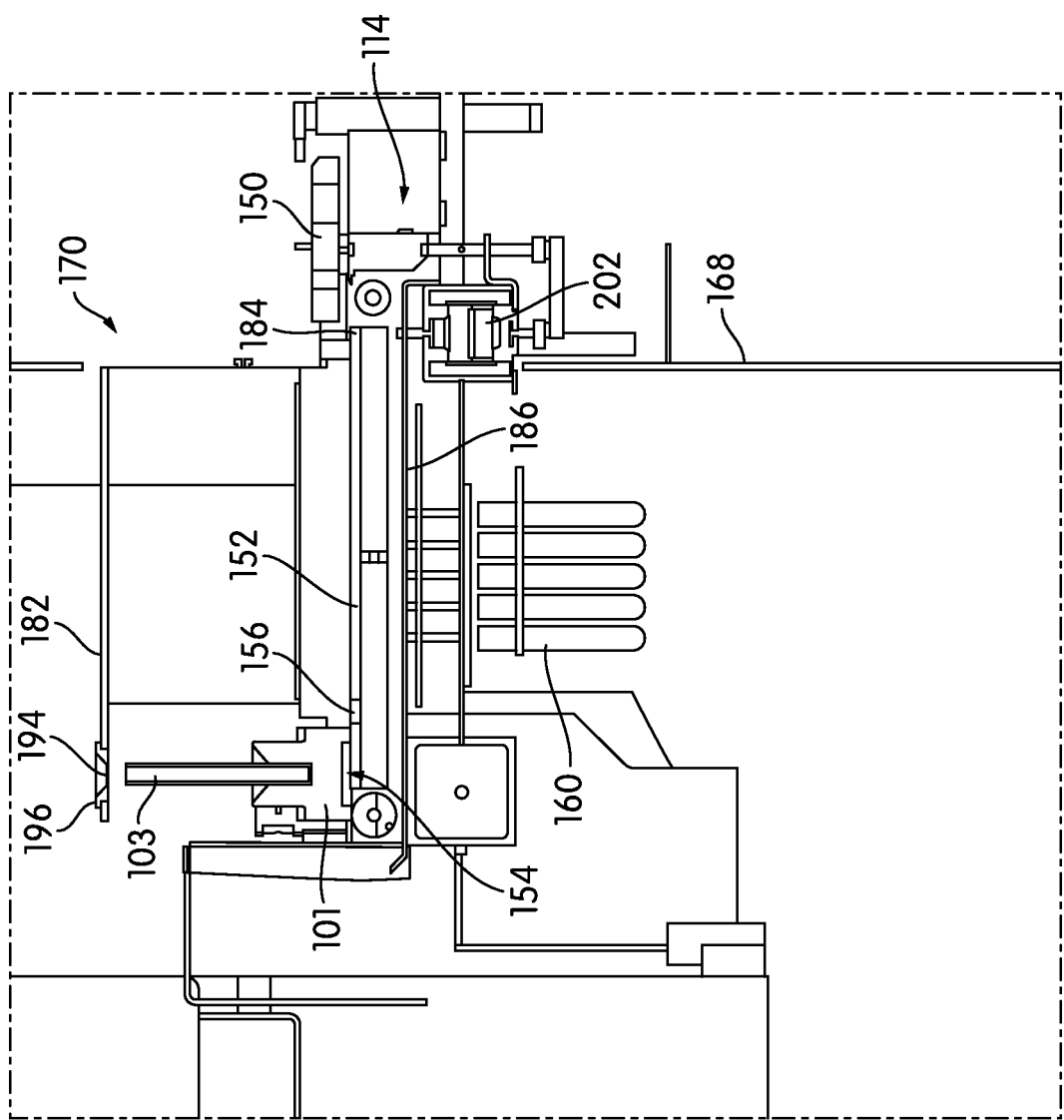
FIG. 7 is a cross-sectional side view of an assay instrument and an intermediate conveyor assembly, according to an embodiment.

In some embodiments, as best seen in FIG. 7, drive assembly 202 is positioned between a housing panel 168 of instrument 108 and a track of buffer conveyor subassembly 114. In some embodiments, the motor of drive assembly 202 is coupled to a mounting bracket 204 of spur conveyor subassembly 116. Mounting bracket 204 positions the motor of drive assembly 202 below diverter 150 in some embodiments as shown in FIGS. 5 and 7. As best seen in FIG. 22, mounting bracket 204 can enclose substantially the entire drive assembly 202 in some embodiments.

In some embodiments as best seen in FIGS. 3, 4, 6, 7, 9, and 10, buffer conveyor subassembly 114 includes a single movable track, and diverter 150 of spur conveyor subassembly 116 dissects the single movable track of buffer conveyor subassembly 114 into input portion 146 and output portion 162. In such embodiments, a portion of diverter 150 overlaps in a vertical direction at least a portion of the single movable track of buffer conveyor subassembly 114 input portion 146. In such embodiments, the single movable track of buffer conveyor subassembly 114 transports a carrier 101 received from host conveyor assembly 102 in the direction of the annotated arrows in FIGS. 2 and 10 along input portion 146, and diverter 150 stops the carrier 101 at position 147 if position 147 is unoccupied by another carrier 101. If position 147 is already occupied by a carrier 101, the subsequent carrier 101 being transported by input portion 146 is stopped by the carrier 101 at position 147.

In some embodiments, input portion 146 of buffer conveyor subassembly 114 has a length sufficient to queue a plurality of carriers 101 between diverter 150 and diverter 142a on host conveyor assembly 102. For example, in some embodiments, input portion 146 has a length sufficient to queue at least five carriers 101, for example, at least fifteen carriers 101.

In some embodiments in which buffer conveyor subassembly 114 includes a single movable track, buffer conveyor subassembly 114 includes a pair of rotating axles 174 and 176 around which the movable track moves. In such embodiments, buffer conveyor subassembly 114 can include a drive assembly 172 that powers the movable track. For example, drive assembly 172 can be operatively coupled to one of the axles 174 and 176, for example, axle 174 as shown in FIG. 4. Drive assembly 172 can include a motor that is operatively coupled to axle 174 via, for example, one or more of gears, pulleys, and belts that drive axle 174 and, in turn, the movable track. In some embodiments, drive assembly 172 is positioned between a housing panel 168 of instrument 108 and the track of buffer conveyor subassembly 114 as best seen in FIG. 4.

Figure 3:
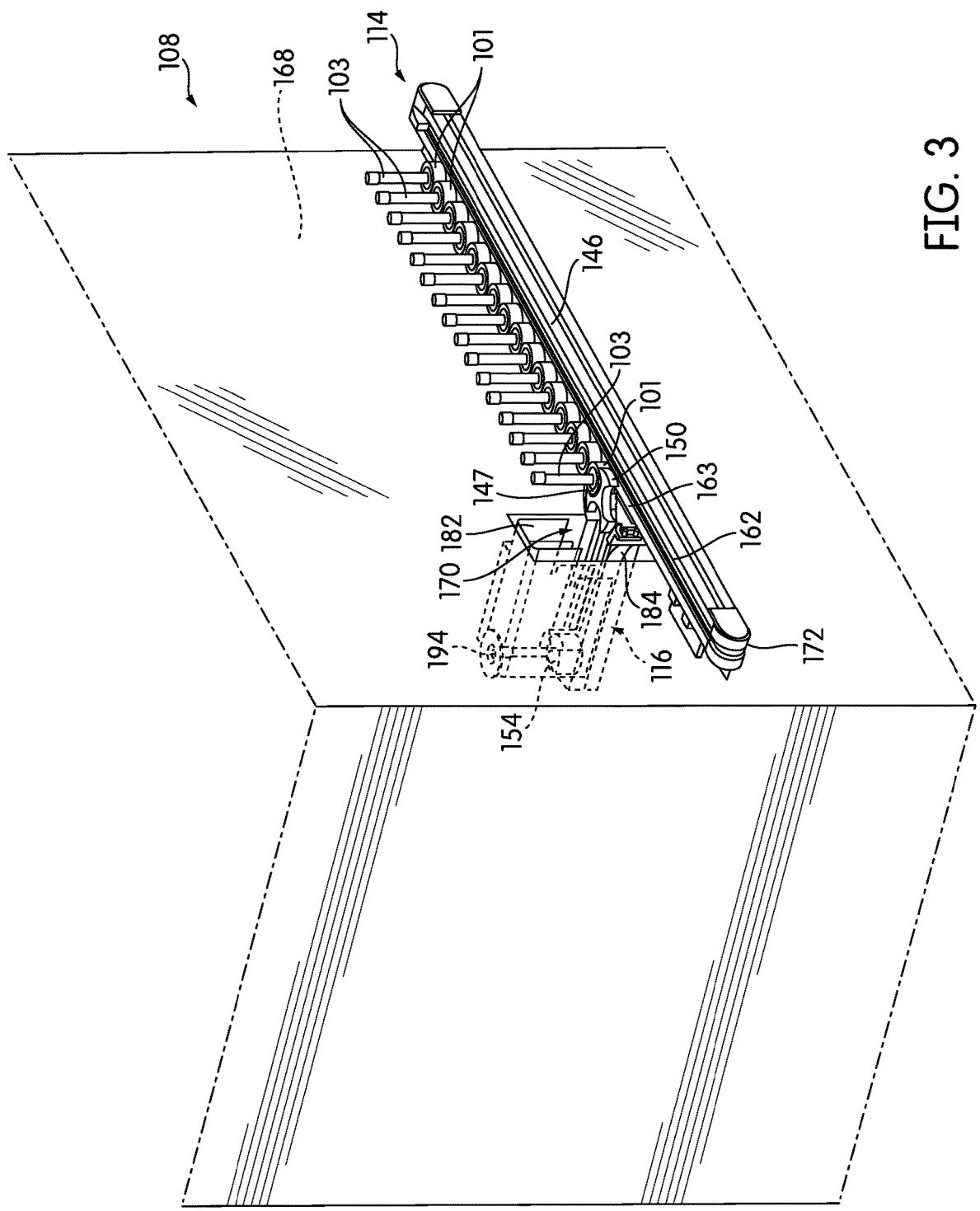
FIG. 3 is a rear view of an assay instrument and an intermediate conveyor assembly according to an embodiment.

In some embodiments, buffer conveyor subassembly 114 is mounted to an outer surface of housing panel 168 of assay instrument 108 as best seen in FIG. 3. In some embodiments, housing panel 168 is a rear housing panel of assay instrument 108 on a side opposite of a manual input bay of assay instrument 108. In such embodiments, the path along which carriers 101 are transported along buffer conveyor subassembly 114, which includes position 147, 163, and 167, is outside the housing of assay instrument 108. In some embodiments, as best seen in FIGS. 3 and 4, the path defined by buffer conveyor subassembly 114 is substantially parallel to housing panel 168 to which the buffer conveyor subassembly 114 is mounted. Buffer conveyor subassembly 114 can include a pair of mounting brackets 178 configured to secure buffer conveyor subassembly 114 to an outer surface of housing panel 168. In some embodiments, the path defined by buffer conveyor subassembly 114 is substantially parallel to the path defined by an adjacent portion of host conveyor assembly 102.

Buffer conveyor subassembly 114 can also include a carrier alignment bracket 180 in some embodiments, as best seen in FIG. 4. Alignment bracket 180 is shaped to push a carrier 101 to position 147 as the carrier 101 is transported by buffer conveyor subassembly 114 towards diverter 150. For example, the alignment bracket 180 can have a surface that is at an obtuse angle relative to the path defined by buffer conveyor subassembly 114 along which carriers 101 are transported. As the carrier 101 contacts this surface, the carrier 101 is pushed toward position 147 on buffer conveyor subassembly 114.

In some embodiments, buffer conveyor subassembly 114 also includes a sensor 148 configured to detect the presence of a carrier 101 at position 147 and/or read information (for example, an identifier) from a carrier 101, a receptacle 103 coupled to the carrier 101, or both the carrier and the receptacle 103. In some embodiments, diverter 150 is operably coupled to sensor 148 such that when a carrier 101 is detected to be at position 147 (and within a recess 155 defined by diverter 150), rotation of diverter 150 is actuated, and the carrier 101 is transported to position 153 on a portion 184 of spur conveyor subassembly 116. In some embodiments, sensor 148 is positioned on alignment bracket 180 or any other position near diverter 150. Sensor 148 can be an optical sensor or an RFID antenna.

Turning back to spur conveyor subassembly 116, subassembly 116 receives a carrier 101 from diverter 150 at position 153. Spur conveyor subassembly 116 is configured to transport the carrier 101 between position 153 and the processing position 154 within the housing of assay instrument 108. In some embodiments, housing panel 168 of assay instrument 108 defines an opening 170, and spur conveyor subassembly 116 extends from buffer conveyor subassembly 114 and through opening 170 into the interior of assay instrument 108. In some embodiments, opening 170 is sized such that a carrier 101 and processing receptacle 103 coupled thereto can pass through opening 170.

Spur conveyor subassembly 116 can be coupled to buffer conveyor subassembly 114. In some embodiments, as best shown in FIGS. 2-4 and 6, spur conveyor subassembly 116 is coupled to buffer conveyor subassembly 114 at a position that is aligned with diverter 150. In some embodiments as best seen in FIGS. 4 and 6, spur conveyor subassembly 116 is substantially perpendicular to buffer conveyor subassembly 114. In other embodiments (not shown), spur conveyor subassembly 116 is at a non-perpendicular angle relative buffer conveyor subassembly 114. In some embodiments, spur conveyor subassembly 116 bisects buffer conveyor subassembly 114.

In some embodiments as best seen in FIG. 5, spur conveyor subassembly 116 includes a movable gripper 188 that is movably coupled, for example, translatably coupled, to a base 186. For example, base 186 can define a groove (not shown), and gripper 188 can define a flange (not shown) translatably received within the groove of base 186, which allows gripper 188 to move relative to base 186 in the direction of the groove. Gripper 188 can move along a direction 190. Gripper 188 is configured to selectively grasp a carrier 101 at position 153 and transport the carrier 101 (along with the coupled processing receptacle 103) to the processing position 154 within a housing of assay instrument 108.

Referencing FIGS. 5 and 22-26, gripper 188 of spur conveyor subassembly 116 can include at least two movable prongs 189 configured to secure the carrier 101 to gripper 188, for example, by applying an effective amount of pressure to a carrier 101. As shown in FIGS. 5 and 22-26, gripper 188 has two movable prongs 189. In some embodiments, movable prongs 189 are pivotally coupled to a base 197 of gripper 188. For example, each movable prong 189 can be coupled to base 197 using a pivot pin 199 extending (e.g., substantially vertically) from base 197 about which each prong 189 pivots. Base 197 can be configured to engage a bottom surface of carrier 101. For example, when diverter 150 transports a carrier 101 from position 147 on buffer conveyor subassembly 114 to position 153 on spur conveyor subassembly 116, diverter 150 places the carrier 101 on top of base 197 of gripper 188. After the carrier 101 is transferred to base 197 of gripper 188, movable prongs 189 grasp carrier 101 by pivoting about pivot pin 199 toward each other and applying an effective amount of pressure to carrier 101 to secure the carrier 101 to gripper 188.

Gripper 188 can also include a wall 205 extending (e.g., substantially vertically) from base 197 of gripper 188. Wall 205 is configured to stop movement of a carrier 101 in a direction toward processing position 154 when diverter 150 transports a carrier 101 from position 147 on buffer conveyor subassembly 114 to position 153 on spur conveyor subassembly 116. In some embodiments, wall 205 is spaced apart from pivot pin 199 in a direction toward buffer subassembly 114.

In some embodiments, each prong 189 includes a first prong portion 191 that extends substantially perpendicularly (for example, vertically) away from base 186. First prong portion 191 can have a shape that closely corresponds to the perimeter of carrier 101. For example, if carrier 101 is a circular puck, first prong portion 191 can have a corresponding arcuate shape that closely corresponds the circularly periphery of carrier 101. In some embodiments, each prong 189 of gripper 188 also includes a second prong portion 193 that extends substantially perpendicularly (for example, horizontally) from first portion 191 towards a center of gripper 188. When gripper 188 is grasping a carrier 101, second prong portion 193 overlaps (in a vertical direction) at least a portion of carrier 101 as best shown in FIG. 5.

Figure 26:
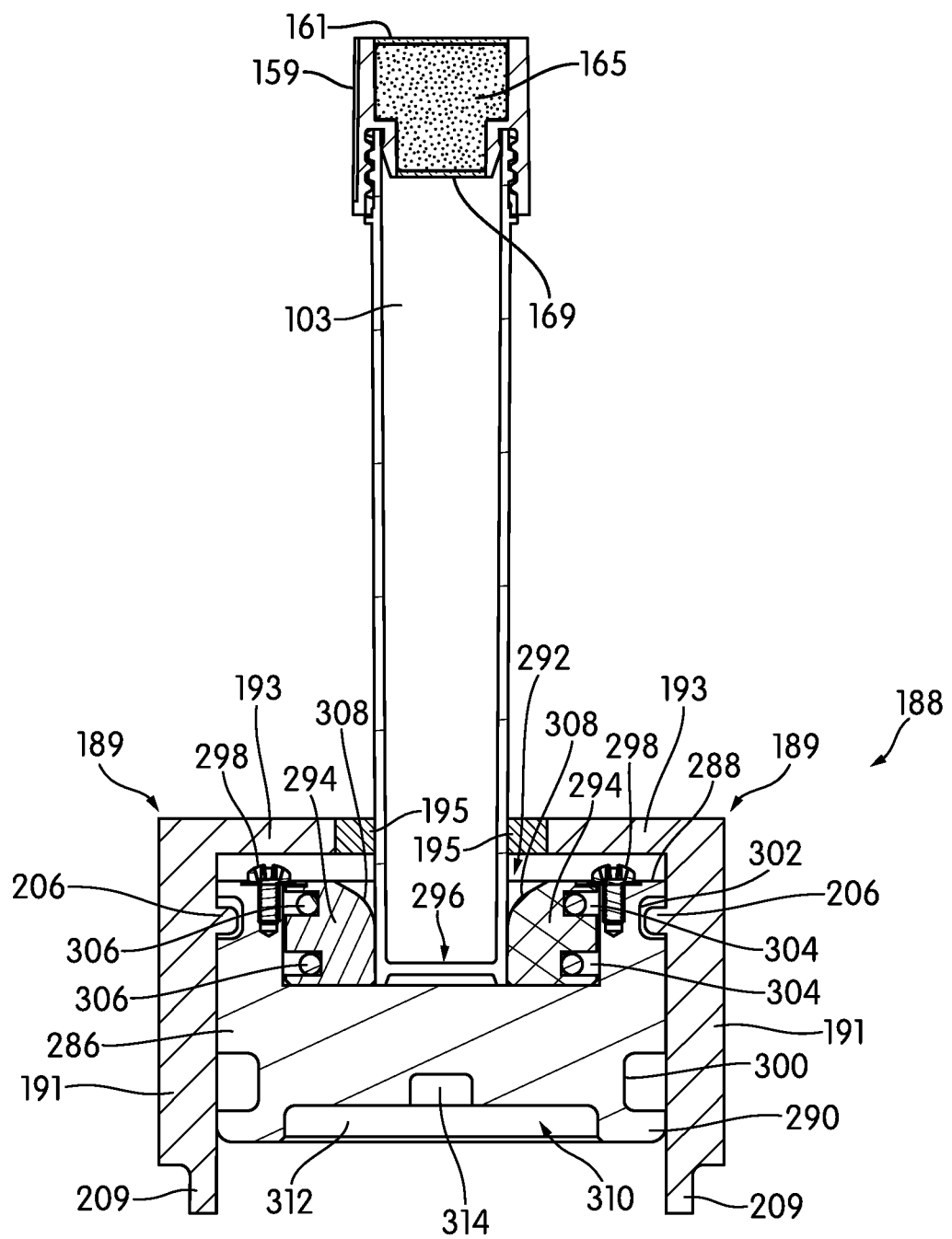
FIG. 26 is a cross-sectional view of a carrier, a receptacle, and a gripper in a closed configuration, according to an embodiment.
Figure 27:
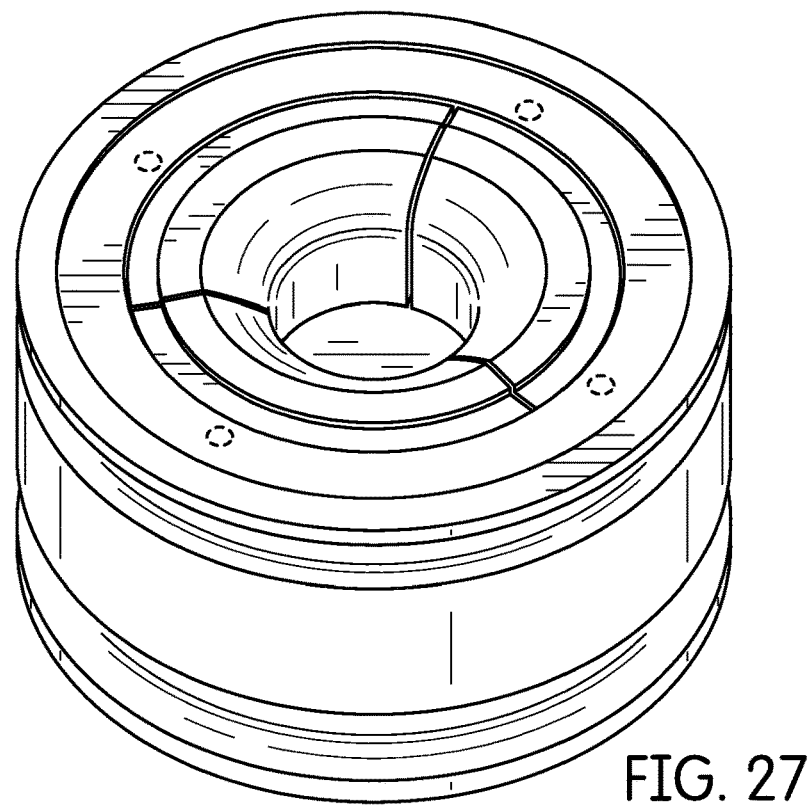
FIG. 27 is a top perspective view of a sample carrier showing a new design.
Figure 28:
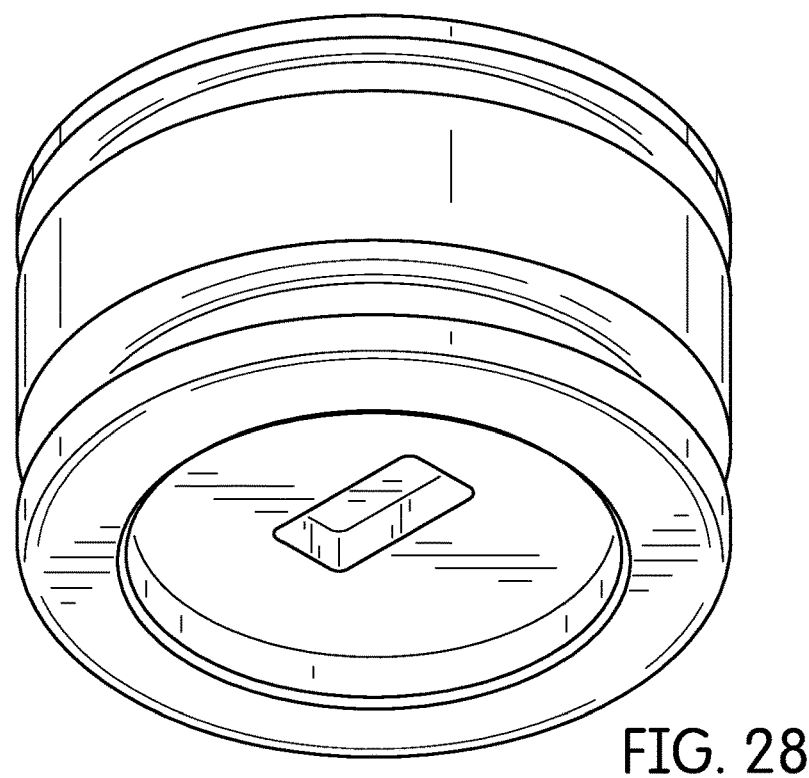
FIG. 28 is a bottom perspective view thereof.
Figure 29:
FIG. 29 is a front view thereof, the rear view being the same.
Figure 30:
FIG. 30 is a left side view thereof, the right side view being the same.
Figure 31:
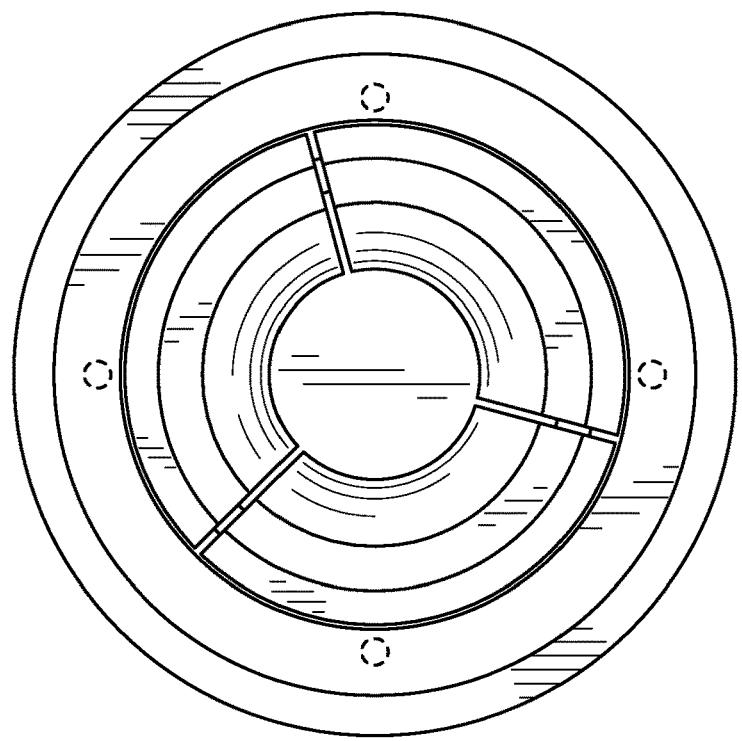
FIG. 31 is a top view thereof.
Figure 32:
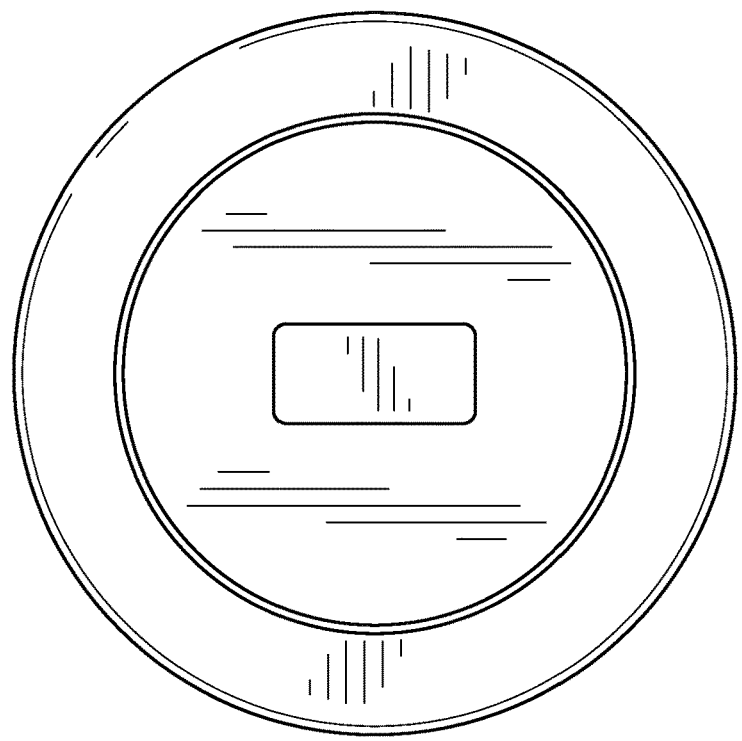
FIG. 32 is a bottom view thereof.
Figure 33:
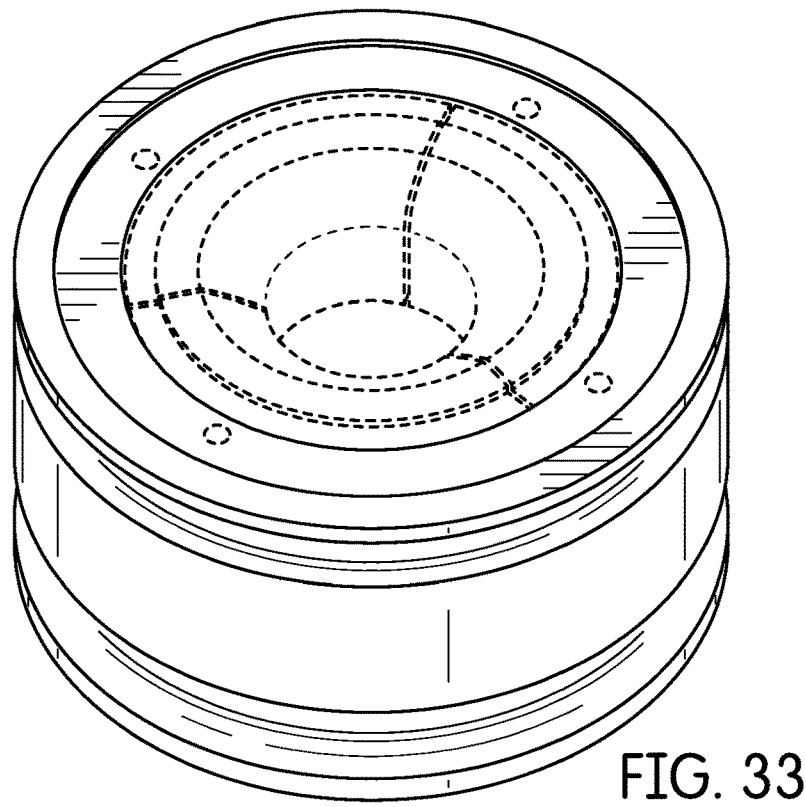
FIG. 33 is a top perspective view of another sample carrier showing our new design.
Figure 34:
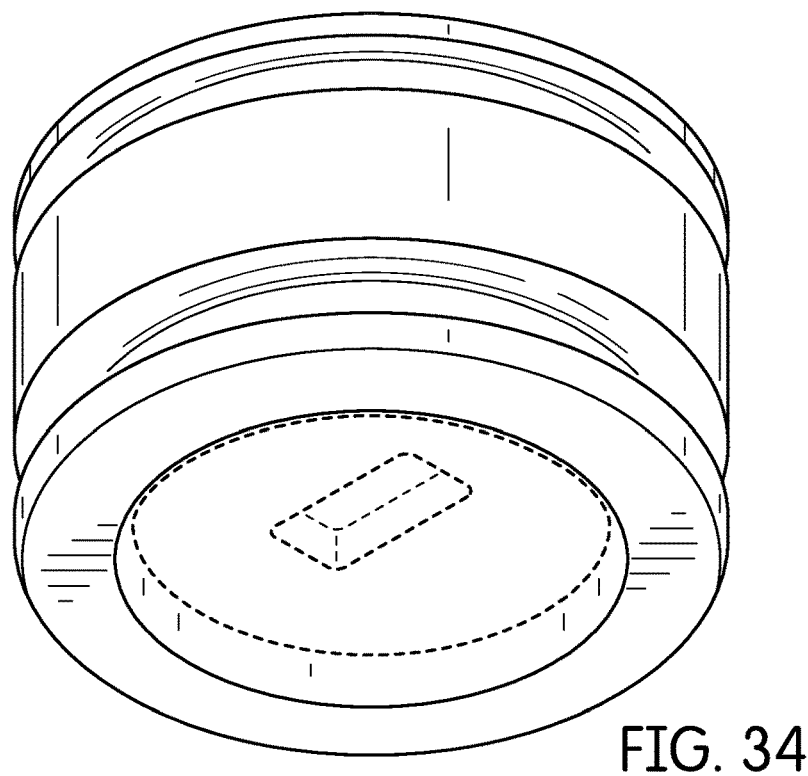
FIG. 34 is a bottom perspective view thereof.
Figure 35:
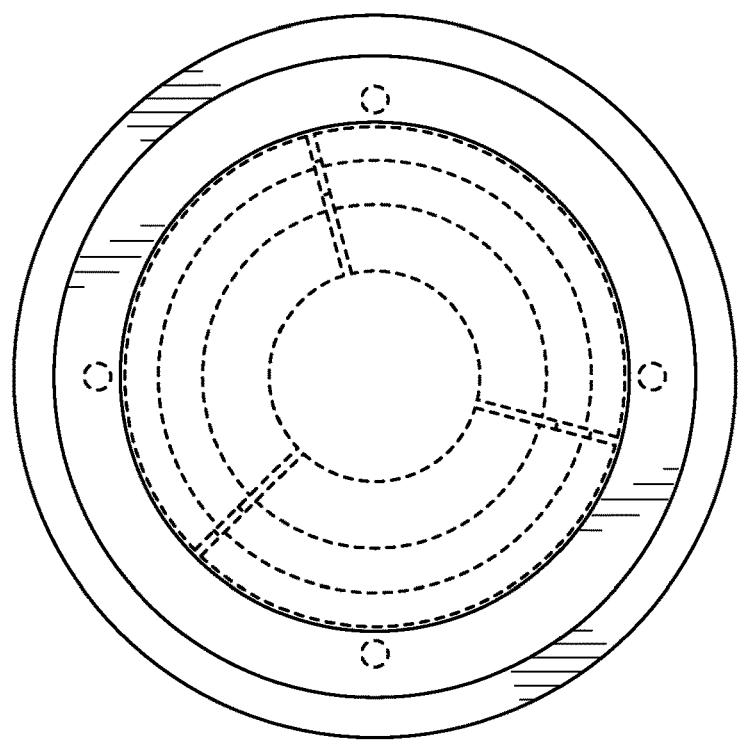
FIG. 35 is a top view thereof.
Figure 36:
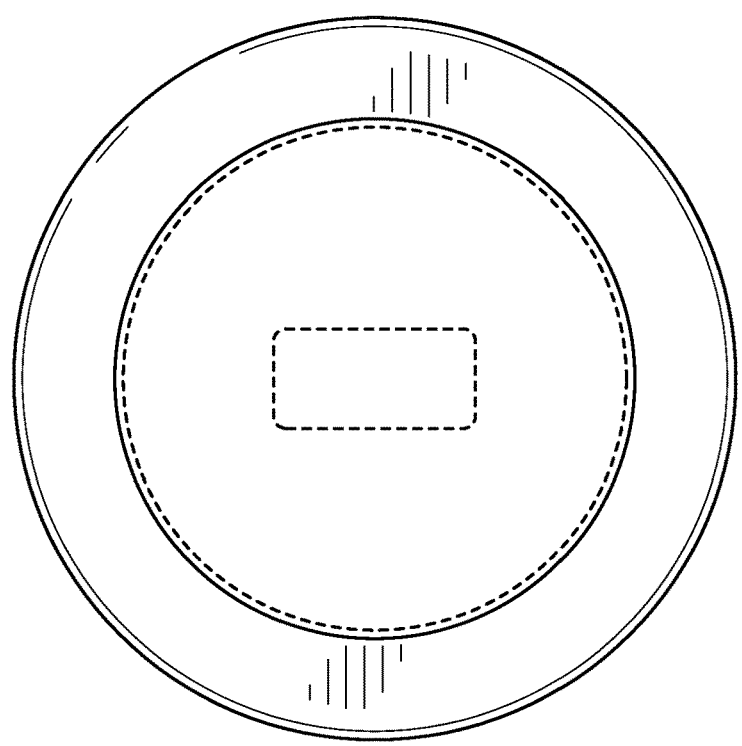
FIG. 36 is a bottom view thereof.
Figure 37:
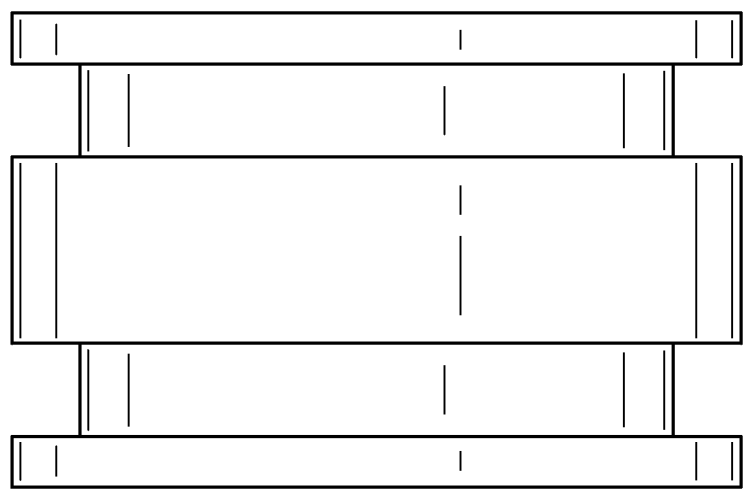
FIG. 37 is a front view of another sample carrier showing a new design, the rear, right, and left side views being the same.

In some embodiments (as best seen in FIG. 26), first prong portion 191 of prong 189 defines a protrusion 206 on a surface facing a carrier 101 on base 197 of gripper 188. Protrusion 206 is configured to be received in a groove 302 defined by carrier 101, which is explained further below in reference to FIGS. 17 and 18, when gripper 188 is in a closed configuration. When gripper 188 is in the closed configuration, protrusion 206 overlaps (in a vertical direction) at least a portion of the surface defining groove 302 of carrier 101. If a force is applied to carrier 101 in a direction away from base 186 of spur conveyor subassembly 116, protrusion 206 substantially prevents movement of carrier 101 in a direction of the applied forces, which secures carrier 101 to gripper 188 and spur conveyor subassembly 116. For example (referencing FIG. 8), protrusion 206 can hold carrier 101 down as a distal end of pipettor 158 of assay instrument 108 is removed from a processing receptacle 103 coupled to the carrier 101 at processing position 154. Removing the distal end of pipettor 158 from processing receptacle 103 can generate a force in the direction of movement of pipettor 158, and protrusion 206 of prongs 189 can hold the carrier 101 down. For example, in some embodiments, receptacle 103 includes a cap 159. Cap 159 defines a hollow cavity that is sealed on top with a metallic foil 161. The hollow cavity of cap 159 can be filled with a porous filter 165, and the bottom of the hollow cavity is sealed with another metallic foil 169. As the distal end of pipettor 158 is removed from processing receptacle 103, the distal end passes through the bottom foil 169, the filter 165, and the top metallic foil 161, generating a force in the direction of movement of pipettor 158. Protrusions 206 of prongs 189 hold carrier 101 in place by resisting this generated force.

In some embodiments (not shown), first prong portion 191 and second prong portion 193 are sized such that second portion 193 contacts the overlapped surface (for example, a top surface) of carrier 101 coupled to gripper 188 when gripper 188 is in the closed configuration. This way, if a force is applied to carrier 101 in a direction away from base 186 of spur conveyor subassembly 116, second prong portion 193 substantially prevents movement of carrier 101 in a direction of the applied forces, which secures carrier 101 to gripper 188 and spur conveyor subassembly 116. For example (referencing FIG. 8), second prong portion 193 can hold carrier 101 down as a distal end of pipettor 158 of assay instrument 108 is removed from a processing receptacle 103 coupled to a carrier 101 at processing position 154. Removing the distal end of pipettor 158 from processing receptacle 103 can apply a force in the direction of movement of pipettor 158, and second prong portions 193 of prongs 189 can hold the carrier 101 down.

Figure 25:
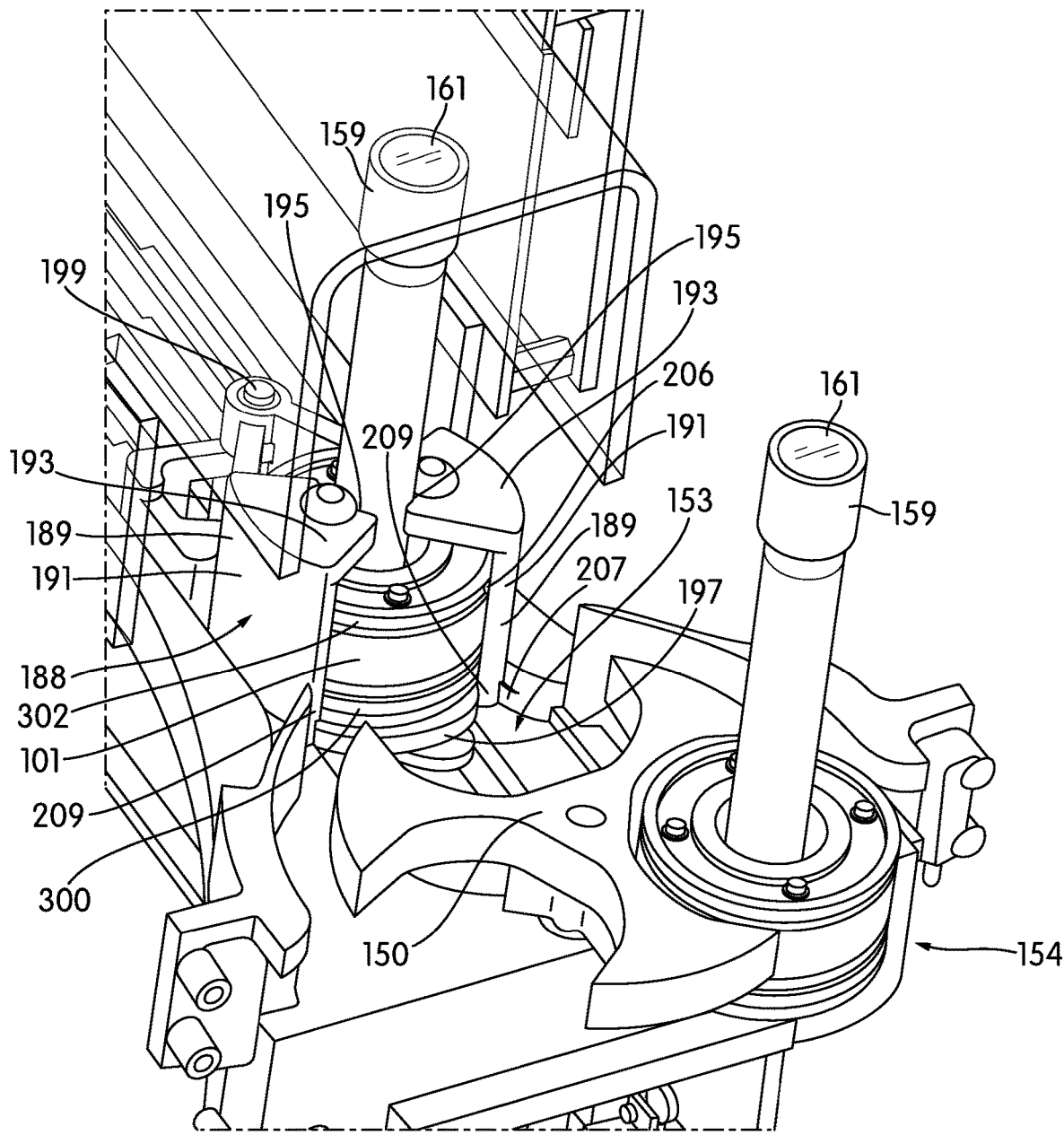
FIG. 25 perspective view of a diverter and a gripper (in a closed configuration) of a spur conveyor subassembly, according to an embodiment.

In some embodiments, second prong portions 193 of gripper prongs 189 are sized such than when prongs 189 are at a fully closed and grasping carrier 101 (i.e., at the closed configuration of gripper 188), there is a gap between the second prong portions 193 of prongs 189. This gap is sized to allow processing receptacle 103 to extend from carrier 101 in a direction away from base 186. The second prong portions 193 are sized such that the distal ends of each second prong portion 193 contact a processing receptacle 103 passing through the gap defined there between, thereby applying a force to receptacle 103 as best seen in FIGS. 25 and 26. This contact generates an axial retaining force (e.g., via friction) on receptacle 103 that secures receptacle 103 to carrier 101 when a force is applied to receptacle 103 in a direction away from carrier 101 and base 186 of spur conveyor subassembly 116 (for example, a force applied to receptacle 103 when the distal end of pipettor 158 is removed from receptacle 103). In some embodiments, each second prong portion 193 includes an elastomeric (for example, rubber) portion 195 that contacts receptacle 103. Elastomeric portion 195 can be configured to compress (which in turn enlarges the gap between second prong portions 193 through which a receptacle 103 passes) when contacting the receptacle 103. This compression allows gripper 188 to accommodate receptacles 103 having varying diameters, for example, diameters varying from about 8 mm to about 20 mm, including diameters of 12 mm and 16 mm. Elastomeric portion 195 can also increase the coefficient of friction at the interface between second prong portion 193 and receptacle 103, which increases the axial retaining force gripper 188 generates while grasping receptacle 103 with prongs 189. In some embodiments, the contact of second prong portions 193 against receptacle 103 can also help align receptacle 103 in a desired orientation (for example, in the vertical orientation) within spur conveyor subassembly 116.

Figure 24:
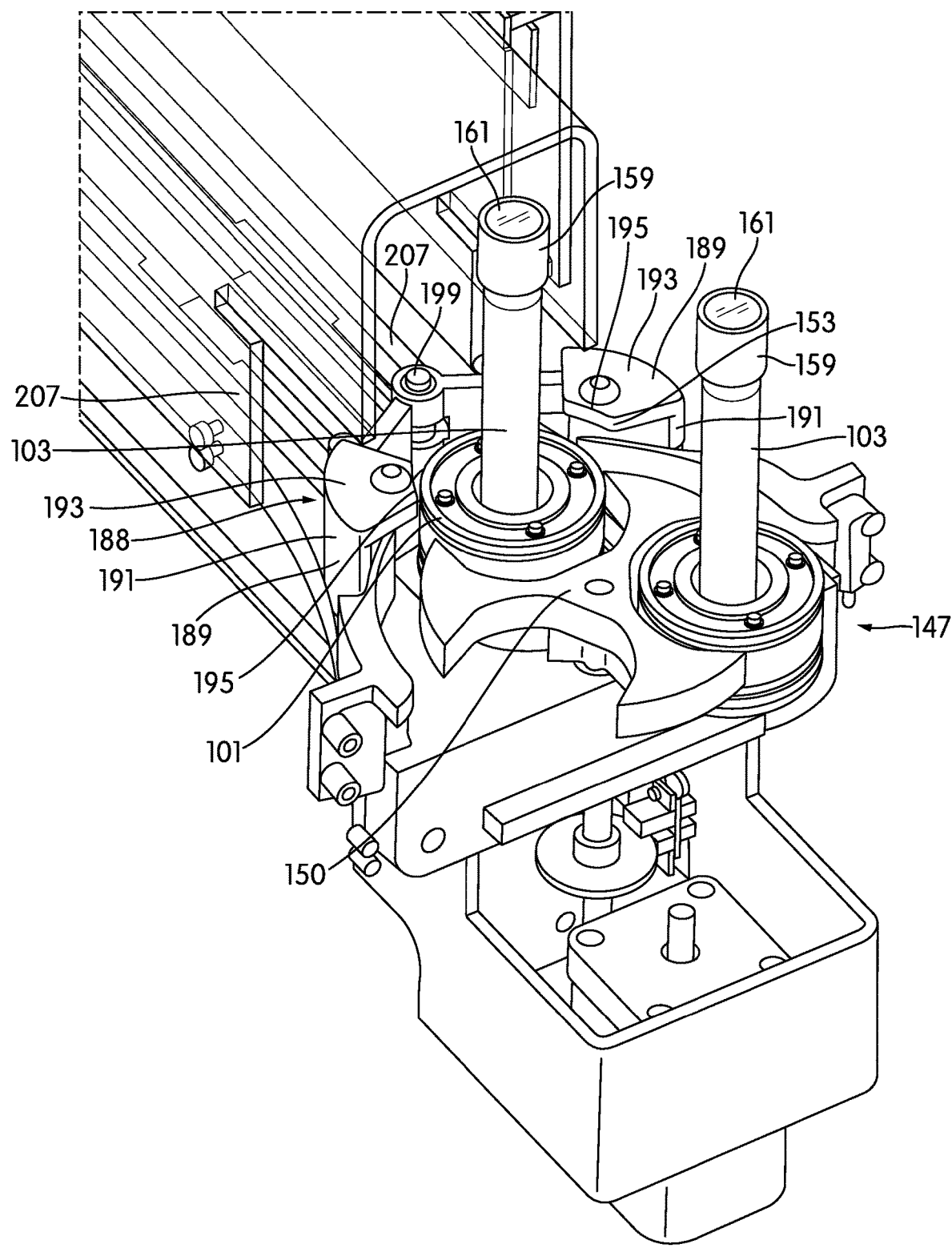
FIG. 24 is a perspective view of a diverter and a gripper (in an open configuration) of a spur conveyor subassembly, according to an embodiment.

Gripper 188 is configured to move between (1) an open configuration at which a carrier 101 is capable of moving relative to gripper 188 and (2) a closed configuration at which carrier 101 is secured to gripper 188. For example, FIG. 24 illustrates gripper 188 at the open configuration. At the open configuration, prongs 189 of gripper 188 are separated from each other such that prongs 189 do not contact carrier 101 or receptacle 103. Accordingly, protrusion 206 of each prong 189 is not received within groove 302 of carrier 101, and elastomeric portion 195 of each prong 189 does not contact receptacle 103. This open configuration of gripper 188 allows diverter 150 to easily (1) transfer a carrier 101 from position 147 on buffer conveyor subassembly 114 to position 153 on spur conveyor subassembly 116 such that carrier 101 is placed on top of base 197 of gripper 188, and/or (2) transfer another carrier 101 from position 153 on spur conveyor subassembly 116 to position 163 on buffer conveyor subassembly 114. In some embodiments, prongs 189 are biased to the closed configuration, for example, by using an extension spring 211. In other embodiments, prongs 189 are unbiased or biased to the open configuration using, for example, a compression spring.

FIGS. 25 and 26 illustrate gripper 188 at the closed configuration according to an embodiment. After carrier 101 is transferred onto base 197 of gripper 188 by diverter 150, gripper 188 moves to the closed configuration by pivoting prongs 189 about pivot pin 199 towards each other until prongs 189 contact the carrier 101 and apply an effective amount of pressure to the carrier 101 to secure the carrier 101 to gripper 188. At the closed configuration, protrusion 206 of each prong 189 is received within groove 302 of carrier 101, and elastomeric portion 195 of each prong 189 contacts receptacle 103. At the closed configuration, if a force is applied to carrier 101 in a direction away from base 186 of spur conveyor subassembly 116, protrusion 206 substantially prevents movement of carrier 101 in a direction of the applied forces, thereby securing carrier 101 to gripper 188 and spur conveyor subassembly 116. And at this closed configuration, the generated axial retaining force (e.g., via friction) on receptacle 103 by elastomeric portions 195 can secure receptacle 103 to carrier 101 when a force is applied to receptacle 103 in a direction away from carrier 101 and base 186 of spur conveyor subassembly 116.

In some embodiments, spur conveyor subassembly 116 is configured to move prongs 189 of gripper 188 to the open configuration when gripper 188 is at position 153. At position 153, gripper 188 receives a carrier 101 transferred by diverter 150 from buffer subassembly 114 and/or delivers a carrier 101 to be transferred by diverter 150 to buffer subassembly 114. And spur conveyor subassembly 116 is configured to move prongs 189 of gripper 188 to the closed configuration after carrier 101 is placed onto base 197 of gripper 188. In some embodiments, prongs 189 move to the closed configuration while gripper 188 is at position 153, and in other embodiments, prongs 189 move to the closed configuration after gripper 188 moves from position 153 and towards processing position 154. Spur conveyor subassembly 116 is also configured to maintain prongs 189 of gripper 188 at the closed configuration when gripper 188 is at the processing position 154, thereby ensuring carrier 101 and processing receptacle 103 are held down as a distal end of pipettor 158 of assay instrument 108 is removed from processing receptacle 103.

In some embodiments, movement of prongs 189 between the open and closed configurations is actuated by a cam interface. For example, base 186 of spur conveyor subassembly 116 can define a pair of elongated and symmetric grooves 207 that extend from processing position 154 to position 153. Proximate processing position 154 grooves 207 are substantially parallel, and proximate position 153 grooves 207 extend outward away from each other in a substantially V- or U-shape fashion. Each prong 189 includes a pin 209 (best shown in FIGS. 23 and 26) configured to be received within a respective groove 207. As gripper 188 moves along spur conveyor subassembly 116, pins 209 of prongs 189 interface with the surfaces defining grooves 207, which moves prongs 189 between the open and closed configurations. For example, as gripper 188 moves towards position 153, pins 209 move outwards as they each travel in a respective outwardly extending portion of a respective groove 207, which in turn moves prongs 189 to the open configuration via a cam interface between pins 209 and the surface that defines grooves 207. And as gripper 188 moves back towards processing position 154, pins 209 move inward as they travel back towards the parallel portion of grooves 207, which in turn moves prongs 189 to the closed configuration via a cam interface between pins 209 and the surface that defines grooves 207.

In other embodiments, movement of prongs 189 between the open and closed configurations is selectively controlled by electro-mechanical configurations. For example, gripper 188 can include another drive assembly (e.g., a motor with belts, links, or gears) operatively coupled to prongs 189. The drive assembly can move prongs 189 between the open and closed configurations.

Spur conveyor subassembly 116 can also include a drive assembly 192 mounted to base 186. Drive assembly 192 is configured to selectively move gripper 188 along direction 190. In some embodiments, drive assembly 192 includes a motor operatively coupled to gripper 188 via one or more gears, pulleys, links, or belts. In some embodiments, drive assembly 192 is positioned on a side of processing position 154 away from position 153 of spur conveyor subassembly 116. For example, referencing FIG. 22, drive assembly 192 can be operatively coupled to a drive belt 320 that is operatively coupled to gripper 188, for example, to base 197 of gripper 188. Drive belt 320 can be rotationally mounted to spur conveyor subassembly 116 by a pair of rotating axles 322 and 324. Drive assembly 192 is operatively coupled to axle 322 by one or more of gears, pulleys, and belts (not shown in FIG. 22) to power axle 322 and, thereby, move belt 320. The position of gripper 188 is fixed relative to drive belt 320. Referencing FIG. 22, as drive belt 320 rotates in a counter-clockwise direction, gripper 188 moves towards diverter 150, and as drive belt 320 rotates in a clockwise direction, gripper 188 moves towards processing position 154.

In other embodiments, instead of or in addition to gripper 188, spur conveyor subassembly 116 includes a single movable track that transports carrier 101 between position 153 and processing position 154. Drive assembly 192 is configured to selectively move the track and, in turn, transport a carrier 101 in both directions 190. In such embodiments, a carrier 101 can sit on top of the movable track as the track moves with the carrier 101.

For example, in some embodiments, a movable track moves carrier 101 from position 153 to processing position 154, and at processing position 154, a stationary gripper 188 grasps carrier 101 securing carrier 101 at processing position 154. After gripper 188 grasps carrier 101, automated pipettor 158 can aspirate a portion of a sample in a receptacle coupled to the carrier 101 being grasped by gripper 188. After a sample is aspirated, gripper 188 can release the carrier 101, and the movable track can transport the carrier back to position 153.

In some embodiments, spur conveyor subassembly 116 includes both gripper 188 and diverter 150. In other embodiments, spur conveyor subassembly 116 omits one of either gripper 188 or diverter 150. For example, spur conveyor subassembly 116 can include gripper 188, but not diverter 150, or spur conveyor subassembly 116 can include diverter 150, but not gripper 188.

Spur conveyor subassembly 116 can also include a cover 182 in some embodiments. Cover 182 overlaps at least a portion of the path defined by spur conveyor subassembly 116 to help prevent cross-contamination from substances dropping from pipettor 158 as it moves within the housing of assay instrument 108 or from other processes occurring within the housing of assay instrument 108. In some embodiments, cover 182 overlaps substantially the entire portion 183 (shown in FIG. 4) of the path between position 153 and processing position 154 that is within the housing of assay instrument 108. For example, one end of cover 182 is adjacent an inner surface of housing panel 168 of assay instrument 108, which defines opening 170, and the other end of cover 182 is adjacent and overlaps processing position 154. Accordingly, when position 153 is outside the housing of assay instrument 108 and processing position 154 is within the housing of assay instrument 108, a portion 184 of the path defined by spur conveyor subassembly 116 is outside the housing and uncovered, but the portion 183 of the path defined by spur conveyor subassembly 116 that is inside the housing and is covered and substantially enclosed by cover 182, thereby reducing the risk of cross-contamination. Cover 182 is sized and shaped to allow processing receptacle 103 coupled to a carrier 101 to pass from position 153 to processing position 154. In some embodiments as shown in FIG. 5, cover 182 has a substantially inverted U-shape, or any other suitable shape.

Figure 8:
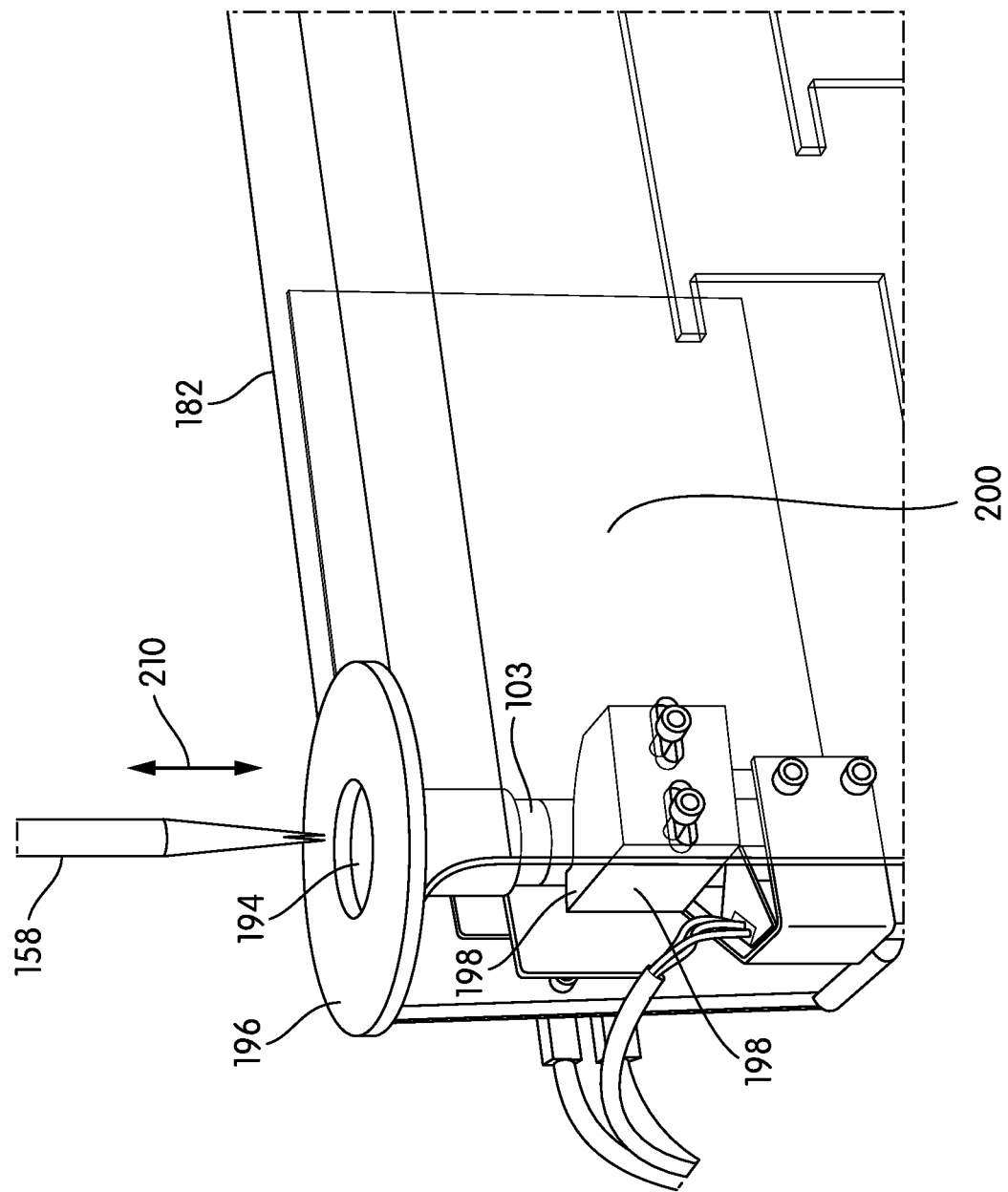
FIG. 8 is a perspective view of a pipettor of an assay instrument, a spur conveyor subassembly of an intermediate conveyor assembly, and a processing receptacle, according to an embodiment.
Figure 9:
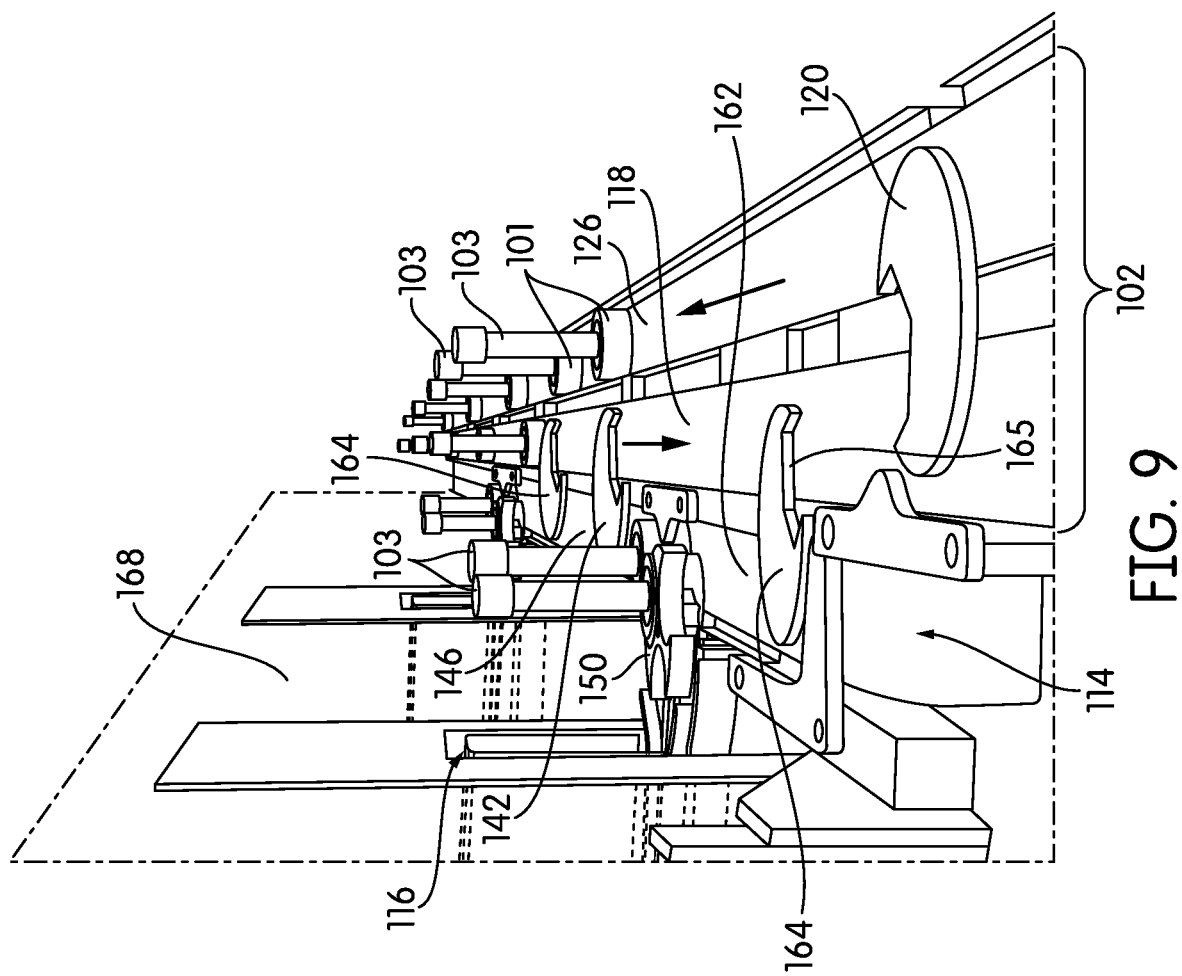
FIG. 9 is a perspective view of a host conveyor assembly operatively coupled to intermediate conveyor assemblies and assay instruments, according to an embodiment.
Figure 10:
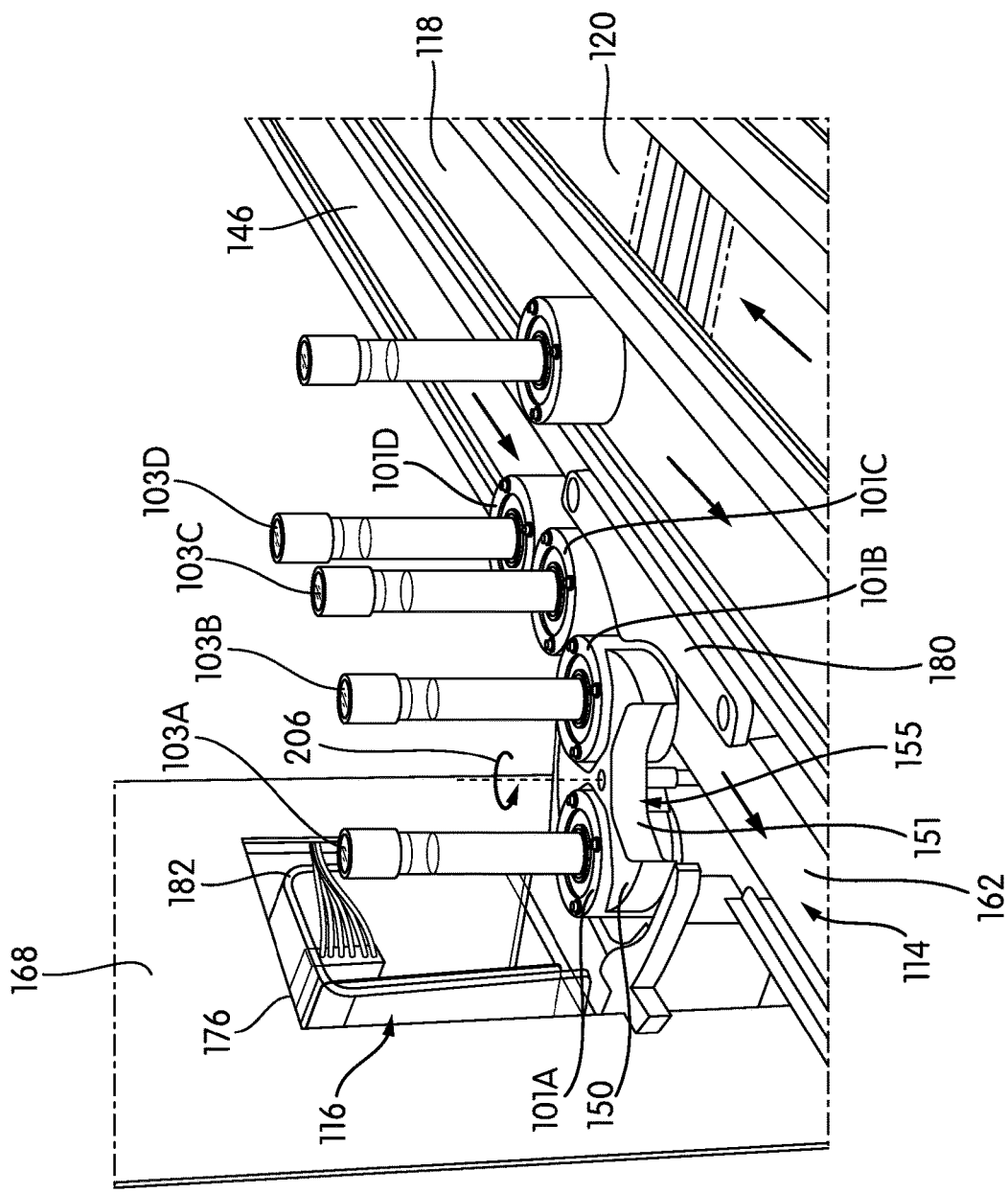
FIG. 10 is a perspective view of an assay instrument, an intermediate conveyor assembly, and a host conveyor assembly, according to an embodiment.

In some embodiments, a portion of cover 182 overlapping processing position 154 defines an opening 194. Opening 194 can be circular in some embodiments as shown in FIGS. 5, 6, and 8. Opening 194 is configured to allow a distal end of pipettor 158, for example, which includes a disposable tip or probe, to pass and then be inserted into processing receptacle 103 coupled to carrier 101, which is positioned at processing position 154 and secured at that position 154 by gripper 188. In some embodiments, cover 182 also includes an alignment plate 196. As shown in FIG. 5, alignment plate 196 is a separate component from the remainder of cover 182. But in other embodiments, alignment plate 196 can be formed integrally with the remainder of cover 182. Alignment plate 196 defines a tapered surface that surrounds opening 194 defined by cover 182. The tapered surfaces can automatically align the distal end of pipettor 158 as the distal end of pipettor 158 is moved toward processing receptacle 103 if pipettor 158 is slightly misaligned relative to receptacle 103.

Cover 182 can be coupled to base 186. In some embodiments, cover 182 is removably coupled to base 186. In such removable embodiments, cover 182 can be removed for cleaning. In other embodiments, cover 182 is permanently coupled to base 186. In some embodiments, cover 182 is composed of a material compatible with being decontaminated in a bleach solution.

In other embodiments (not shown), instead of cover 182 being part of spur conveyor subassembly 116, cover 182 is part of assay instrument 108.

Spur conveyor subassembly 116 can also include a receptacle alignment block 198 in some embodiments. Alignment block 198 is configured to automatically align a processing receptacle 103 coupled to a carrier 101 at the processing position 154 at an orientation aligned with the direction of travel of pipettor 158 (for example, receptacle alignment block 198 can orient receptacle 103 in a vertical orientation). Alignment block 198 defines a recess configured to receive a portion of receptacle 103 coupled to a carrier 101 at the processing receptacle 103. As the portion of receptacle 103 is received within this recess defined by alignment block 198, processing receptacle 103 coupled to the carrier 101 is automatically aligned with the direction of travel of pipettor 158 and with opening 194 defined by cover 182. In some embodiments, alignment block 198 is positioned on a side of processing position 154 away from position 153.

As shown in FIG. 8, pipettor 158 of assay instrument 108 is configured to move along direction 210. As pipettor 158 moves in direction 210 toward base 186, a distal tip of pipettor 158 is inserted through opening 194 defined by cover 182 until it is inserted within processing receptacle 103, which is coupled to a carrier 101 positioned at processing position 154.

In some embodiments, spur conveyor subassembly 116 includes a sensor 156 configured to detect information (e.g., an identifier) of the carrier 101, the processing receptacle 103 coupled to the carrier 101, or both, when the carrier 101 is positioned at processing position 154 of assay instrument 108. For example, in some embodiments, sensor 156 is positioned near a terminal end of the path defined by spur conveyor subassembly 116 along which a carrier 101 is transported. In some embodiments, sensor 156 is covered by cover 182. In some embodiments, sensor 156 is adjacent base 186 of spur conveyor subassembly 116 and is below gripper 188. In some embodiments, assay instrument 108 is configured to start aspirating at least a portion of a sample from the processing receptacle 103 coupled to a carrier 101 at the processing position 154 of assay instrument 108 based on the detected identifier of the carrier 101, the processing receptacle 103 coupled to the respective carrier 101, or both, by sensor 156. In some embodiments in which at least one of the carrier 101 and the respective processing receptacle 103 includes an RFID tag that transmits an identifier or other information, sensor 156 is an RFID antenna configured to detect the identifier or other information transmitted by the RFID tag on the at least one of carrier 101 and processing receptacle 103. In other embodiments in which at least one of the carrier 101 and the respective processing receptacle 103 includes a machine readable label, for example, a barcode, that includes the identifier or other information, sensor 156 is an image sensor, for example, a barcode reader, configured to detect the label on the at least one of carrier 101 and processing receptacle 103. In some embodiments, sensor 156 is also configured to detect the presence of a carrier 101 at position 154.

Intermediate conveyor assembly 133 includes a controller 200. In some embodiments, controller 200 is positioned on spur conveyor subassembly 116. For example, controller 200 can be mounted to cover 182. In some embodiments, controller 200 includes one or more processors, one or more of drivers for the drive assemblies, and one or more communication interfaces as described further below. In some embodiments, controller 200 is operatively coupled to one or more of drive assembly 172 of buffer conveyor subassembly 114, drive assembly 202 of diverter 150, and drive assembly 192 of gripper 188 to control the operations of these components.

Figure 11:
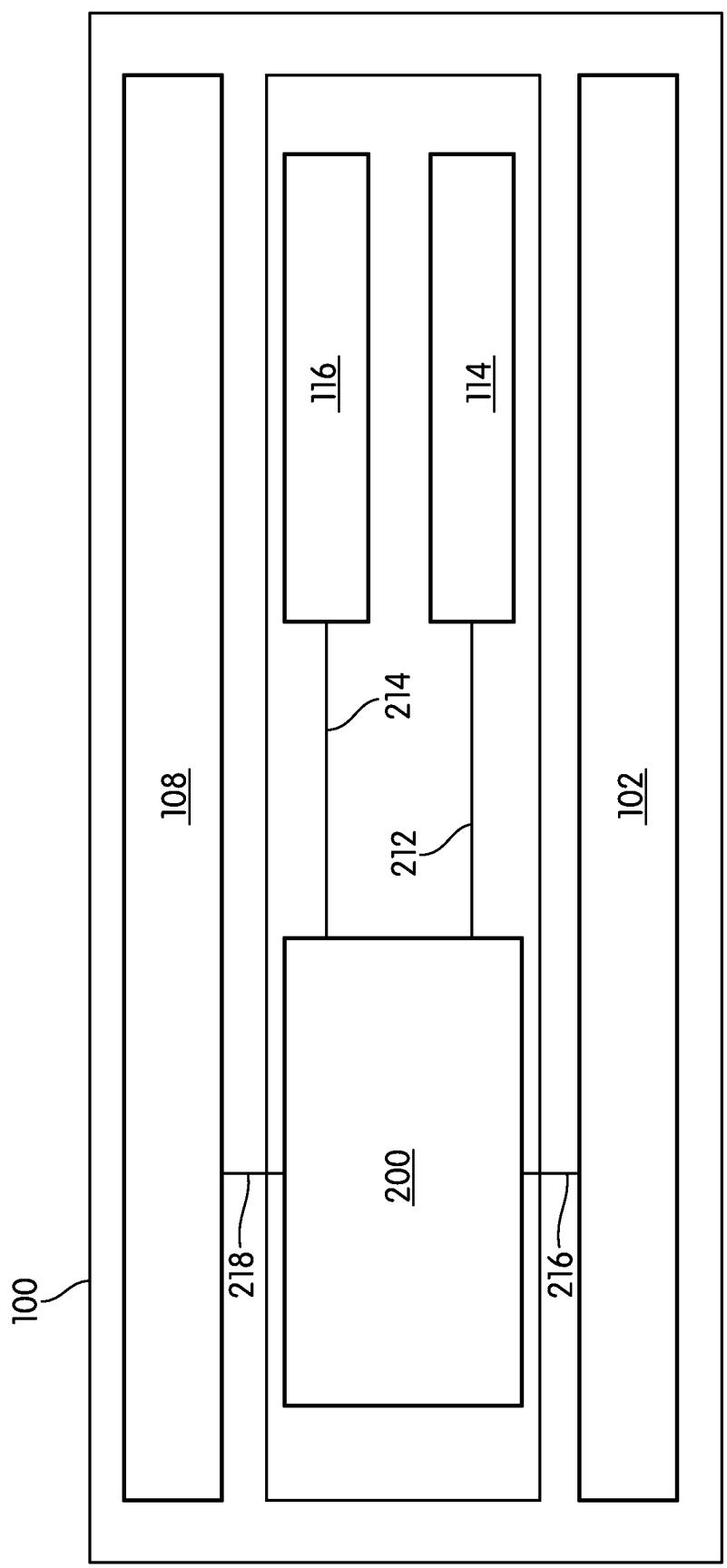
FIG. 11 is a schematic system diagram of a host conveyor assembly, an intermediate conveyor assembly, and an assay instrument, according to an embodiment.
Figure 12:
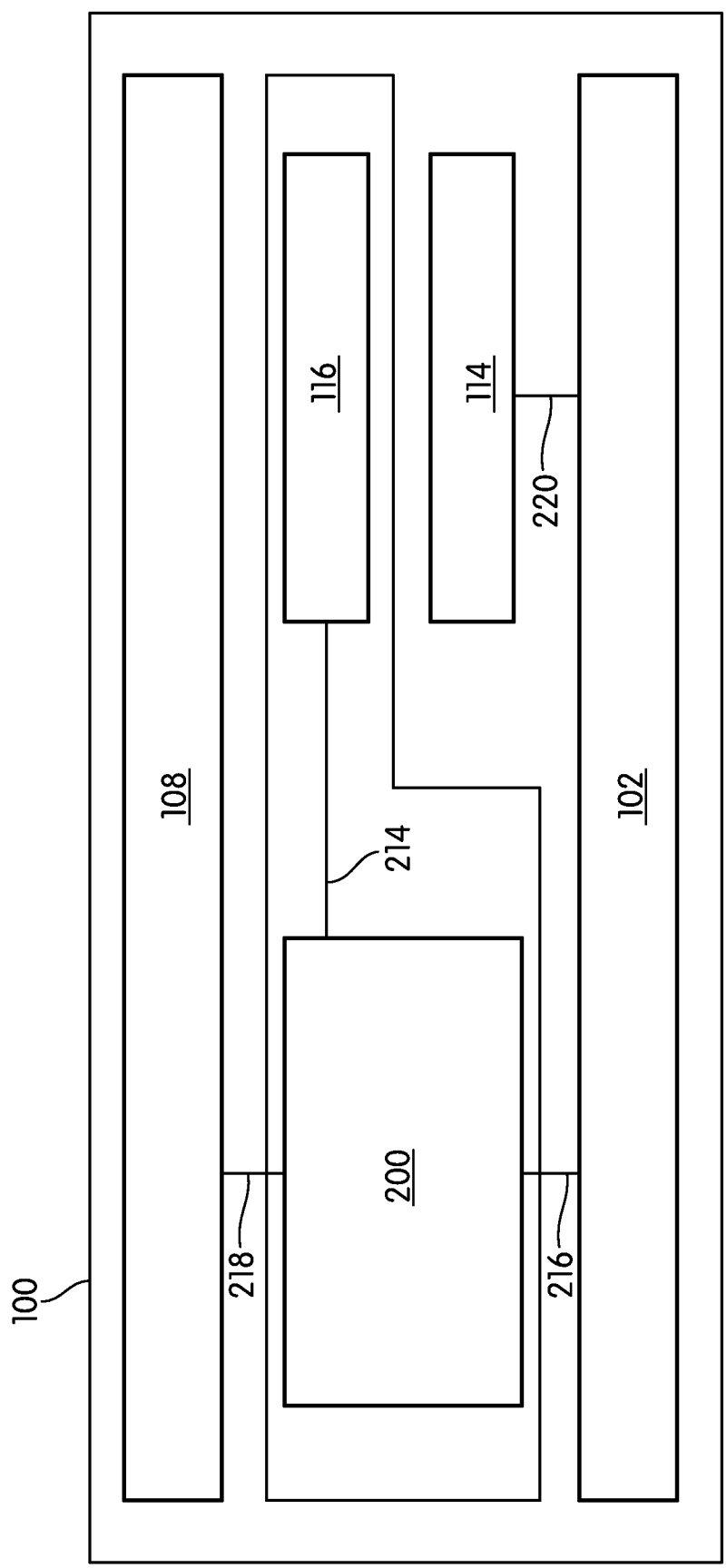
FIG. 12 is a schematic system diagram of a host conveyor assembly, an intermediate conveyor assembly, and an assay instrument, according to another embodiment.
Figure 13:
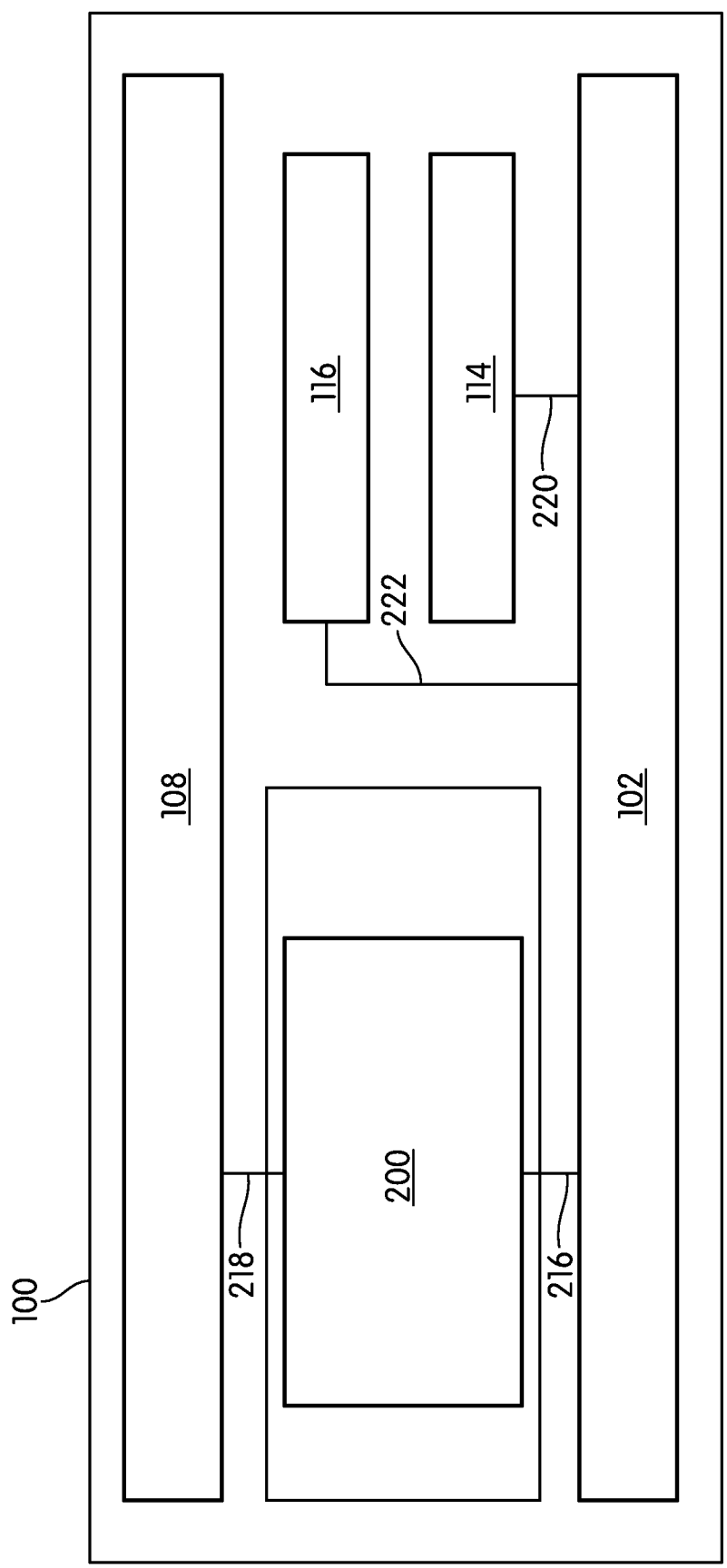
FIG. 13 is a schematic system diagram of a host conveyor assembly, an intermediate conveyor assembly, and an assay instrument, according to yet another embodiment.

FIGS. 11-13 schematically illustrate various exemplary system architectures of controller 200 relative to host conveyor assembly 102 and assay instrument 108.

As shown in FIG. 11, controller 200 is operatively and directly coupled to buffer conveyor subassembly 114 via one or more communication links 212 and spur conveyor subassembly 116 via one or more communication links 214 in some embodiments. In such embodiments, controller 200 can directly control the track of buffer conveyor subassembly 114 and the gripper 188 of spur conveyor subassembly 116 via respective communication links 212 and 214. For example, controller 200 can send a control signal via communication link 212 to drive assembly 172 of buffer conveyor subassembly 114, and controller 200 can send a control signal via communication link 214 to drive assembly 192 of spur conveyor subassembly 116. Controller 200 can also directly monitor the sensors of buffer conveyor subassembly 114 and the sensors of spur conveyor subassembly 116. For example, controller 200 can receive a signal via communication link 212 from sensor 148 on buffer conveyor subassembly 114 that is indicative of whether a carrier 101 is present at position 147, and controller 200 can receive a signal via communication link 214 from sensor 156 on spur conveyor subassembly 116 indicative of information, for example, an identifier, detected from carrier 101, receptacle 103, or both, when the carrier 101 is at processing position 154. Controller 200 can also directly control diverter 150 on spur conveyor subassembly 116 using a control signal transmitted via communication link 214. In some embodiments, controller 200 controls diverter 150 by adjusting the control signal transmitted to diverter 150 based on the signal received from sensor 148. In some embodiments, controller 200 is in communication with the controllers of assay instruments 108 via one or more communication links 218, for example, CAN, RS485, RS422, Ethernet, USB, or wireless communication interfaces. Controller 200 is also in communication with the controller of host conveyor assembly 102 via one or more communication links 216, for example, CAN, RS485, RS422, Ethernet, USB, or wireless communication interfaces.

As shown in FIG. 12, controller 200 is operatively and directly coupled to only spur conveyor subassembly 116 via one or more communication links 214 according to another embodiment. Controller 200 can directly control the track of spur conveyor subassembly 116 via communication link 214. For example, controller 200 can send a control signal via communication link 214 to drive assembly 192 of spur conveyor subassembly 116. Controller 200 can also directly monitor the sensors of spur conveyor subassembly 116. For example, controller 200 can receive a signal via communication link 214 from sensor 156 on spur conveyor subassembly 116 indicative of information, for example, an identifier, detected from carrier 101, receptacle 103, or both, when the carrier 101 is at processing position 154. Controller 200 can also directly control diverter 150 on spur conveyor subassembly 116 using a control signal transmitted via communication link 214. In some embodiments, the controller of host conveyor assembly 102 can directly control buffer conveyor subassembly 114 via one or more communication links 220. For example, the controller of host conveyor assembly 102 can directly control the track of buffer conveyor subassembly 114 via communication link 220. For example, the controller of host conveyor assembly 102 can send a control signal via communication link 220 to drive assembly 172 of buffer conveyor subassembly 114. The controller of host conveyor assembly 102 can also directly monitor the sensors of buffer conveyor subassembly 114. For example, the controller of host conveyor assembly 102 can receive a signal via communication link 220 from sensor 148 on buffer conveyor subassembly 114 that is indicative of whether a carrier 101 is present at position 147. In some embodiments, the controller of host conveyor assembly 102 controls diverter 150 by adjusting the control signal transmitted to diverter 150 based on the signal received from sensor 148. Controller 200 is in communication with the controllers of assay instruments 108 via one or more communication links 218, for example, CAN, RS485, RS422, Ethernet, USB, or wireless communication interfaces. Controller 200 is also in communication with the controller of host conveyor assembly 102 via one or more communication links 216, for example, CAN, RS485, RS422, Ethernet, USB, or wireless communication interfaces.

As shown in FIG. 13, the controller of host conveyor assembly 102 is operatively and directly coupled to buffer conveyor subassembly 114 via one or more communication links 222 and to spur conveyor subassembly 116 via one or more communication links 220 according to another embodiment. In such embodiments, the controller of host conveyor assembly 102 can directly control the track of buffer conveyor subassembly 114 and gripper 188 of spur conveyor subassembly 116 via respective communication links 220 and 222. For example, the controller of host conveyor assembly 102 can send a control signal via communication link 220 to drive assembly 172 of buffer conveyor subassembly 114, and the controller of host conveyor assembly 102 can send a control signal via communication link 222 to drive assembly 192 of spur conveyor subassembly 116. The controller of host conveyor assembly 102 can also directly monitor the sensors of buffer conveyor subassembly 114 and spur conveyor subassembly 116. For example, the controller of host conveyor assembly 102 can receive a signal via communication link 220 from sensor 148 on buffer conveyor subassembly 114 that is indicative of whether a carrier 101 is present at position 147, and the controller of host conveyor assembly 102 can receive a signal via communication link 222 from sensor 156 on spur conveyor subassembly 116 indicative of information, for example, an identifier, from carrier 101, receptacle 103, or both, when the carrier 101 is at processing position 154. The controller of host conveyor assembly 102 can also directly control diverter 150 on buffer conveyor subassembly 114 using a control signal transmitted via communication link 220. In some embodiments, the controller of host conveyor assembly 102 controls diverter 150 by adjusting the control signal transmitted to diverter 150 based on the signal received from sensor 148. In such embodiments, controller 200 is in communication with the controllers of assay instruments 108 via one or more communication links 218, for example, CAN, RS485, RS422, Ethernet, USB, or wireless communication interfaces, and controller 200 is also in communication with the controller of host conveyor assembly 102 via one or more communication links 216, for example, CAN, RS485, RS422, Ethernet, USB, or wireless communication interfaces.

Figure 14:
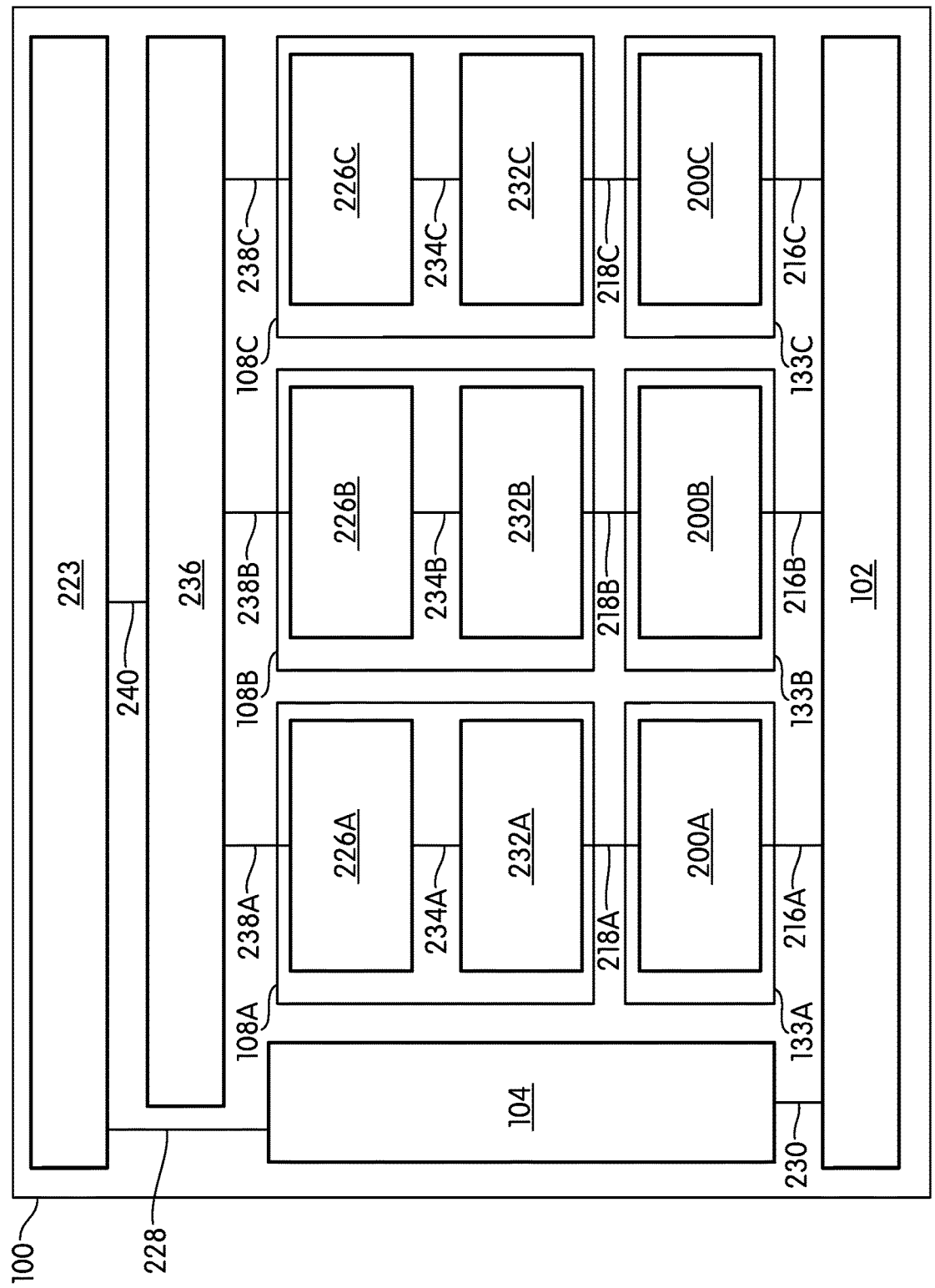
FIG. 14 is a schematic system diagram of a sample processing instrument, a host conveyor assembly, intermediate conveyor assemblies, and assay instruments, according to an embodiment.

FIG. 14 schematically illustrates a configuration of system 100 that also includes a lab information system 223. As shown in FIG. 14, system 100 includes a lab information system 223, processing instrument 104, and a plurality of assay instruments 108a-108c. The controller of processing instrument 104 is in communication with lab information system 223 via one or more communication links 228. And the controller of processing instrument 104 is in communication with the controller of host conveyor assembly 102 via one or more communication links 230. As explained above, the controller of host conveyor assembly 102 can be in communication with controllers 200a-c of respective intermediate conveyor assemblies 133a-133b via respective one or more communication links 216a-c. Controllers 200a-c are in communication with respective communication interfaces 232a-c, for example, COP modules, of controllers 226a-c of respective assay instruments 108a-c via respective one or more communication links 234a-c. Controllers 226a-226c of assay instruments 108a-c are in communication directly or indirectly with lab information system 223. For example, as shown in FIG. 14, controllers 226a-c of assay instruments 108a-c are directly in communication with an intermediate communication module 236 via respective communication links 238a-c. In some embodiments, intermediate communication module 236 acts as a firewall between lab information system 223 and assay instruments 108. Intermediate communication module 236 is in communication with lab information system 223 via one or more communication links 240. In some embodiments, intermediate communication module 236 is omitted such that controllers 226a-226c communicate directly with lab information system 223 via communication links 238a-c. In some embodiments, communication links 228, 230, 216a-216c, 218a-218c, 234a-234c, 238a-238c, and 240 can be any one of CAN, RS485, RS422, Ethernet, USB, wireless communication interfaces, or a combination thereof.

Figure 15:
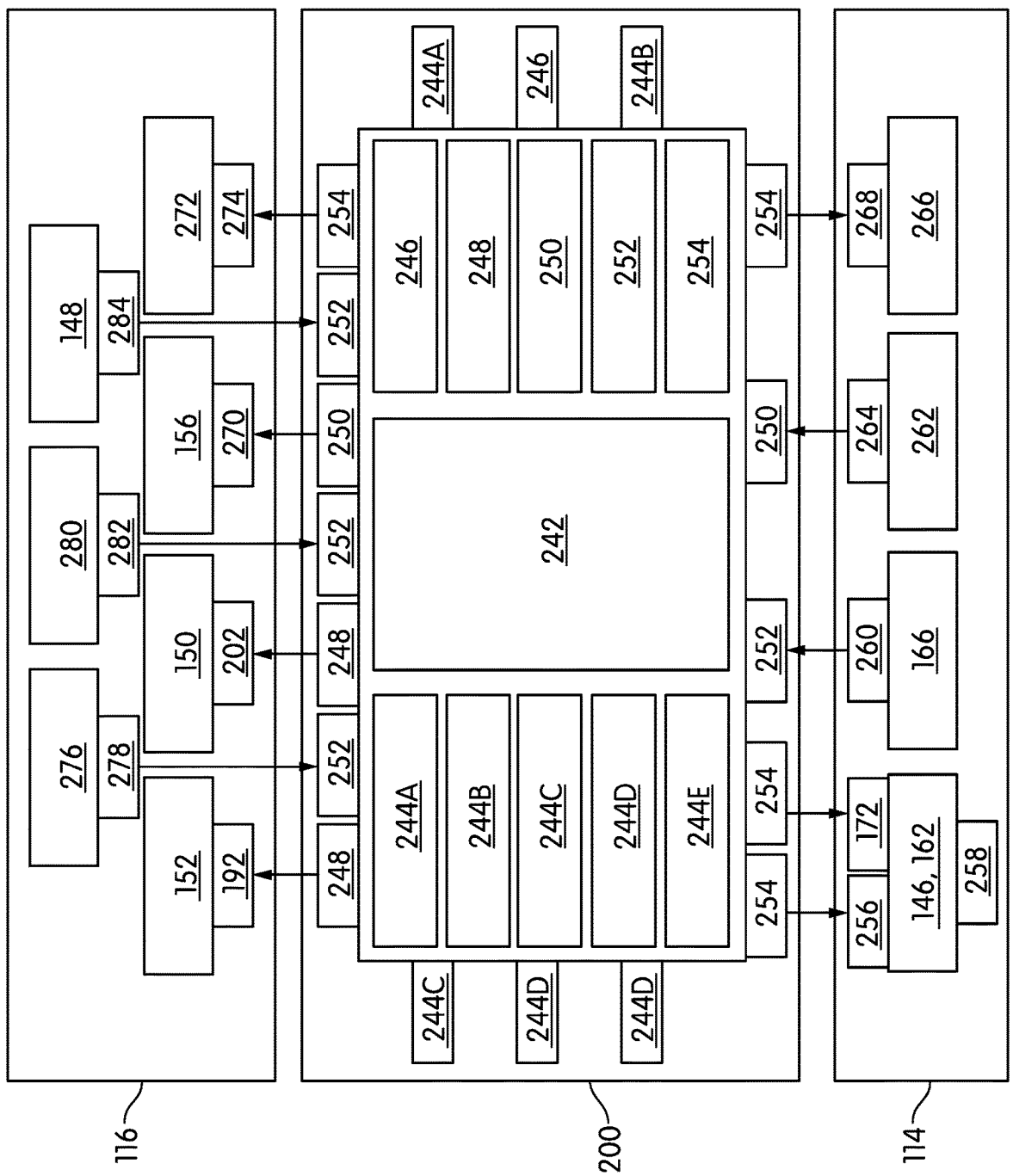
FIG. 15 is a schematic diagram of a controller of an intermediate conveyor assembly coupled to a buffer conveyor subassembly and a spur conveyor subassembly of the intermediate conveyor assembly, according to an embodiment.

FIG. 15 schematically illustrates a controller 200 operatively and directly coupled to buffer conveyor subassembly 114 and spur conveyor subassembly 116 according to an embodiment. As shown in FIG. 15, controller 200 includes a processor 242, for example, a microcontroller such as a PIC microcontroller. Controller 200 includes one or more communication interfaces, for example, a CAN interface 244A, an Ethernet interface 244B, an isolated CAN interface 244C, an isolated RS485 and/or RS422 interface 244D, a USB interface 244E for programming or debugging, or any combination thereof. Controller 200 can also include one or more power supplies 246, for example, a 3.3 VDC or 12.0 VDC power supply.

Controller 200 can also include one or more drivers 248 for controlling one or more drive assemblies of spur conveyor subassembly 116. For example, controller 200 can include one stepper motor driver 248 for controlling drive assembly 192 that moves gripper 188 of spur conveyor subassembly 116, and another stepper motor driver for controlling drive assembly 202 that moves diverter 150.

Controller 200 can further include one or more RFID interfaces 250 for communicating with interfaces of RFID sensors on buffer conveyor subassembly 114 and spur conveyor subassembly 116. For example, controller 200 can include one RFID interface 250 for communicating with an RFID interface 264 of RFID sensor 156 on spur conveyor subassembly 116, and include another RFID interface 250 for communicating with an RFID interface 264 of an optional RFID sensor 262 on buffer conveyor subassembly 114.

Additionally, controller 200 can include one or more sensor interfaces 252 for communicating with interfaces 262 of sensors on buffer conveyor subassembly 114 and spur conveyor subassembly 116. For example, controller 200 can include one sensor interface 252 for communicating with interface 260 of sensor 166 on buffer conveyor subassembly 114, one interface 252 for communicating with an interface 278 of an optional sensor 276 configured to determine whether a carrier is present at position 154, one interface 252 for communicating with an interface 282 of an optional sensor 280 configured to determine the orientation of diverter 150, and one interface 252 for communicating with an interface 284 of sensor 148.

Controller 200 also includes one or more power outputs 254. For example, controller 200 can include four power outputs 254. One power output 254 supplies power to a logic power input 256 of conveyor subassembly 114. One power output 254 supplies power to drive assembly 172 that moves the track defining input and output portions 146 and 162 of buffer conveyor subassembly 114. One power output 254 that supplies power to a power input 268 of optional stop unit 266 of buffer conveyor subassembly 114. And one power output 254 that supplies power to power input 274 of gripper 188.

Any one of the above described components can be omitted from controller 200 or modified based upon the design of buffer conveyor subassembly 114 and spur conveyor subassembly 116.

As shown in FIG. 15, buffer conveyor subassembly 114 can include a CAN interface 258 in some embodiments.

In some embodiments, the controller of host conveyor assembly 102, the controller for processing instrument 104, and the controller for assay instrument 108 can be structured similar to the above described controller 200.

Lab information system 223 manages patient and laboratory information. In some embodiments, lab information system 223 includes a server or host computer having a database, and application software for receiving, storing, and processing patient and laboratory information. In some embodiments, lab information system 223 generates a schedule for processing samples within sample containing receptacles 105 introduced within lab automation system 100 using processing instrument 104 and one or more of assay instruments 108. For example, lab information system 223 can generate a schedule for processing samples within sample containing receptacles 105 introduced within lab automation system 100 that optimize the use of reagents by processing instrument 104 and assay instruments 108, optimize the use (increase the throughput or ensure periods of instrument availability to run random access assays) of processing instrument 104 and assay instruments 108. Lab information system 223 can also generate a schedule for samples within sample containing receptacles 105 introduced within lab automation system 100 that route the samples to the appropriate assay instrument 108 depending on the type of assay to be performed or the type of analyte to be discriminated. According to the generated schedule, lab automation system 100 routes carriers 101 to the appropriate one of assay instruments 108*a*, 108*b*, and 108*c*.

In some embodiments (for example, any of the embodiments of FIGS. 11-13), controller 200 of intermediate conveyor subassembly 133 communicates various information to the controller of the respective assay instrument 108 using communication link 218. For example, controller 200 can communicate one or more of the following types of information to and from the controller of assay instrument 108: (1) the status of assay instrument 108 (e.g., whether assay instrument 108 is (a) idle, (b) ready for processing a sample from processing receptacle 103 coupled to a carrier 101 at processing position 154, (c) processing, or (d) in failure state), (2) the status of intermediate conveyor assembly 133 (e.g., whether intermediate conveyor assembly 133 is (a) idle, (b) whether input portion 146 of buffer conveyor subassembly 114 has carriers 101 for transferring to spur conveyor subassembly 116, (c) whether buffer conveyor subassembly 114 is transferring carriers 101 to spur conveyor subassembly 116, or (d) whether intermediate conveyor assembly 133 is in failure state); (3) the status of processing position 154 in assay instrument 108 (e.g., whether processing position 154 is (a) empty, (b) occupied by a carrier 101 having an unprocessed (not yet aspirated) processing receptacle 103, or (c) occupied by a carrier 101 having a processed (already aspirated) processing receptacle 103); (4) the number of carriers 101 in input portion 146 of buffer conveyor subassembly 114; (5) the number of carriers 101 in output portion 162 of buffer conveyor subassembly 114; (6) the number of carriers 101 output portion 162 of buffer conveyor subassembly 114 can receive from spur conveyor subassembly 116 before being full; (7) information read by sensor 156 from carrier 101, receptacle 103, or both, at processing position 154, for example, an identifier read from an RFID tag on carrier 101; (8) information read by sensors 144 or 148 from carrier 101, receptacle 103, or both, at positions 141 or 147, for example, an identifier read from an RFID tag on carrier 101; (9) a request or confirmation of a new carrier 101 being positioned at processing position 154; and (10) a request or confirmation of whether a receptacle 103 coupled to a carrier 101 is not be processed at processing position 154.

In some embodiments (for example, any of the embodiments of FIGS. 11-13), controller 200 of intermediate conveyor subassembly 133 communicates various information to the controller of host conveyor assembly 102 using communication link 216. Communication link 216 can be CAN, RS485, RS422, USB, or Ethernet communication interfaces. For example, the following information can be communicated between controller 200 and the controller of host conveyor assembly 102: (1) the status of host conveyor assembly 102 (e.g., whether host conveyor assembly 102 is (a) idle or (b) in a failure state); (2) the status of intermediate conveyor assembly 133 (e.g., (a) whether intermediate conveyor assembly 133 is idle, (b) whether input portion 146 of buffer conveyor subassembly 114 is full, (c) whether a carrier 101 is on output portion 162 of buffer conveyor subassembly 114, or (d) whether intermediate conveyor assembly 133 is in a failure state); (3) the number of carriers 101 on input portion 146 of buffer conveyor subassembly 114; (4) the number of carriers 101 that input portion 146 of buffer conveyor subassembly 114 can receive from host conveyor assembly 102 before being full; (5) the number of carriers 101 on output portion 162 of buffer conveyor subassembly 114; (6) information read by sensors 146 or 148 from carrier 101, receptacle 103, or both, at positions 141 or 147, for example, an identifier read from an RFID tag on carrier 101; (7) information read by sensor 156 from carrier 101, receptacle 103, or both, at processing position 154, for example, an identifier read from an RFID tag on carrier 101; (8) a request or confirmation of a carrier 101 being transported to buffer conveyor subassembly 114 from host conveyor assembly 102; and (9) a request or confirmation of a carrier 101 being transferred from buffer conveyor subassembly 114 to host conveyor assembly 102.

E. Exemplary Embodiments of Assay Instruments 108

In some embodiments, one or more of assay instruments 108 are each configured to perform one or more assays on samples contained within cavities defined by assay receptacles 160. For example, the one or more assay instruments 108 can be configured to perform one or more assays that determine the presence of an analyte (for example, a biological analyte such as a pathogenic organism (e.g., bacterium, fungus, or protozoan) or virus) in a sample. In some embodiments, these assays can include performing nucleic acid amplification reactions on the samples. Exemplary nucleic acid amplification reactions include polymerase chain reactions, transcription-based amplification reactions, strand displacement amplification reactions, and ligase chain reactions. In other embodiments, assays can include, for example, nucleic acid detection immunoassays, immunoassays, and chemical assays.

In some embodiments, one assay instrument 108, for example, assay instrument 108a, performs one assay, and another assay instrument 108, for example, assay instrument 108b or 108c performs a different assay.

For example, assay instrument 108a can perform a first assay on samples in assay receptacles 160 that determines the presence of a first type of analyte (e.g., antibodies, antigens, nucleic acids, toxins, or other chemicals), while another assay instrument 108b or 108c is configured to perform a different assay that determines the presence of a second type of analyte different than the first type of analyte. For example, one assay instrument 108 can perform an assay configured to detect the presence of a certain nucleic acid, while another assay instrument 108 performs a different assay to detect the presence of a certain antibody.

In some embodiments, the targeted analyte indicates that a particular bacterium, fungus, protozoan, or virus is present in the sample. In some embodiments, one assay instrument 108 is configured to perform an assay that detects the presence of a first analyte—the presence of which indicates that a particular bacterium, fungus, protozoan, or virus is present in the sample—while another assay instrument 108 is configured to perform a different assay that detects the presence of a different analyte—the presence of which indicates that a different bacterium, fungus, protozoan, or virus is present in the sample. For example, one assay instrument 108 can perform an assay configured to detect the presence of an analyte, the presence of which indicates that a specific virus, for example, a hepatitis C virus (HCV), is present in the sample. And another assay instrument 108 performs a different assay to detect the presence of a different analyte—the presence of which indicates that a different virus, for example, a human immunodeficiency virus (HIV), is present in the sample.

In yet another example, one assay instrument 108 is configured to perform one assay that includes performing a first type of nucleic acid amplification reaction on a sample contained within assay receptacle 160, while another assay instrument 108 is configured to perform a different assay that includes performing a different type of nucleic acid amplification reaction. For example, one assay instrument 108 can perform an assay that includes subjecting samples to conditions (e.g., adding reagent(s) and exposing samples to certain temperature(s) including thermocycling or isothermal conditions) that promote a certain type of nucleic acid amplification reactions, for example, a polymerase chain reaction, while another assay instrument 108 can perform a different assay that includes subjecting samples to conditions (e.g., adding reagent(s) and exposing samples to certain temperature(s) including thermocycling or isothermal conditions) that promote a different type of nucleic acid amplification reaction, for example, a transcription-based amplification reaction. Or for example, one assay instrument 108 performs one assay that includes performing real-time amplification reactions that can be used to determine the presence and amount of a target nucleic acid in a sample in assay receptacle 160, while another assay instrument 108 performs a different assay that includes performing "end-point" amplification assays. Real-time amplification assays can be used to determine the presence and amount of a target nucleic acid in a sample which, by way of example, is derived from a pathogenic organism (e.g., bacterium, fungus, or protozoan) or virus. Real-time amplification assays are often referred to as quantitative assays. By determining the quantity of a target nucleic acid in a sample, a practitioner can approximate the amount or load of the organism or virus in the sample. Real-time amplification assays can also be used to screen blood or blood products intended for transfusion for blood borne pathogens, such as hepatitis C virus (HCV) and human immunodeficiency virus (HIV). Real-time assays can also be used to monitor the efficacy of a therapeutic regimen in a patient infected with a pathogenic organism or virus, or that is afflicted with a disease characterized by aberrant or mutant gene expression. Real-time amplification assays can also be used for diagnostic purposes, as well as in gene expression determinations. Exemplary assay instruments 108 for performing real-time amplification assays are disclosed by Macioszek et al. in U.S. Pat. No. 7,897,337.

In end-point amplification assays, the presence of amplification products containing the target sequence or its complement is determined at the conclusion of an amplification procedure. End-point amplification assays are sometimes referred to as qualitative assays because such assays do not indicate the amount of a target analyte present, but provide a qualitative indication regarding the presence of the target analyte. Exemplary assay instruments 108 for end-point detection are disclosed by Ammann et al. in U.S. Pat. No. 6,335,166.

In some embodiments, one or more of assay instruments 108 are configured to perform assays that capture, amplify, and detect nucleic acids from target organisms in samples.

In some embodiments, assay instruments 108 are configured to perform a target capture process that isolates nucleic acid of the target analyte (e.g., virus, bacterium, fungus, protozoan, mammalian cells, etc.) and purifies nucleic acid for amplification. U.S. application Ser. No. 12/465,323, filed May 13, 2009, to Becker et al. describes various exemplary target capture processes. Assay instruments 108 can be configured to lyse the target analyte, which can be in a variety of biological matrices (including urine and blood), with target capture reagents ("TCR"), whereby the nucleic acid is released.

In some embodiments, assay instruments 108 are configured to perform assays on a sample in a single assays receptacle 160 using common reagents as a one-step process. In some embodiments, assay instruments 108 can detect low-abundance nucleic acid, and use specific controls to obtain quantitative results.

In some embodiments, assay instrument 108 can include a thermal cycler (not shown) for exposing the sample in assay receptacle 160 to temperatures that are cycled between two or more different temperatures.

In some embodiments, assay instruments 108 are each configured to perform a plurality of different assays, for example, different molecular assays, including nucleic acid based amplification assays, nucleic acid detection immunoassays, immunoassays, and/or chemical assays, on a plurality of samples. In some embodiments, assay instruments 108 are each configured perform different target nucleic acid amplification reactions. For example, one assay instrument 108 is configured to perform a first target nucleic acid amplification reaction on a first subset of a plurality of samples, and perform a second, different target nucleic acid amplification reaction on a second subset of the plurality of samples.

In some embodiments, each assay instrument 108 includes a first module configured to perform at least one of the steps of a first target nucleic acid amplification reaction, and a second module configured to perform at least one of the steps of a second target nucleic acid amplification.

In some embodiments, each assay instrument 108 includes various devices configured to receive one or more assay receptacles 160, within each of which is performed one or more steps of a multi-step assay, for example, a nucleic acid test (NAT) designed to detect a virus or organism (e.g., bacterium, fungus, or protozoan). Each assay instrument 108 can be configured to perform one or more of the following processes: adding substances such as sample fluid, reagents (e.g., target capture reagents used in the target capture process to isolate the target nucleic acid (e.g., magnetically responsive particles with immobilized polynucleotides, polynucleotide capture probes, and reagents sufficient to lyse cells containing the targeted nucleic acids), amplification reagents used in nucleic acid amplification reactions to amplify the target nucleic acid or portion thereof (e.g., oligonucleotides for use in producing one or more detectable amplicons for the target nucleic acid), buffers, oils, labels (i.e., a moiety or compound that is detected or leads to a detectable signal such as luminescent or fluorescent compounds), probes (e.g., nucleic acid oligomers that fully or partially hybridize to a target sequence in a nucleic acid, or in an amplicon containing the target sequence or its complement, under conditions that promote hybridization (e.g., under stringent hybridization conditions) to allow detection of the target sequence or amplicon), or any other reagent) and/or removing substances from an assay receptacle 160; agitating an assay receptacle 160 to mix the contents thereof; maintaining and/or altering the temperature of the contents of an assay receptacle 160; heating or chilling the contents of an assay receptacle 160; altering the concentration of one or more components of the contents of an assay receptacle 160; separating or isolating constituent components of the contents of an assay receptacle 160; detecting an electromagnetic signal emission (e.g., light) from the contents of an assay receptacle 160; halting an on-going reaction in an assay receptacle 160; deactivating a nucleic acid in an assay receptacle 160 from further amplification, or any combination thereof.

In some embodiments, each assay instrument 108 can include an assay receptacle 160 input device that includes structure for receiving and holding one or more empty an assay receptacle 160 before assay receptacles 160 are used for performing one or more process steps of an assay, for example, a nucleic acid test. The receptacle input device may comprise a compartment, for example, a drawer or cabinet.

In some embodiments, each assay instrument 108 includes one or more bulk reagent container compartments configured to store one or more bulk containers that hold bulk reagents or hold waste material.

In some embodiments, each assay instrument 108 includes a first bulk reagent container compartment configured to store at least one bulk container that holds a nucleic acid amplification reagent, and a separate second bulk reagent container compartment configured to store at least one bulk container that holds a sample preparation reagent, for example, a target capture reagent. In some embodiments, each assay instrument 108 includes a bulk reagent container compartment that stores both a bulk container that holds a nucleic acid amplification reagent and a bulk container that holds a sample preparation reagent, for example, a target capture reagent.

Each assay instrument 108 can also include a manual sample input bay configured to manually receive and hold processing receptacles 103 containing samples.

Each assay instrument 108 can include at least one automated pipettor 158 configured to transfer fluids, for example, sample fluids, reagents, bulk fluids, waste fluids, etc., to and from assay receptacles 160, other receptacles, and processing receptacles 103 coupled to carriers 101 at processing position 154 within assay instrument 108. Pipettor 158 can be configured for controlled, automated movement and access to the assay receptacles 160, bulk receptacles holding reagents, processing receptacles in the sample input bay, and processing receptacles 103 coupled to carriers 101 at processing position 154.

In some embodiments in which each assay instrument 108 is configured to perform a nucleic acid test, reaction reagents contained within assay instrument 108 may comprise target capture reagents, lysis reagents (e.g., detergents such as lithium lauryl sulfate and sodium dodecyl sulfate), nucleic acid amplification reagents (e.g., the primers, polymerases, nucleoside triphosphates, and salts needed for an amplification), and/or labels.

In some embodiments, each assay instrument 108 includes temperature ramping stations configured to hold one or more assay receptacles 160 in an environment that is maintained at higher or lower than ambient temperatures so as to raise or lower the temperature of the contents of the receptacles. In some embodiments, no reaction is performed on a sample at the temperature ramping station. In some embodiments, the temperature ramping station is used to raise or lower the temperature to the approximate temperature of another station in assay instrument 108 where a subsequent process step will be performed.

In some embodiments, each assay instrument 108 also includes one or more heater modules configured to receive a plurality of assay receptacles 160 and maintain the receptacles in an elevated temperature environment.

Also, in some embodiment in each assay instrument 108 is configured to perform a nucleic acid test, each assay instrument 108 can include sample-processing components, such as magnetic separation wash stations configured to isolate and/or separate a target nucleic acid immobilized on target capture reagent from the remaining contents of assay receptacle 160.

In some embodiments, each assay instrument 108 can further include chilling modules configured to receive one or more assay receptacles 160 and hold the receptacles in a lower than ambient temperature environment so as to reduce the temperature of the contents of the receptacles.

And in some embodiments, each assay instrument 108 can include a detector configured to receive an assay receptacles 160 and detect signals (e.g., optical signals) emitted by the contents of the assay receptacles 160. In one implementation, the detector includes a luminometer for detecting luminescent signals emitted by the contents of an assay receptacles 160 and/or a fluorometer for detecting fluorescent emissions. Each assay instrument 108 can also include one or more signal detecting devices, such as fluorometers, coupled to one or more of the incubators that are configured and controlled to detect, for example, at specified, periodic intervals, signals emitted by the contents of the assay receptacles 160 contained in the incubator while a process, such as nucleic acid amplification, is occurring within the reaction receptacles.

Each assay instrument 108 can include a receptacle transfer device configured to transport assay receptacles 160 to one or more of the incubators, load stations, temperature ramping stations, wash stations, and chilling modules contained within the housing of assay instrument 108.

In some embodiments, each assay instrument 108 is configured to perform an assay that includes the nucleic acid amplification reaction and, in some embodiments, includes measuring fluorescence in real-time (i.e., as the amplification reaction is occurring). Each assay instrument 108 can include a thermal cycler/signal detector, a centrifuge, magnetic elution stations, and reagent pack loading stations. In some embodiments, automated pipettor 158 is configured to have access to the magnetic elution stations and the reagent pack loading stations.

In some embodiments, the bulk reagents within the bulk reagent containers within assay instrument 108 can include a sample preparation reagent (e.g., target capture reagent (TCR), a wash solution, an elution reagent, or any other sample preparation reagent), a reconstitution reagent, or any other required bulk reagent. In some embodiments, the bulk reagent containers hold a quantity of the bulk reagent sufficient to perform between about 50 to 2,000 assays. In some embodiments, the bulk reagents are for performing isothermal nucleic acid amplification reactions.

In some embodiments, each assay instrument 108 can be configured to perform two or more assays that include nucleic acid amplification reactions that require different reagents, including one or more unit-dose reagents—reagents that are unitized into an amount or concentration sufficient to perform one or more steps of a single assay for a single sample. On such assay instrument 108 is described in U.S. application Ser. No. 14/213,900, filed Mar. 14, 2014, to Buse et al.

Results of the assays performed by each of assay instruments 108 may be displayed on an instrument user interface of assay instrument 108 communicated to laboratory information system 223.

F. Exemplary Embodiments of Carrier 101

As used in this application, a "carrier" refers to any device that is configured to operatively couple to at least one receptacle (for example, a sample containing receptacle, a processing receptacle, or any other receptacle) for transporting the at least once receptacle within system 100. Carriers 101 are configured to maintain the orientation of the respective receptacles coupled thereto as the carriers are transported throughout the system. For example, in some embodiments, carriers 101 are pucks having a cylindrical portion defining a recess configured to receive a portion the receptacle. In some puck embodiments, carrier 101 includes a clamping device configured to apply a retaining force to the receptacle placed within the recess of carrier 101 such that the receptacle is retained within the carrier 101.

FIGS. 17 and 18 illustrate an embodiment of carrier 101. As shown in FIG. 17, carrier 101 includes a cylindrical main body 286 having a top end portion 288 and a bottom end portion 290. In other embodiments, main body 286 can have non-cylindrical shapes.

In some embodiments, main body 286 is sized to fit on each of intermediate conveyor assembly 106, host conveyor assembly 102, and intermediate conveyor assemblies 133A-133C. When carrier 101 is placed on intermediate conveyor assembly 106, host conveyor assembly 102, or intermediate conveyor assemblies 133A-133C, bottom end portion 290 is adjacent, for example, a movable track of respective intermediate conveyor assembly 106, host conveyor assembly 102, and intermediate conveyor assemblies 133A-133C.

In some embodiments, top end portion 288 defines a recess 292, which can be circular in some embodiments. Recess 292 is configured to receive at least one movable retaining member 294. For example, as shown in FIG. 17, circular recess 292 is configured to receive three movable retaining members 294. The retaining members 294 each have annular sector shape (when viewed in plan) and collectively form an annulus defining an interior recess portion 296, which can be circular in some embodiments, configured to receive a portion, for example, a bottom portion of a processing receptacle 103 to couple the processing receptacle 103 to the carrier 101. In some embodiments, each retaining member 294 includes a tapered surface 308 that aligns receptacle 103 with the center of recess portion 296 when receptacle 103 is being inserted in recess portion 296. In other embodiments, carrier 101 can include less than three or more than three movable retaining members 294. And in other embodiments, retaining members 294 can have other non-annular sector shapes when viewed in plan. In yet other embodiments, retaining members 294 can define an interior recess portion 296 that has a non-circular shape. In some embodiments, the depth of recess portion 296 and the placement of a machine readable label, for example, a barcode, on receptacle 103 are such that when the bottom portion of a receptacle 103 is inserted within recess portion 296, the machine readable label on receptacle 103 is not obstructed by any portion carrier 101 and such that a sensor, for example, a barcode reader, can read the label on receptacle 103.

In some embodiments, carrier 101 includes one or more retaining fasteners (for example, as shown in FIGS. 17 and 18, a screw and corresponding washer) configured to secure retaining members 294 within recess 292 of carrier 101. In some embodiments, retaining fasteners are stainless steel or a non-ferrous material so as to not interfere with any RFID tag on carrier 101 or receptacle 103. Correspondingly, in some embodiments, all components of carrier 101 are composed of a non-ferrous material so as to not interfere with any RFID tag on carrier 101 or receptacle 103.

Retaining members 294 are biased toward a center of recess portion 296 such that each retaining member 294 applies a force to a bottom portion of processing receptacle 103 inserted in recess portion 296, generating an axial retaining force (e.g., via friction) that secures receptacle 103 to carrier 101. In some embodiments, the magnitude of the applied force to the bottom portion of processing receptacle 103 is sufficient to generate an axial retaining force that secures receptacle 103 to carrier 101 as carrier 101 is transported by any one of intermediate conveyor assembly 106, host conveyor assembly 102, and intermediate conveyor assemblies 133A-133C. In some embodiments, the magnitude of the applied force to the bottom portion of processing receptacle 103 is not so great as to squeeze receptacle 103 upward and out of recess portion 296. In some embodiments, the sum of the axial retaining forces generated by retaining members 294 and the axial retaining forces generated by gripper 188 via second portions 193 of prongs 189 (as described above) is equal to or greater than any axial force applied to receptacle 103 in the opposite direction of the generated retaining forces (for example, a force applied to receptacle 103 as the distal end of pipettor 158 is removed from receptacle 103). In some embodiments, this sum of axial retaining forces applied to receptacle 103 is equal to or greater than about four pounds. In some embodiments, this sum of axial retaining forces applied to receptacle 103 is equal to or greater than about 6 pounds.

In some embodiments, carrier 101 includes a biasing device that biases retaining members 294 toward the center of recess portion 296 to apply the forces to the bottom portion of processing receptacle 103 inserted in recess portion 296. For example, in some embodiments, each retaining member 294 can define one or more periphery grooves 304 configured to receive respective one or more garter springs 306 that bias each retaining member 294 toward the center of recess portion 296 to apply forces to the bottom portion of processing receptacle 103 inserted in recess portion 296.

In some embodiments, movable retaining members 294 have a radial stroke such that inner recess portion 296 can have a varying size that accommodates receptacles 103 of varying diameters. For example, in some embodiments, inner recess portion 296 can accommodate receptacles 103 having diameters varying from about 8 mm to about 20 mm, including receptacles 103 having a diameter of 12 mm or 16 mm.

In some embodiments, main body 286 defines one or more periphery, circumferential grooves. For example, as shown in FIGS. 17 and 18, main body 286 defines a lower groove 300. Lower groove 300 can be configured to mate with corresponding protrusions on any one of intermediate conveyor assembly 106, host conveyor assembly 102, and intermediate conveyor assemblies 133A-133C to prevent carrier 101 and the receptacle 103 coupled thereto from tipping over as carrier 101 is transported along the respective conveyor assembly. For example, one or more guide rails of intermediate conveyor assembly 106, host conveyor assembly 102, and/or intermediate conveyor assemblies 133A-133C can define a protrusion that is received within lower groove 300 of carrier 101 as carrier 101 is transported along the respective conveyor assembly. When the protrusion on the guide rail is received within lower groove 300 of carrier 101 the carrier is substantially prevented from tipping over relative to the track(s) of the respective intermediate conveyor assembly 106, host conveyor assembly 102, and/or intermediate conveyor assemblies 133A-133C, thereby also preventing receptacle 103 coupled thereto from tipping over.

Main body 286 can also define a second, upper groove 302. Upper groove 302 can be configured to mate with corresponding protrusions on gripper 188 to hold carrier 101 down as a distal end of an aspirator 158 is removed from receptacle 103 when carrier 101 is at the processing position 154 of assay instrument 108. For example, first portion 191 of each prong 189 of gripper 188 can form a protrusion that mates with groove 302 of carrier 101 to hold carrier 101 down to base 186 within spur conveyor 116 of intermediate conveyor assembly 133.

As shown in FIGS. 18, 29, 30, and 37, upper and lower grooves 301 and 302 can have various shapes, sizes, and orientations.

In some embodiments, bottom end portion 290 defines a recess 310 configured to receive one or more components. For example, recess 310 can be shaped to closely receive one or more RFID tags or any other types of transponders. In some embodiments, recess 310 includes a first portion 312 shaped to receive first type of component and a second portion 314 shaped to receive a different type of component. For example, as shown in FIG. 17, first portion 312 can have a cylindrical shape configured to closely receive an RFID tag that operates at one frequency, and second portion 314 can have a rectangular shape configured to closely receive a different type of RFID tag that operates at a different frequency. As shown in FIG. 17, second portion 314 of recess 310 can extend from a surface defining first portion 312 of recess 310 toward top end portion 288 of main body 286. In some embodiments, the center of first portion 312 of recess 310 and the center of second portion 314 of recess 310 are coaxial with each other and, in some embodiments, are coaxial with the center of recess portion 296 that receives receptacle 103.

This application also discloses new, original, and ornamental designs for a carrier 101, reference being had to, for example, the designs of FIGS. 27-37, forming a part thereof. In FIGS. 27-37, the broken lines show portions of the sample carrier that form no part of the disclosed designs.

2. Exemplary Embodiments of Use and Sample Processing Methods

Embodiments of processing samples using one or more of processing instrument 104, intermediate conveyor assembly 106, host conveyor assembly 102, intermediate conveyor assemblies 133, and assay instruments 108 will now be described. In some embodiments, processing instrument 104 reads information (e.g., an identifier) from carrier 101, processing receptacle 103, or both, using, for example, sensor 138, and the controller of processing instrument 104 transmits the read information, for example, an identifier, of carrier 101, processing receptacle 103, or both, to lab information system 223 via communication link(s) 228. Lab information system 223 can then associate the sample dispensed into receptacle 103 with the identifier on carrier 101, receptacle 103, or both, read by a sensor. Afterwards, intermediate conveyor assembly 106 can transport the carrier 101 and processing receptacle 103 coupled thereto from processing instrument 104 to host conveyor assembly 102. These steps can then be repeated for one or more additional processing receptacles 103 and carriers 101.

As shown in FIG. 1, host conveyor assembly 102 transports the carriers 101 and receptacles 103 coupled thereto (which were received from intermediate conveyor assembly 106) along first portion 118 toward assay instrument 108a. As carriers 101 pass sensor 144, sensor 144 reads information from carrier 101, receptacle 103, or both, and transmits a signal to a controller of host conveyor assembly 102 that includes the read information. The controller of host conveyor assembly 102 can then determine whether the read information, for example, an identifier, is associated with a first sample on which assay instrument 108a is scheduled to perform an assay on the sample in the receptacle 103. This determination can be based on information stored in the laboratory information system 223. If the read information from carrier 101 or receptacle 103 passing sensor 144 is associated with a sample on which assay instrument 108a is scheduled to perform an assay, the controller of host conveyor assembly 102 then sends a control signal to diverter 142a to divert the respective carrier 101 from host conveyor assembly 102 to input portion 146 of buffer conveyor subassembly 114 of intermediate conveyor assembly 133a.

If the read information from carrier 101 or receptacle 103 passing sensor 144a is not associated with a sample on which assay instrument 108a is scheduled to perform an assay, the controller of host conveyor assembly 102 adjusts the control signal transmitted to diverter 142a, which then divert the respective carrier 101 to a downstream portion 145a of host conveyor assembly 102 that bypasses intermediate conveyor assembly 133a and assay instrument 108a. Host conveyor assembly 102 then continues to transport the carrier 101 toward the next assay instrument 108b.

As the next carrier 101 passes sensor 144a, sensor 144a reads information from that carrier 101, receptacle 103 coupled to that carrier 101, or both, and transmits a signal to the controller of host conveyor assembly 102 that includes the read information. The controller of host conveyor assembly 102 can then determine whether the read information, for example, an identifier, is associated with a sample on which assay instrument 108a is scheduled to perform an assay based on information stored in the laboratory information system 223. If the read information is associated with a sample on which assay instrument 108a is scheduled to perform an assay, the controller of host conveyor assembly 102 then sends a control signal to diverter 142a to divert the next carrier 101 from host conveyor assembly 102 to input portion 146a of buffer conveyor subassembly 114a of intermediate conveyor assembly 133a. If the read information from the subsequent carrier 101 is not associated with a sample on which assay instrument 108a is scheduled to perform an assay, the controller of host conveyor assembly 102 adjusts the control signal transmitted to diverter 142a to divert the subsequent carrier 101 to a downstream portion 145a of host conveyor assembly 102 that bypasses intermediate conveyor assembly 133a and assay instrument 108. Host conveyor assembly 102 then continues to transport the subsequent carrier 101 toward the next assay instrument 108b.

Host conveyor assembly 102 can divert a plurality of carriers 101 to input portion 146a of buffer conveyor subassembly 114a until input portion 146a of buffer conveyor subassembly 114 is full. At that point, the controller of host conveyor assembly 102 will continue to divert carriers 101 to downstream portion 145a of host conveyor assembly 102 regardless of whether the sample contained within receptacle 103 coupled to carrier 101 is scheduled for an assay to be performed by assay instrument 108a until space is available on input portion 146a of buffer conveyor subassembly 114a to accept additional carriers 101.

Once a carrier 101 is diverted from host conveyor assembly 102 to input portion 146a of buffer conveyor subassembly 114a, the controller of host conveyor assembly 102 provides a notification to controller 200a of intermediate conveyor assembly 133a that a carrier 101 was diverted. And in some embodiments, the controller of host conveyor assembly 102 transmits information about the diverted carrier 101, for example, an identifier of the carrier 101, receptacle 103, or both, to controller 200a.

Once a predetermined minimum number of carriers 101 have been queued on input portion 146a, controller 200a can notify the controller of assay instrument 108a that the predetermined minimum number of carriers 101 and, thus, samples in processing receptacles 103 are available for processing by assay instrument 108a. In some embodiments, the predetermined minimum number of carriers 101 is at least five carriers 101. In other embodiments, the predetermined minimum number of carriers 101 is less than five. In some embodiments, the predetermined minimum number of carriers 101 equals the number of cavities defined by a signal assay receptacle 160. For example, if a single assay receptacle 160 defines five cavities for receiving five samples, the predetermined minimum number of carriers equals five.

Input portion 146a transports diverted carriers 101 towards position 147 on buffer conveyor subassembly 114a and queues a plurality of carriers 101 until assay instrument 108a is ready to start processing samples contained in receptacles 103 coupled to carriers 101. In some embodiments, as a carrier 101 on buffer conveyor subassembly 114a passes sensor 148a, sensor 148a reads information from the passing carrier 101, receptacle 103, or both, and transmits a signal to controller 200a of intermediate conveyor assembly 133a that includes the read information. Controller 200a of intermediate conveyor assembly 133a can then determine whether the read information, for example, an identifier, is associated with or matches the information transmitted from the controller of host conveyor assembly 102 to intermediate conveyor assembly 133a about the respective diverted carrier 101. If the read information matches or is associated with the transmitted information, controller 200a of intermediate conveyor assembly 133a sends a control signal to diverter 150a to divert the respective carrier 101 from input portion 146a of buffer conveyor subassembly 114a to spur conveyor subassembly 116a. If the read information does not match or is not associated with the transmitted information, controller 200a of intermediate conveyor assembly 133a adjusts the control signal to diverter 150a to divert the carrier 101 from input portion 146a of buffer conveyor subassembly 114a directly to output portion 162a of buffer conveyor subassembly 114a, bypassing spur conveyor subassembly 116a.

After being transferred to spur conveyor subassembly 116a of intermediate conveyor assembly 133a, spur conveyor subassembly 116a transports the carrier 101 to processing position 154a within assay instrument 108a. For example, gripper 188 clamps the carrier 101 at position 153a, and moves towards processing position 154a until the carrier 101 is at position 154a. Sensor 156a can then read information from the carrier 101, receptacle 103 coupled thereto, or both, when carrier 101 is at processing position 154a. Sensor 156a can also transmit a signal to controller 200a of intermediate conveyor assembly 133 that includes the read information. Controller 200a of intermediate conveyor assembly 133a can then determine whether the read information, for example, an identifier, is associated with a sample on which assay instrument 108a is scheduled to perform an assay. This determination can be based on information stored in the laboratory information system 223. In some embodiments, another sensor of spur conveyor subassembly detects whether carrier is indeed at position 154a. If the read information is associated with a sample on which assay instrument 108a is scheduled to perform an assay, controller 200a then sends a notification to the communication interface of the controller of assay instrument 108 that processing of the sample within the processing receptacle 103 coupled to carrier 101 located at processing position 154 can begin. As explained above, pipettor 158a of assay instrument 108a can aspirate at least a portion of a sample from receptacle 103 coupled to carrier 101 at processing position 154a, and pipettor 158a can subsequently dispense the aspirated sample portion into a cavity defined by assay receptacle 160a. After assay instrument 108a completes the processing of samples within processing receptacle 103 coupled to carrier 101 at processing position 154a, the communication interface of the controller of assay instrument 108 sends a notification to controller 200a of intermediate conveyor assembly 133a that processing is complete, and spur conveyor spur conveyor subassembly 116a then transports the carrier 101 away from processing position 154a and back to position 153 on spur conveyor subassembly 116a. Diverter 150a can then transport the carrier 101 to output portion 162a of buffer conveyor subassembly 114a. In some embodiments, the total time it takes to (1) transport carrier 101 from position 153a to processing position 154a using spur conveyor subassembly 116a, (2) process the sample contained with the sample receptacle 103 coupled to the carrier 101 at position 154a (i.e., aspirate at least a portion of a sample from receptacle 103 using automated pipettor 158a of assay instrument 108a), and (3) transport the carrier 101 from processing position 154 to position 153 using spur conveyor subassembly 116 takes less than or equal to about 1 minute.

If the information read by sensor 156 is not associated with a sample on which assay instrument 108a is scheduled to perform an assay, controller 200a notifies the communication interface of the controller of assay instrument 108 that processing should not begin, and spur conveyor subassembly 116a transports the carrier 101 back to position 153a. Diverter 150a then transports the carrier to output portion 162a of buffer conveyor subassembly 114a. The steps of transporting a carrier 101 from position 153a to processing position 154a using spur conveyor subassembly 116, processing the sample contained with the sample receptacle 103 coupled to the carrier 101 at position 154a, and transporting the carrier 101 from processing position 154a to position 153a using spur conveyor subassembly 116a is repeated as long as long as minimum number of carriers 101 are on the input portion 146a of buffer conveyor subassembly 114a, the output portion 162a of buffer conveyor subassembly 114a is not full, and consumables, waste space, and reagents are available within assay instrument 108a.

Output portion 162a of buffer conveyor subassembly 114a transports the carrier 101 received from spur conveyor subassembly 116a to position 167a. When sensor 166a detects the presence of a carrier 101 at position 167a, diverter 164a is actuated and transports the carrier 101 back to host conveyor assembly 102.

Host conveyor assembly 102 continues to transport the carriers 101 that were either bypassed by assay instrument 108a toward the next assay instrument 108b or received from output portion 162a of buffer conveyor subassembly 114a of intermediate conveyor assembly 133a toward the next assay instrument 108b. As carriers 101 approach assay instrument 108b and pass sensor 144b, sensor 144b reads information from the carriers 101, receptacles 103, or both, and sensor 144b transmits a signal to the controller of host conveyor assembly 102 that includes the read information. The controller of host conveyor assembly 102 then determines whether the read information, for example, an identifier, is associated with samples on which assay instrument 108b is scheduled to perform an assay based on information stored in the laboratory information system 101. If this read information is associated with samples on which assay instrument 108b is scheduled to perform an assay, the controller of host conveyor assembly 102 then sends a control signal to diverter 142b to divert the respective carriers 101 from host conveyor assembly 102 to input portion 146b of buffer conveyor subassembly 114b of intermediate conveyor assembly 133b. If the read information is not associated with samples on which assay instrument 108b is scheduled to perform an assay, the controller of host conveyor assembly 102 can adjust the control signal transmitted to diverter 142b to divert the respective carriers 101 to a downstream portion 145b of host conveyor assembly 102 that bypasses intermediate conveyor assembly 133b and assay instrument 108b. Host conveyor then continues to transport the bypassed carriers 101 toward the next assay instrument 108c.

The step of diverting carriers from host conveyor assembly 102 to input portion 146b of buffer conveyor subassembly 114b of intermediate conveyor assembly 133b can continue for subsequent carriers 101 passing sensor 144b until input portion 146b of buffer conveyor subassembly 114b is full. At that point, the controller of host conveyor assembly 102 will continue to divert carriers 101 to portion 145b of host conveyor assembly 102 regardless of whether the sample contained within receptacle 103 coupled to the carrier 101 is scheduled for an assay to be performed by assay instrument 108b until space is available on input portion 146b of buffer conveyor subassembly 114b to accept additional carriers 101. In some embodiments, loading input portion 146b of buffer conveyor subassembly 114b continues until at least a predetermined minimum number of carriers, for example, five carriers 101, have been queued on input portion 146b. Once a minimum number of carriers 101 have been queued, controller 200b can notify the controller of assay instrument 108 that the predetermined minimum number of carriers 101 (and thus samples in processing receptacles 103) available for processing by assay instrument 108. Once diverted to input portion 146b of buffer conveyor subassembly 114b, the controller of host conveyor assembly 102 provides a notification to controller 200b of intermediate conveyor assembly 133b that a carrier 101 was diverted to input portion 146b and, in some embodiments, transmits information about the diverted carrier 101, for example, an identifier of the carrier 101, receptacle 103, or both, to controller 200b. Buffer conveyor subassembly 114b transports the carrier 101 toward position 147b on and queues the carrier. In some embodiments, as a carrier 101 on buffer conveyor subassembly 114b passes sensor 148b, sensor 148b reads information from a respective carrier 101, receptacle 103, or both, and transmits a signal to controller 200b of intermediate conveyor assembly 133b that includes the read information. Controller 200b can then determine whether the read information, for example, an identifier, is associated with the information transmitted from the controller of host conveyor assembly 102 to intermediate conveyor assembly 133 about the diverted carrier 101. If the read information matched the transmitted information, controller 200b of intermediate conveyor assembly 133b sends a control signal to diverter 150b to divert the respective carrier 101 from input portion 146b of buffer conveyor subassembly 114b to spur conveyor subassembly 116b. If the read information does not match the transmitted information, controller 200b of intermediate conveyor assembly 133b adjusts the control signal to diverter 150b to divert the carrier 101 from input portion 146b of buffer conveyor subassembly 114b directly to output portion 162b of buffer conveyor subassembly 114b, bypassing spur conveyor subassembly 116b.

If a carrier 101 is diverted to spur conveyor subassembly 116b of intermediate conveyor assembly 133b, spur conveyor subassembly 116b transports the carrier 101 to processing position 154b within assay instrument 108b. For example, gripper 188 clamps the carrier 101 at position 153b and moves towards position 154b until the carrier 101 is at position 154b. Sensor 156b can then read information from the carrier 101, receptacle 103, or both, when carrier 101 is at processing position 154b and transmits a signal to controller 200b of intermediate conveyor assembly 133b that includes the read information. Controller 200b can then determine whether the information read by sensor 144*b*, for example, an identifier, is associated with a sample on which assay instrument 108*b* is scheduled to perform an assay. This determination can be based on information stored in the laboratory information system 223. In some embodiments, another sensor of spur conveyor subassembly 116*b* detects whether carrier is indeed at position 154*b*. If the read information is associated with a sample on which assay instrument 108*b* is scheduled to perform an assay, controller 200*b* then sends a notification to the communication interface of the controller of assay instrument 108*b* that processing of the sample within the receptacle 103 coupled to carrier 101 located at processing position 154*b* can begin. After assay instrument 108*b* completes the processing of the sample within processing receptacle 103 coupled to carrier 101 at processing position 154*b*, the communication interface of the controller of assay instrument 108 sends a notification to controller 200*b* of intermediate conveyor assembly 133*b* that processing is complete, and spur conveyor subassembly 116*b* transports the carrier 101 back to position 153*b*. Diverter 150*b* then transports the carrier 101 to output portion 162*b* of buffer conveyor subassembly 114*b*.

If the information read by sensor 156*b* is not associated with a sample on which assay instrument 108*b* is scheduled to perform an assay, controller 200*b* notifies the communication interface of the controller of assay instrument 108*b* that processing should not begin, and spur conveyor subassembly 116*b* transports the carrier 101 back to position 153*b*, and diverter 150*b* transfers the carrier 101 to output portion 162*b* of buffer conveyor subassembly 114*b*. The step of transporting a carrier 101 from position 153*b* to processing position 154*b* using spur conveyor subassembly 116*b*, processing the sample contained within the sample receptacle 103 coupled to the carriers 101 at position 154*b*, and transporting the carrier 101 from processing position 154*b* to position 153*b* using spur conveyor subassembly 116*b* is repeated as long as (1) a predetermined minimum number of carriers 101 are on the input portion 146*b* of buffer conveyor subassembly 114*b*, (2) the output portion 162*b* of buffer conveyor subassembly 114*b* is not full, and (3) consumables, waste space, and reagents are available within assay instrument 108*b*.

Output portion 162*b* of buffer conveyor subassembly 114*b* transports the carriers 101 received from spur conveyor subassembly 116*b* to position 167*b*. When sensor 166*b* detects the presence of a carrier 101 at position 167*b*, diverter 164*b* is actuated and transports the carrier 101 back to host conveyor assembly 102.

Host conveyor assembly 102 transports the carriers 101 either bypassed by assay instrument 108*b* or received from output portion 162*b* of buffer conveyor subassembly 114*b* toward the next assay instrument 108*c*. As carriers 101 approach diverter 122, sensor 126 detects the presence of a carrier 101 within a recess defined by diverter 122, and the controller of host conveyor assembly 102 in communication with sensor 126 actuates diverter 122 to transfer the carrier 101 to second portion 120 of host conveyor assembly 102. Second portion 120 of host conveyor assembly continues to transport carriers 101 toward assay instrument 108*c* and such that carriers 101 pass sensor 144*c*. Sensor 144*c* reads information (e.g., an identifier) from the carriers 101, receptacles 103, or both, and transmits a signal to the controller of host conveyor assembly 102 that includes the read information. The controller of host conveyor assembly 102 then determines whether the read information, for example, an identifier, is associated with samples on which assay instrument 108*c* is scheduled to perform an assay. This determination can be based on information stored in the laboratory information system 223. If this read information is associated with a sample on which assay instrument 108*c* is scheduled to perform an assay, the controller of host conveyor assembly 102 then sends a control signal to diverter 142*c* to divert the respective carrier 101 from host conveyor assembly 102 to input portion 146*c* of buffer conveyor subassembly 114*c* of intermediate conveyor assembly 133*c*. If the read information is not associated with a sample on which assay instrument 108*c* is scheduled to perform an assay, the controller of host conveyor assembly 102 adjusts the control signal transmitted to diverter 142*c*, which diverts the respective carrier 101 to a portion 145*c* of host conveyor assembly 102 that bypasses intermediate conveyor assembly 133*c* and assay instrument 108*c*. Host conveyor then continues to transport the bypassed carriers 101 toward diverter 124 and the next assay instrument 108*a*.

Host conveyor assembly 102 can continue to divert carriers 101 from host conveyor assembly 102 to input portion 146*c* of buffer conveyor subassembly 114*c* of intermediate conveyor assembly 133*c* until input portion 146*c* of buffer conveyor subassembly 114*c* is full. At that point, the controller of host conveyor assembly 102 will continue to divert carriers 101 to downstream portion 145*c* of host conveyor assembly 102 regardless of whether the sample contained within receptacle 103 coupled to the carrier 101 is scheduled for an assay to be performed by assay instrument 108*c*, until space is available on input portion 146*c* of buffer conveyor subassembly 114*c* to accept additional carriers 101.

Once a carrier 101 is diverted from host conveyor assembly 102 to input portion 146*a* of buffer conveyor subassembly 114*a*, the controller of host conveyor assembly 102 provides a notification to controller 200*a* of intermediate conveyor assembly 133*a* that a carrier 101 was diverted. And in some embodiments, the controller of host conveyor assembly 102 transmits information about the diverted carrier 101, for example, an identifier of the carrier 101, receptacle 103, or both, to controller 200*a*.

Once a predetermined minimum number of carriers 101 have been queued on input portion 146*c*, controller 200*c* can notify the controller of assay instrument 108*c* that the predetermined minimum number of carriers 101 and, thus, samples in processing receptacles 103 are available for processing by assay instrument 108*c*. In some embodiments, the predetermined minimum number of carriers 101 is at least five carriers 101. In other embodiments, the predetermined minimum number of carriers 101 is less than five. In some embodiments, the predetermined minimum number of carriers 101 equals the number of cavities defined by a signal assay receptacle 160*c*. For example, if a single assay receptacle 160*c* defines five cavities for receiving five samples, the predetermined minimum number of carriers equals five.

Input portion 146*c* transports diverted carriers 101 towards position 147*c* on buffer conveyor subassembly 114*c* and queues a plurality of carriers 101 until assay instrument 108*c* is ready to start processing samples contained in receptacles 103 coupled to carriers 101. In some embodiments, as a carrier 101 on buffer conveyor subassembly 114*c* passes sensor 148*c*, sensor 148*c* reads information from the passing carrier 101, receptacle 103, or both, and transmits a signal to controller 200*c* of intermediate conveyor assembly 133*c* that includes the read information. Controller 200*c* of intermediate conveyor assembly 133*c* can then determine whether the read information, for example, an identifier, is associated with or matches the information transmitted from the controller of host conveyor assembly 102 to intermediate conveyor assembly 133c about the respective diverted carrier 101. If the read information matches or is associated with the transmitted information, controller 200c of intermediate conveyor assembly 133c sends a control signal to diverter 150c, which diverts the respective carrier 101 from input portion 146c of buffer conveyor subassembly 114c to spur conveyor subassembly 116c. If the read information does not match or is not associated with the transmitted information, controller 200c of intermediate conveyor assembly 133c adjusts the control signal to diverter 150c, which divert the carrier 101 from input portion 146c of buffer conveyor subassembly 114c directly to output portion 162c of buffer conveyor subassembly 114c, bypassing spur conveyor subassembly 116c.

After being transferred to spur conveyor subassembly 116c of intermediate conveyor assembly 133b, spur conveyor subassembly 116c transports the carrier 101 to processing position 154c within assay instrument 108c. For example, gripper 188 clamps the carrier 101 at position 153c, and moves towards processing position 154c until the carrier 101 is at position 154c. Sensor 156c can then read information from the carrier 101, receptacle 103 coupled thereto, or both, when carrier 101 is at processing position 154c. Sensor 156c can also transmit a signal to controller 200c of intermediate conveyor assembly 133 that includes the read information. Controller 200c of intermediate conveyor assembly 133c can then determine whether the read information, for example, an identifier, is associated with a sample on which assay instrument 108c is scheduled to perform an assay. This determination can be based on information stored in the laboratory information system 223. In some embodiments, another sensor of spur conveyor subassembly detects whether carrier 101 is indeed at position 154c. If the read information is associated with a sample on which assay instrument 108c is scheduled to perform an assay, controller 200c then sends a notification to the communication interface of the controller of assay instrument 108 that processing of the sample within the processing receptacle 103 coupled to carrier 101 located at processing position 154 can begin. As explained above, pipettor 158c of assay instrument 108c can aspirate at least a portion of a sample from receptacle 103 coupled to carrier 101 at processing position 154c, and pipettor 158c can subsequently dispense the portion of the aspirated sample into a cavity defined by assay receptacle 160c. After assay instrument 108c completes the processing of samples within processing receptacle 103 coupled to carrier 101 at processing position 154c, the communication interface of the controller of assay instrument 108 sends a notification to controller 200c of intermediate conveyor assembly 133c that processing is complete, and spur conveyor spur conveyor subassembly 116c then transports the carrier 101 away from processing position 154c and back to position 153 on spur conveyor subassembly 116c. Diverter 150c can then transport the carrier 101 to output portion 162c of buffer conveyor subassembly 114c. In some embodiments, the total time it takes to (1) transport carrier 101 from position 153c to processing position 154c using spur conveyor subassembly 116c, (2) process the sample contained with the sample receptacle 103 coupled to the carrier 101 at position 154c (i.e., aspirate at least a portion of a sample from receptacle 103 using automated pipettor 158c of assay instrument 108a), and (3) transport the carrier 101 from processing position 154 to position 153 using spur conveyor subassembly 116 takes less than or equal to about 1 minute.

If the information read by sensor 156 is not associated with a sample on which assay instrument 108c is scheduled to perform an assay, controller 200c notifies the communication interface of the controller of assay instrument 108 that processing should not begin, and spur conveyor subassembly 116c transports the carrier 101 back to position 153c. Diverter 150c then transports the carrier to output portion 162c of buffer conveyor subassembly 114c. The steps of transporting a carrier 101 from position 153c to processing position 154c using spur conveyor subassembly 116, processing the sample contained with the sample receptacle 103 coupled to the carrier 101 at position 154c, and transporting the carrier 101 from processing position 154c to position 153c using spur conveyor subassembly 116c is repeated as long as long as minimum number of carriers 101 are on the input portion 146c of buffer conveyor subassembly 114c, the output portion 162c of buffer conveyor subassembly 114c is not full, and consumables, waste space, and reagents are available within assay instrument 108c.

Output portion 162c of buffer conveyor subassembly 114c transports the carrier 101 received from spur conveyor subassembly 116c to position 167c. When sensor 166c detects the presence of a carrier 101 at position 167c, diverter 164c is actuated and transports the carrier 101 back to host conveyor assembly 102.

Host conveyor assembly 102 continues to transport the carriers 101 either bypassed by assay instrument 108c or received from output portion 162c of buffer conveyor subassembly 114a toward the next assay instrument 108a. As carriers 101 approach diverter 124, sensor 128 detects the presence of a carrier 101 within a recess defined by diverter 124, and the controller of host conveyor assembly 102 in communication with sensor 128 actuates diverter 124, which transfers the carrier to first portion 118 of host conveyor assembly 102. First portion 118 of host conveyor assembly 102 continues to transport carriers 101 toward assay instrument 108a.

Figure 16:
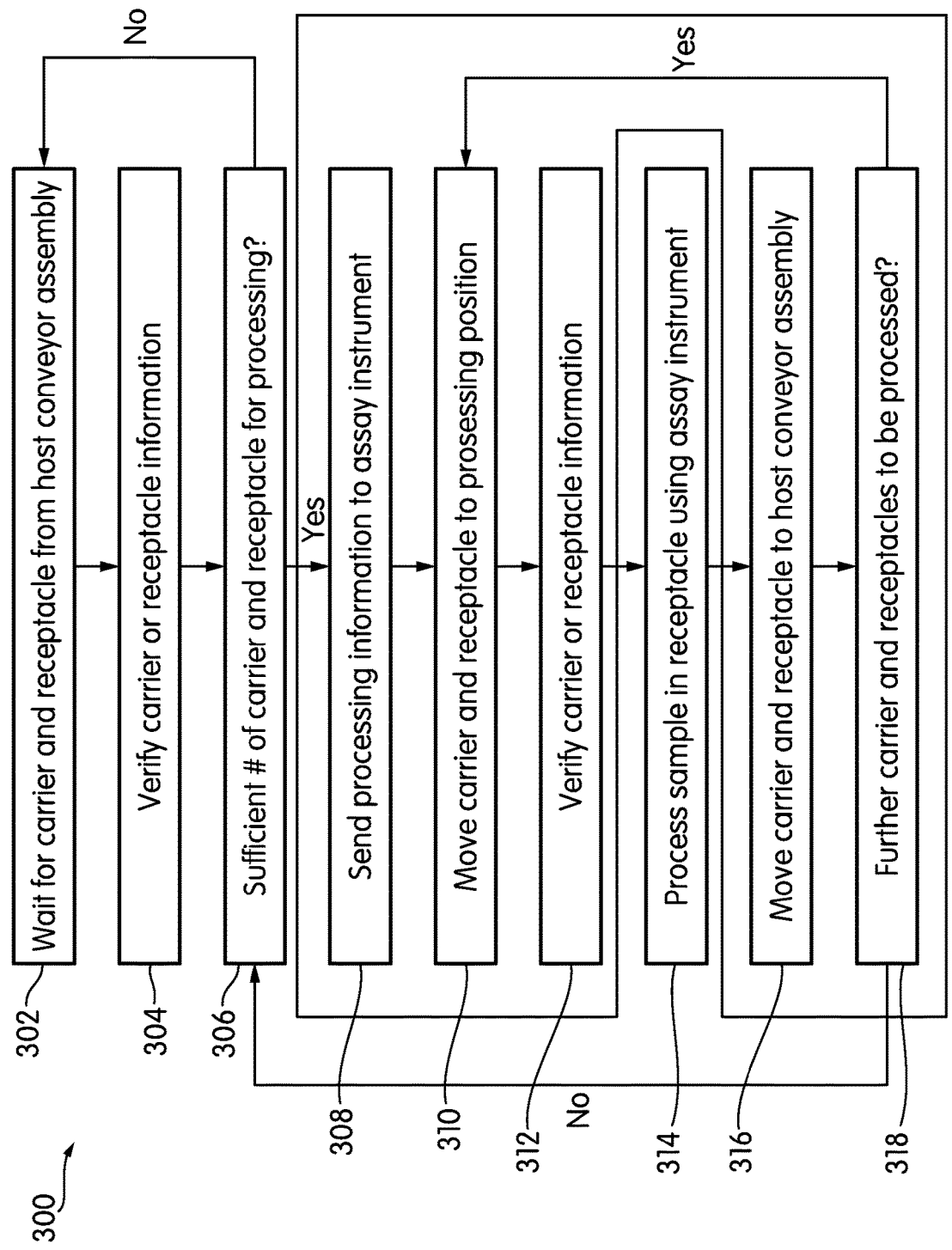
FIG. 16 is a block diagram of a laboratory automated method, according to an embodiment.

FIG. 16 illustrates an exemplary embodiment of processing carriers 101 and sample receptacles 103 using host conveyor assembly 102 and any one pairing of intermediate conveyor assemblies 133a, 133b, and 133c, and assay instruments 108a, 108b, and 108c. At step 302, intermediate conveyor assembly 133 awaits a carrier 101 and processing receptacle 103 coupled to the carrier 101 from host conveyor assembly 102. For example, intermediate conveyor assembly 133 waits for diverter 142 to transport a carrier 101 from host conveyor assembly 102 to input portion 146 of buffer conveyor subassembly 114.

At step 304, information read from carrier 101, receptacle 103, or both, on host conveyor assembly 102 is compared with information stored in laboratory information system 223 to determine whether a sample contained within the processing receptacle 103 is scheduled for an assay to be performed by the respective assay instrument 108. If it is verified that an assay is to be performed by the respective assay instrument 108 on the sample contained within processing receptacle 103, diverter 142 transports the respective carrier 101 and receptacle 103 to input portion 146 of buffer subassembly 114. At step 306, system 100 determines whether there is a predetermined minimum number of carriers 101 and receptacles 103 on input portion 146 of buffer conveyor subassembly 114 to begin processing with assay instrument 108. If a predetermined minimum number of carriers 101 and receptacles 103 are not present on input portion 146 of buffer conveyor subassembly 114, steps 302 and steps 304 are repeated. Once a predetermined minimum number of carriers 101 and receptacles 103 are present on input portion 146 of buffer conveyor subassembly 114, system 100 continues to step 308.

At step 308, information about the samples contained in receptacles 103 coupled to carriers on input portion 146 of buffer conveyor subassembly 114 is transmitted to assay instrument 108. This information can be information read from carriers 101 or receptacles 103 from any of the sensors within system 100, or the information can include specific identification of what assays to perform on which samples in receptacles 103 on input portion 146 of buffer conveyor assembly 114.

Next, at step 310, carriers 101 are transported one at a time to processing position 154 of assay instrument 108. For example, input portion 146 transports a carrier to position 147, diverter 150 transports carrier 101 to position 153, and gripper 188 of spur conveyor subassembly 116 transports carrier 101 to processing position 154.

At step 312, intermediate conveyor assembly verifies that the sample contained in receptacle 103 coupled to the carrier 101 at processing position 154 of assay instrument 108 is scheduled for an assay to be performed by the respective assay instrument 108. For example, information read by sensor 156a from carrier 101, receptacle 103, or both, when carrier 101 is at processing position 154 of assay instrument 108 is compared with information stored in laboratory information system 223 or with information received from host conveyor assembly 102 about the respective carrier 101 and receptacle 103. If the sample in receptacle 103 coupled to the carrier 101 at processing position 154 of assay instrument 108 is scheduled for an assay to be performed by the respective assay instrument 108, system 100 continues to step 314.

At step 314, assay instrument 108 processes the sample contained within receptacle 103 coupled to carrier 101 at processing position 154. For example, assay instrument 108 can aspirate a portion of the sample contained within receptacle 103 using automated pipettor 158 of assay instrument 108, and can dispense the aspirated portion of the sample into a cavity defined by an assay receptacle 160. In some embodiments, assay instrument 108 aspirates a plurality of portions of the sample contained within receptacle 103 using automated pipettor 158 of assay instrument 108, and dispenses the plurality of aspirated portions of the sample into either a plurality of cavities defined by a single assay receptacle 160 (for example, an MTU) or a plurality of cavities defined by a plurality of assay receptacles 160. Assay instrument 108 can then perform one or more assays on the sample portions dispensed into assay receptacle(s) 160.

At step 316, after interaction between assay instrument 108 and receptacle 103 coupled to the carrier 101 at processing position 154 of assay instrument 108, carrier 101 and the respective receptacle 103 are transported back to host conveyor assembly 102. For example, gripper 188 of spur conveyor subassembly 116 transports the carrier 101 from processing position 154 to position 153, diverter 150 transports the carrier 101 from position 153 to position 163 on output portion 162 of buffer conveyor subassembly 114, and output portion 162 transports the carrier 101 to a position adjacent diverter 164 at which diverter 164 transports the carrier 101 back to host conveyor assembly 102.

At step 318, system 100 determines whether there are additional carriers 101 and respective receptacles 103 for processing on input portion 146 of buffer conveyor subassembly 114. If so, steps 310-316 are repeated. If not, intermediate conveyor assembly 133 returns to step 306 and waits for a predetermined number of receptacles to be queued on input portion 146 of buffer conveyor subassembly 116.

3. Hardware and Software

Aspects of this disclosure are implemented via control and computing hardware components, user-created software, data input components, and data output components. Hardware components include computing and control modules (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to an operator for providing information to the operator, for example information as to the status of the instrument or a process being performed thereby, or such outputs may comprise inputs to other processes and/or control algorithms. Data input components comprise elements by which data is input for use by the control and computing hardware components. Such data inputs may comprise position sensors, motor encoders, as well as manual input elements, such as graphic user interfaces, keyboards, touch screens, microphones, switches, manually-operated scanners, voice-activated input, etc. Data output components may comprise hard drives or other storage media, graphic user interfaces, monitors, printers, indicator lights, or audible signal elements (e.g., buzzer, horn, bell, etc.).

Software comprises instructions stored on non-transitory computer-readable media which, when executed by the control and computing hardware, cause the control and computing hardware to perform one or more automated or semi-automated processes.

While the present disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the disclosure requires features or combinations of features other than those expressly recited in the claims. Accordingly, the present disclosure is deemed to include all modifications and variations encompassed within the spirit and scope of the following appended claims.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, and without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

While the invention has been described in connection with the above described embodiments, it is to be understood that the invention is not to be limited to the disclosed embodiments, but, on the contrary, is intended to cover various modifications and equivalent arrangements included within the spirit and scope of the appended claims.

All documents referred to herein are hereby incorporated by reference herein. No document, however, is admitted to be prior art to the claimed subject matter.

Furthermore, those of the appended claims which do not include language in the "means for performing a specified function" format permitted under 35 U.S.C. § 112, ¶6, are not intended to be interpreted under 35 U.S.C. § 112, ¶6, as being limited to the structure, material, or acts described in the present specification and their equivalents.

The invention claimed is:

1. A sample processing system comprising:
an instrument comprising a housing; and
a conveyor assembly configured to transport a carrier coupled to a receptacle to a processing position located within the housing of the instrument, wherein the conveyor assembly comprises:
　a buffer conveyor subassembly for transporting the carrier coupled to the receptacle from a host conveyor assembly to a spur conveyor subassembly;
　the spur conveyor subassembly, wherein the spur conveyor subassembly comprises:
　　a gripper configured to grasp the carrier coupled to the receptacle and
　　a diverter defining a first recess configured to receive the carrier, the diverter being rotatable between:
　　　(i) a first position at which the first recess is aligned with and positioned to receive the carrier from an input section of the buffer conveyor subassembly,
　　　(ii) a second position at which the first recess and the carrier received into the first recess at the first position are aligned with the gripper of the spur conveyor subassembly, and
　　　(iii) a third position at which the first recess is aligned with and returns the carrier to an output section of the buffer conveyor assembly,
　　wherein the gripper is configured to grasp the carrier at the second position outside the housing of the instrument and to move the carrier along a linear path between the second position and the processing position located within the housing of the instrument; and
　a cover enclosing at least a portion of the linear path between the second position and the processing position.

2. The sample processing system of claim 1, wherein the input section of the buffer conveyor subassembly comprises a first track for transporting the carrier from the host conveyor assembly to the spur conveyor subassembly, and wherein the output section of the buffer conveyor subassembly comprises a second track for transporting the carrier away from the spur conveyor subassembly.

3. The sample processing system of claim 2, wherein each of the first and second tracks comprises a movable component for transporting the carrier.

4. The sample processing system of claim 1, wherein the buffer conveyor subassembly is perpendicular to the spur conveyor subassembly.

5. The sample processing system of claim 1, wherein the diverter further defines a second recess, the second recess being at the first position when the first recess is at the second position.

6. The sample processing system of claim 5, wherein the diverter further defines a third recess and is rotatable between the first position, the second position, and the third position at which the first recess is aligned with one of the input and output sections of the buffer conveyor subassembly, the second recess is aligned with the gripper, and the third recess is aligned with the other one of the input and output sections of buffer conveyor subassembly, wherein the first, second and third recesses are equally spaced about a periphery of the diverter.

7. The sample processing system of claim 6, wherein the diverter is configured to simultaneously (i) return the carrier coupled to the receptacle from the first recess to the output section of the buffer conveyor subassembly, (ii) position a second carrier coupled to a second receptacle for transfer from the second recess to the gripper, and (iii) position the third recess at the first position to receive a third carrier coupled to a third receptacle into the third recess from the input section of the buffer conveyor subassembly.

8. The sample processing system of claim 6, wherein the gripper comprises at least two movable prongs configured to contact the receptacle coupled to the carrier.

9. The sample processing system of claim 1, wherein the linear path of the spur conveyor subassembly is a single path for transporting the carrier coupled to the receptacle from the second position to the processing position.

10. The sample processing system of claim 1, wherein the spur conveyor subassembly comprises a track configured to transport the gripper along the linear path between the second position and the processing position.

11. The sample processing system of claim 1, wherein the gripper is movably coupled to a base of the spur conveyor subassembly, and wherein the spur conveyor subassembly comprises a drive assembly coupled to the base, the drive assembly being configured to selectively move the gripper along the linear path between the second position and the processing position.

12. The sample processing system of claim 1, wherein the gripper is configured to move between (i) an open configuration in which the carrier coupled to the receptacle is not secured by the gripper in the second position and (ii) a closed configuration in which the carrier coupled to the receptacle is secured by the gripper.

13. The sample processing system of claim 12, wherein the gripper comprises at least two movable prongs configured to secure the carrier coupled to the receptacle to the gripper.

14. The sample processing system of claim 13, wherein the at least two movable prongs comprise a first movable prong and a second movable prong, each being pivotally coupled to a base of the gripper.

15. The sample processing system of claim 14, wherein the first movable prong and the second movable prong each comprise a first prong portion having an inner surface shaped to correspond to a perimeter of the carrier coupled to the receptacle.

16. The sample processing system of claim 15, wherein the first movable prong and the second movable prong each comprise a second prong portion extending laterally from the first prong portion and overlapping at least a portion of the carrier coupled to the receptacle when the gripper is in the closed configuration.

17. The sample processing system of claim 16, wherein the second prong portion of each of the first and second movable prongs is configured such that a distal end of each second prong portion contacts the receptacle coupled to the carrier when the gripper is in the closed configuration.

18. The sample processing system of claim 17, wherein the distal end of each second prong portion comprises an elastomer that contacts the receptacle coupled to the carrier when the gripper is in the closed configuration.

19. The sample processing system of claim 15, wherein the first prong portion of each of the first and second movable prongs defines a protrusion on the face of the first prong portion, the protrusion being configured to mate with a corresponding groove defined by the carrier coupled to the receptacle when the gripper is in the closed configuration.

20. The sample processing system of claim 1, wherein the cover defines an opening which is aligned with the processing position and configured to permit a distal end of a pipettor of the instrument or an associated pipette tip of the pipettor to pass therethrough such that the opening of the cover allows the pipettor to access the contents of the receptacle coupled to the carrier at the processing position.

21. The sample processing system of claim 20, wherein the cover comprises an alignment plate that defines a tapered surface surrounding the opening defined by the cover.

22. The sample processing system of claim 20, wherein the spur conveyor subassembly comprises a receptacle alignment block, the receptacle alignment block defining a recess configured to receive a portion of the receptacle coupled to the carrier at the processing position, such that the orientation of the receptacle is aligned with the opening of the cover and the direction of travel of the pipettor of the instrument.

* * * * *

UNITED STATES PATENT AND TRADEMARK OFFICE
CERTIFICATE OF CORRECTION

PATENT NO. : 11,846,644 B2
APPLICATION NO. : 15/931282
DATED : December 19, 2023
INVENTOR(S) : George T. Walker et al.

It is certified that error appears in the above-identified patent and that said Letters Patent is hereby corrected as shown below:

In the Specification

In Column 1, Line 7, delete "pending," and insert -- abandoned, --, therefor.

In Column 8, Line 1, delete "portion a" and insert -- portion of a --, therefor.

In Column 8, Line 2, delete "coupled a" and insert -- coupled to a --, therefor.

In Column 8, Line 13, delete "that as a" and insert -- that a --, therefor.

In Column 8, Line 22, delete "position" and insert -- position and --, therefor.

In Column 16, Line 18, delete "FIG. 25" and insert -- FIG. 25 is a --, therefor.

In Column 27, Line 62, delete "coupled a" and insert -- coupled to a --, therefor.

In Column 30, Line 9, delete "operative" and insert -- operatively --, therefor.

In Column 33, Line 60, delete "spur" and insert -- on spur --, therefor.

In Column 34, Line 20, delete "operative" and insert -- operatively --, therefor.

In Column 36, Line 7, delete "relative" and insert -- relative to --, therefor.

In Column 36, Line 60, delete "corresponds" and insert -- corresponds to --, therefor.

In Column 37, Line 53, delete "such than" and insert -- such that --, therefor.

In Column 49, Line 9, delete "configured" and insert -- configured to --, therefor.

Signed and Sealed this
Twenty-third Day of April, 2024

Katherine Kelly Vidal
*Director of the United States Patent and Trademark Office*

In Column 51, Line 58, delete "once" and insert -- one --, therefor.

In the Claims

In Column 65, Line 42, in Claim 1, delete "receptacle" and insert -- receptacle; --, therefor.